United States Patent [19]
Bartrolí et al.

[11] Patent Number: 5,478,826
[45] Date of Patent: Dec. 26, 1995

[54] ORALLY ACTIVE AZOLE DERIVATIVES

[75] Inventors: Javier Bartrolí; Enric Turmo; Manuel Anguita; Elena Carceller; Carmen Almansa, all of Barcelona, Spain

[73] Assignee: J. Uriach & Cia. S.A., Barcelona, Spain

[21] Appl. No.: 213,208

[22] Filed: Mar. 15, 1994

[30] Foreign Application Priority Data

Mar. 15, 1993 [ES] Spain ..................... 9300537

[51] Int. Cl.⁶ ............... A01N 43/84; A61K 31/535; C07D 413/06
[52] U.S. Cl. ................. 514/235.8; 514/236.2; 544/132; 544/139
[58] Field of Search ................. 544/132, 139; 514/235.8, 236.2

[56] References Cited

U.S. PATENT DOCUMENTS 5,149,707  9/1992  Bartrolí et al. ............ 514/396

FOREIGN PATENT DOCUMENTS

| | | |
|---|---|---|
| 54974 | 6/1982 | European Pat. Off. |
| 97469 | 1/1984 | European Pat. Off. |
| 145314 | 6/1985 | European Pat. Off. |
| 332387 | 9/1989 | European Pat. Off. |
| 435081 | 7/1991 | European Pat. Off. |
| 472392 | 2/1992 | European Pat. Off. |
| 480215 | 4/1992 | European Pat. Off. |
| 510700 | 10/1992 | European Pat. Off. |
| 548553 | 6/1993 | European Pat. Off. |
| 8503672 | 2/1987 | Spain . |
| 8601973 | 3/1987 | Spain . |
| 9217474 | 10/1992 | WIPO . |

OTHER PUBLICATIONS

T. Tanaka et al., "Triazole Antifungals. V. ) Synthesis and Antifungal Activities of Some Amides Related to 3–Acylamino–2–aryl–1–triazolyl–2–butanol." *Chem. Pharm. Bull.* 40(3) 661–665 (1992).

Chemical Abstract No. 139186j, "Synthesis and antifungal activity of triazolylpropanol derivatives." 119(13), 875 (1993).

Konosu, Toshiyuki, Tajima, Yawara, Takeda, Noriko, Miyaoka, Takeo, Kasahara, Mayumi, Yasuda, Hiroshi and Oida, Sadao: Triazole Antifungals. II. Synthesis and Antifungal Activities of 3–Acyl–4–methyloxazolidine Derivatives. *Chem. Pharm. Bull.* 38(9) 2476–2486 (1990).

Evans, David A., Britton, Thomas C., Ellman, Jon A.: Contrasteric Carboximide Hydrolysis With Lithium Hydroperoxide. *Tetrahedron Letters*, vol. 28, No. 49, pp. 6141–6144, (1987).

Konosu, Toshiyuki, Tajima, Yawara, Takeda, Noriko, Miyaoka, Takeo, Kasahara, Mayumi, Yasuda, Hiroshi, Oida, Sadao: Triazole Antifungals. IV. Synthesis and Antifungal Activities of 3–Acylamino–2–aryl–2–butanol Derivatives. *Chem. Pharm. Bull.* 39(10):2581–2589 (1991).

*Primary Examiner*—Robert W. Ramsuer
*Attorney, Agent, or Firm*—Rothwell, Figg, Ernst & Kurz

[57] ABSTRACT

The present invention relates to new orally active azole derivatives with antifungal activity of formula I

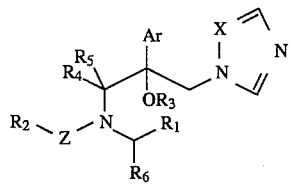

wherein: X is CH or N; Ar represents phenyl substituted with halogen and/or trifluoromethyl; Z is —C(=O)— or —SO$_2$—; R$_1$ is CN, CO$_2$H, CO$_2$R$_7$, CONR$_8$R$_9$ or CH$_2$Y and then R$_3$ is hydrogen, or R$_1$ together with R$_3$ forms a ring of formula I'

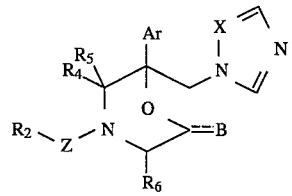

wherein B is O, hydroxy or hydrogen; R$_4$ is C$_{1-4}$ alkyl; R$_5$, R$_6$, R$_8$ and R$_9$ are hydrogen or C$_{1-4}$ alkyl; Y is —OH, —OR$_7$, —OC(=O)R$_7$, —NR$_8$R$_9$, —NHC(=O)OR$_7$; R$_7$ is C$_1$–C$_4$-alkyl, phenyl-C$_1$–C$_4$-alkyl or optionally substituted phenyl; when Z is —C(=O)—, R$_2$ is optionally susbtituted phenyl, or naphtyl; when Z is —SO$_2$—, R$_2$ is C$_{1-4}$ alkyl, phenyl-C$_{1-4}$-alkyl or optionally susbtituted phenyl.

29 Claims, No Drawings

ORALLY ACTIVE AZOLE DERIVATIVES

FIELD OF THE INVENTION

The present invention relates to a new series of azole derivatives of general formula I having a potent antifungal activity. The invention also relates to a process for their preparation, to the pharmaceutical compositions containing them and to their use for the treatment of fungal diseases.

DESCRIPTION OF THE PRIOR ART

The compounds of the present invention are antifungal agents whose mechanism of action is based on the inhibition of the biosynthesis of ergosterol in fungi. Other antifungal agents having this type of activity are known in the medical practice and are currently used in therapy. Some of them are applied in the topical treatment of fungal infections of the skin, vagina and nails, such as candidiasis, dermatophytosis and pityriasis. More recently discovered compounds are used orally in the treatment of systemic and organ mycoses, such as systemic candidiasis, aspergillosis, criptoccocal meningitis, coccidioidomycosis, paracoccidioidiomycosis, histoplasmosis, sporotrichosis, chromoblastomycosis and blastomycosis. These diseases appear frequently in immunosupressed patients, such as AIDS and cancer patients. Some other compounds related to the ones of the present invention are also used as agrochemicals to protect plants from a variety of fungi.

European patent application EP 332,387 describes, among others, certain antifungal compounds of general formula

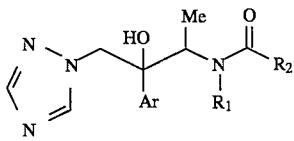

wherein:
Ar is a phenyl group optionally substituted by one or two halogen or trifluoromethyl groups; $R_2$ is $C_1$–$C_6$ alkyl, haloalkyl, optionally substituted phenyl, naphtyl or an heterocycle; and R1 is H or $C_1$–$C_4$ alkyl. These compounds are useful for the treatment of fungal diseases in animals and plants.

In a study aimed at improving the activity of these compounds, we have found that an increase in the lenght of the alkyl radical $R_1$ in a compound of the above formula (that is to say the change of methyl for ethyl, propyl and butyl) translates into a progressive loss of in vivo activity. But, surprisingly, the introduction of an heteroatom into the group $R_1$ leads to a recovery or even an improvement of the activity of the prior art compounds. The new compounds do not fall within the scope of the above mentioned patent application. Thus, the present invention describes new compounds structurally related to the above mentioned, where the nature of the substituent $R_1$ has been substantially modified so as to contain one or more heteroatoms.

DESCRIPTION OF THE INVENTION

The present invention relates to new compounds of general formula I as racemates, diastereomer mixtures or as homochiral compounds

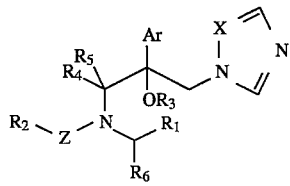

wherein
X is CH or N;
Ar represents phenyl or a phenyl ring substituted with one or more halogen and/or trifluoromethyl groups;
Z is —C(=O)— or —$SO_2$—;
$R_1$ is CN, $CO_2H$, $CO_2R_7$, $CONR_8R_9$ or $CH_2Y$ and then $R_3$ is hydrogen, or $R_1$ together with $R_3$ and the remainder or salt compound of Formula I forms a six-membered ring of formula I forms a six-membered ring of formula I'

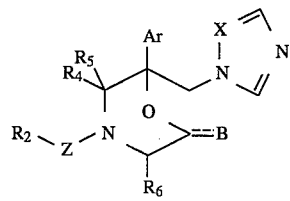

wherein B is O, in which case the dotted line represents a covalent bond, or B is hydroxy, fluorine, hydrogen or 1-H-1,2,4-triazol-1-yl, in which case the dotted line is absent;
Y is —OH, —$OR_7$, —OC(=O)$R_7$, —$NR_8R_9$, —NHC(=O)$OR_7$, 1-H-1,2,4 -triazol-1-yl or 1H-imidazol-1-yl;
$R_4$ is $C_{1-4}$ alkyl;
$R_5$, $R_6$, $R_8$ and $R_9$ are independently hydrogen or $C_{1-4}$ alkyl;
$R_7$ is $C_1$–$C_4$-alkyl, phenyl-$C_1$–$C_4$-alkyl, phenyl or phenyl susbtituted with a group $R_{10}$;
when Z is —C(=O)—, $R_2$ is phenyl, phenyl substituted with one or more groups $R_{10}$, or naphtyl;
when Z is —$SO_2$—, $R_2$ is $C_{1-4}$ alkyl, phenyl-$C_{1-4}$-alkyl, phenyl or phenyl substituted with one or more groups $R_{10}$;
$R_{10}$ represents $C_1$–$C_4$ alkyl, $C_1$–$C_4$ haloalkyl, C1-C4 alkoxy, $C_1$–$C_4$ haloalkoxy, halogen, nitro, cyano, hydroxy, benzyloxy, hydroxymethyl, a group of formula —$CH_2$—OCO—($C_{1-4}$ alkyl), a group of formula —CO—($C_{1-4}$ alkyl), a group of formula —COO—($C_{1-4}$ alkyl), a group formula —$SO_z$($C_{1-4}$ alkyl) wherein z is 0, 1 or 2, amino, mono- or dialkylamino wherein alkyl means $C_1$–$C_4$ alkyl; and
the salts and solvates thereof.

The invention also provides a pharmaceutical composition which comprises an effective amount of a compound of formula I or a pharmaceutically acceptable salt or solvate thereof in admixture with a pharmaceutically acceptable excipient.

The present invention further provides the use of a compound of formula I or a pharmaceutically acceptable salt or solvate thereof in the treatment or prophylaxis of fungal infections. Accordingly, the invention provides a method for treating or preventing fungal infections in an animal, which may be a human being, which comprises administering to an animal in need thereof an effective amount of a compound of formula I or a pharmaceutically acceptable salt or solvate thereof.

The compounds of the present invention possess antifungal properties which are useful in combatting a wide variety of plant fungal diseases. The invention thus provides the use of a compound of formula I or a salt or solvate thereof for the treatment or prophylaxis of fungal infections in plants. Accordingly, the invention provides a method of combatting fungal diseases in a plant which comprises administering to the plant an effective amount of a compound of formula I or a salt or solvate thereof. The invention still further provides an agrochemical composition comprising an effective amount of a compound of formula I or a salt or solvate thereof in admixture with an agronomically acceptable excipient.

The invention also provides a process for preparing a compound of formula I, which process comprises
(a) reacting a compound of formula II

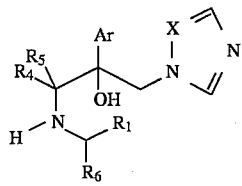

wherein X, Ar, $R_1$, $R_4$, $R_5$ and $R_6$ have the previously defined meaning, with an acid of formula $R_2COOH$ or a reactive derivative thereof, such as the acid chloride, or with a sulfonyl chloride of formula $R_2SO_2Cl$ under standard experimental conditions, and optionally interconverting the group $R_1$ of a compound of formula I into other groups R1 by standard chemical reactions; or
(b) oxidating a compound of formula I wherein $R_1$ is $CH_2OH$ to the aldehyde to give a lactol of formula I', wherein B is hydroxy and the dotted line is absent, and optionally transforming this hydroxy group into other groups by standard chemical reactions; or
(c) reacting a compound of formula I wherein $R_1$ is $CO_2H$ with an appropriate dehydrating agent to give a lactone of formula I' wherein B is O and the dotted line represents a covalent bond; or
(d) subjecting a compound of formula I wherein $R_1$ is $CH_2OH$ to standard Mitsunobu conditions to give a compound of formula I', wherein B is hydrogen and the dotted line is absent.

Also included in the present invention are novel intermediates of formula II

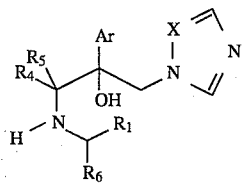

wherein X, Ar, $R_1$, $R_4$, $R_5$ and $R_6$ are as defined for compounds of formula I.

In the above definitions, a $C_{1-4}$ alkyl group means a linear or branched alkyl chain containing from 1 to 4 carbon atoms. It includes methyl, ethyl, propyl, isopropyl, butyl, isobutyl, sec-butyl and tert-butyl.

A $C_{1-4}$ haloalkyl group means a group resulting from the substitution of one or more hydrogen atoms of a $C_{1-4}$ alkyl group by one or more halogen atoms (i.e. fluorine, chlorine, bromine or iodine), which can be the same or different. Examples include trifluoromethyl, fluoromethyl, chloroethyl, fluoroethyl, iodoethyl, pentafluoroethyl, fluoropropyl, chloropropyl, 2,2,3,3,3 -pentafluoropropyl, 2,2,3,3-tetrafluoropropyl, heptafluoropropyl, etc.

A $C_{1-4}$ alkoxy group means a group derived from the union of a $C_{1-4}$ alkyl group to an oxygen atom of an ether functional group. Examples include methoxy, ethoxy, propoxy, isopropoxy, butoxy, isobutoxy, sec-butoxy and tert-butoxy.

A $C_{1-4}$ haloalkoxy group means a group resulting from the substitution of one or more hydrogen atoms of a $C_{1-4}$ alkoxy group like the above mentioned by one or more halogen atoms, which can be the same or different. Examples include trifluoromethoxy, fluoromethoxy, chloroethoxy, fluoroethoxy, iodoethoxy, 2,2,2-trifluoroethoxy, pentafluoroethoxy, fluoropropoxy, chloropropoxy, 2,2,3,3-tetrafluoropropoxy, 2,2,3,3,3 -pentafluoropropoxy, heptafluoropropoxy, etc.

In the compounds of the present invention, X represents a nitrogen atom or a CH group, but preferably is a nitrogen atom.

In the compounds where $R_2$ represents a substituted phenyl ring, said substituent(s) can be $C_1-C_4$ alkyl, $C_1-C_4$ haloalkyl, $C_1-C_4$ alkoxy, $C_1-C_4$ haloalkoxy, halogen, nitro, cyano, hydroxy, benzyloxy, hydroxymethyl, a group of formula —$CH_2$—OCO—($C_{1-4}$ alkyl), a group of formula —CO—($C_{1-4}$ alkyl), a group of formula —COO—($C_{1-4}$ alkyl), a group formula —$SO_z(C_{1-4}$ alkyl) wherein z is 0, 1 or 2, amino, mono- or dialkylamino wherein alkyl means $C_1-C_4$ alkyl. When there are more than one substituent, they can be the same or different. When the substituent is an halogen atom, this can be fluorine, chlorine, bromine or iodine. Examples of substituted phenyl rings include 4 -fluorophenyl, 4-chlorophenyl, 4-bromophenyl, 4-iodophenyl, 2,4 -difluorophenyl, 3,4-difluorophenyl, 2,4-dichlorophenyl, 2,5 -dichlorophenyl, pentafluorophenyl, 3-(trifluoromethyl)phenyl, 4-(trifluoromethyl)phenyl, 4 -(trichloromethyl)phenyl, 2-fluoro-5-(trifluoromethyl)phenyl, 2-fluoro-4 -(trifluoromethyl)phenyl, 3-fluoro-4-(trifluoromethyl)phenyl, 4 -(difluoromethoxy)phenyl, 4-(trifluoromethoxy)phenyl, 4-(2,2,2 -trifluoroethoxy)phenyl, 4-(2,2,3,3-tetrafluoropropoxy)phenyl, 3-nitrophenyl, 4 -nitrophenyl, 2-fluoro-4-nitrophenyl, 3-cyanophenyl, 4-cyanophenyl, 2 -chloro-4-cyanophenyl, 4-(methoxycarbonyl)phenyl, 2-fluoro-4 -(ethoxycarbonyl)phenyl, 4-(methylthio)phenyl, 4-(methylsulfinyl)phenyl and 4-(methylsulfonyl)phenyl, of which 4-chlorophenyl, 4-fluorophenyl, 4 -(trifluoromethyl)phenyl, 2-fluoro-4-(trifluoromethyl)phenyl, 4-cyanophenyl, 4-nitrophenyl, 4-(trifluoromethoxy)phenyl, 4-(2,2,2-trifluoroethoxy)phenyl and 4-(2,2,3,3-tetrafluoropropoxy)phenyl are preferred, and 4-chlorophenyl, 4 -fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl and 4-(2,2,3,3 -tetrafluoropropoxy)phenyl are more preferred.

In the compounds of the present invention, $R_2$ can have all the above mentioned meanings, but preferably is phenyl substituted with one or more groups $R_{10}$.

In the compounds of the present invention Ar represents a phenyl group or a phenyl group substituted with one or more halogen and/or trifluoromethyl groups. The halogen atoms may be fluorine, chlorine, bromine or iodine atoms, of which fluorine and chlorine atoms are preferred. There may be one or more such substituents on the phenyl group, and where there are more than one, these may be the same or different. The substituents may be on any available position of the phenyl group, but they are preferably on the 2- and/or 4-positions. Examples of the Ar group include the phenyl group itself, 4-(trifluoromethyl)phenyl, 4-fluorophenyl, 2-chloro-4 -fluorophenyl, 4-chloro-2-fluorophenyl, 4-bromophenyl, 2-fluoro-4-iodophenyl, 2,4-dichlorophenyl, 2,4-difluorophenyl, 4-chlorophenyl and 2-fluoro-4-(trifluoromethyl)phenyl, of which 4-fluorophenyl, 2-chloro-4-fluorophenyl, 2,4-dichlorophenyl, 2,4-difluorophenyl and 4-chlorophenyl are preferred, and 2,4-dichlorophenyl, 2,4-difluorophenyl, 4-(trifluoromethyl)phenyl and 4-chlorophenyl are more preferred.

In a compound of formula I, Z represents —C(=O)— or —SO$_2$—, but preferably represents —C(=O)—.

In a compound of formula I, R$_4$ is C$_{1-4}$ alkyl, but preferably is methyl.

In a compound of formula I, R$_5$ is hydrogen or C$_{1-4}$ alkyl, but preferably is hydrogen.

In a compound of formula I, R$_6$ is hydrogen or C$_{1-4}$ alkyl, but preferably is hydrogen or methyl.

In those compounds where R$_1$ together with R$_3$ and the remainder of salt compound or Formula I may form a six-membered ring of formula I'

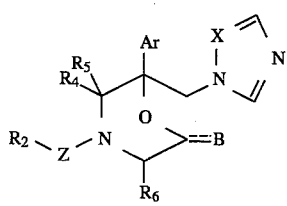

wherein B is O, in which case the dotted line represents a covalent bond, or B is hydroxy, fluorine, hydrogen or 1-H-1,2,4-triazol-1-yl, in which case the dotted line is absent, those in which B represents O, hydroxy or hydrogen are preferred.

Preferred embodiments of the present invention are those compounds of formula I wherein:
X is N;
R$_2$ is phenyl or phenyl substituted with one or more groups R$_{10}$; and
Ar, Z, R$_1$, R$_3$, R$_4$, R$_5$, R$_6$ and R$_{10}$ have the previously defined meaning.

More preferred embodiments of the present invention are those compounds of formula I wherein:
X is N;
Z is —C(=O)—;
R$_2$ is phenyl or phenyl substituted with one or more groups R$_{10}$; and
Ar, R$_1$, R$_3$, R$_4$, R$_5$, R$_6$ and R$_{10}$ have the previously defined meaning.

Still more preferred embodiments of the present invention are those compounds of formula I wherein:
X is N;
Z is —C(=O)—;
R$_2$ is phenyl or phenyl substituted with one or more groups R$_{10}$;
R$_4$ is methyl;
R$_5$ is hydrogen or methyl; and
Ar, R$_1$, R$_3$, R$_6$ and R$_{10}$ have the previously defined meaning.

Particularly preferred embodiments of the present invention are the following groups of compounds:
I) Those compounds of formula I where:
X is N;
Z is —C(=O)—;
R$_2$ is 4-chlorophenyl, 4-fluorophenyl, 4-(trifluoromethyl)phenyl, 2-fluoro-4-(trifluoromethyl)phenyl, 4-cyanophenyl, 4-nitrophenyl, 4-(trifluoromethoxy)phenyl, 4-(2,2,2-trifluoroethoxy)phenyl or 4-(2,2,3,3-tetrafluoropropoxy)phenyl;
R$_4$ is methyl;
R$_5$ is hydrogen;
R$_1$ is CN, CH$_2$NH$_2$ or CH$_2$OH;
R$_3$ is hydrogen;
Ar is 4-fluorophenyl, 2-chloro-4-fluorophenyl, 2,4-dichlorophenyl, 2,4-difluorophenyl, 4-(trifluoromethyl)phenyl or 4-chlorophenyl; and
R$_6$ is hydrogen.
II) Those compounds of formula I' where:
X is N;
Z is —C(=O)—;
R$_2$ is 4-chlorophenyl, 4-fluorophenyl, 4-(trifluoromethyl)phenyl, 2-fluoro-4-(trifluoromethyl)phenyl, 4-cyanophenyl, 4-nitrophenyl, 4-(trifluoromethoxy)phenyl, 4-(2,2,2-trifluoroethoxy)phenyl or 4-(2,2,3,3-tetrafluoropropoxy)phenyl;
R$_4$ is methyl;
R$_5$ is hydrogen;
B is O in which case the dotted line represents a covalent bond, or B is hydroxy, in which case the dotted line is absent;
Ar is 4-fluorophenyl, 2-chloro-4-fluorophenyl, 2,4-dichlorophenyl, 2,4-difluorophenyl, 4-(trifluoromethyl)phenyl or 4-chlorophenyl; and
R$_6$ is hydrogen.

Most preferred embodiments of the present invention are the following groups of compounds:
I) Those compound of formula I where:
X is N;
Z is —C(=O)—;
R$_2$ is 4-chlorophenyl, 4-fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl or 4-(2,2,3,3-tetrafluoropropoxy)phenyl;
R$_4$ is methyl;
R$_5$ is hydrogen;
R$_1$ is CH$_2$OH;
R$_3$ is hydrogen;
Ar is 2,4-dichlorophenyl, 2,4-difluorophenyl, 4-(trifluoromethyl)phenyl or 4-chlorophenyl; and
R$_6$ is hydrogen.
II) Those compounds of formula I' where:
X is N;
Z is —C(=O)—;
R$_2$ is 4-chlorophenyl, 4-fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl or 4-(2,2,3,3-tetrafluoropropoxy)phenyl;
R$_4$ is methyl;
R$_5$ is hydrogen;
B is O in which case the dotted line represents a covalent bond;
Ar is 2,4-dichlorophenyl, 2,4-difluorophenyl, 4-(trifluoromethyl)phenyl or 4-chlorophenyl; and
R$_6$ is hydrogen.
III) Those compounds of formula I' where:
X is N;
Z is —C(=O)—;
R$_2$ is 4-chlorophenyl, 4-fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl or 4-(2,2,3,3-tetrafluoropropoxy)phenyl;
R$_4$ is methyl;
R$_5$ is hydrogen;
B is hydroxy, in which case the dotted line is absent;
Ar is 2,4-dichlorophenyl, 2,4-difluorophenyl, 4-(trifluoromethyl)phenyl or 4-chlorophenyl; and
R$_6$ is hydrogen.

The compounds of formula I contain one or more basic nitrogen atoms and, consequently, they can form salts with acids, which are also included in the present invention. There is no limitation on the nature of these salts, provided that, when used for therapeutic purposes, they are pharmaceutically acceptable, which, as is well-known in the art, means that they do not have reduced activity (or unacceptable reduced activity) or increased toxicity (or unacceptable increased toxicity) compared with the free compounds. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid or maleic acid. The salts are prepared by reacting the free base with a sufficient amount of the desired acid to produce a salt in the conventional manner. Free bases and their salts differ in certain physical properties, such as solubility, but they are equivalent for the purposes of the invention.

The compounds of the present invention can exist in unsolvated as well as solvated forms, including hydrated forms. In general, the solvated forms, with pharmaceutically acceptable solvents such as water, ethanol and the like, are equivalent to the unsolvated forms for the purposes of the invention.

The compounds of the present invention can exist as different diastereoisomers and/or optical isomers because of the existence of asymmetric carbons in their skeleton. These stereoisomers and the mixtures thereof are all included in the present invention. In particular, when $R_4$ is methyl and $R_5$ is hydrogen, the compounds wherein the carbon to which the Ar group is bonded and the carbon to which $R_4$ is bonded bear the (R*,R*) relative stereochemistry are preferable, and the homochiral compounds wherein the carbon to which the Ar group is bonded and the carbon to which $R_4$ is bonded are both R-configurated are more preferable.

Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optically pure isomers can also be individually obtained using enantiospecific synthesis, as explained in more detail below. As stated above, the present invention covers the individual isomers as well as their mixtures (e.g. racemic mixtures), whether as obtained by synthesis or by physically mixing them up.

The present invention also provides a process for the preparation of the compounds of formula I. The precise method used for the preparation of a given compound will vary depending on its chemical structure. The general method for their preparation is illustrated in Schemes 1, 2 and 3.

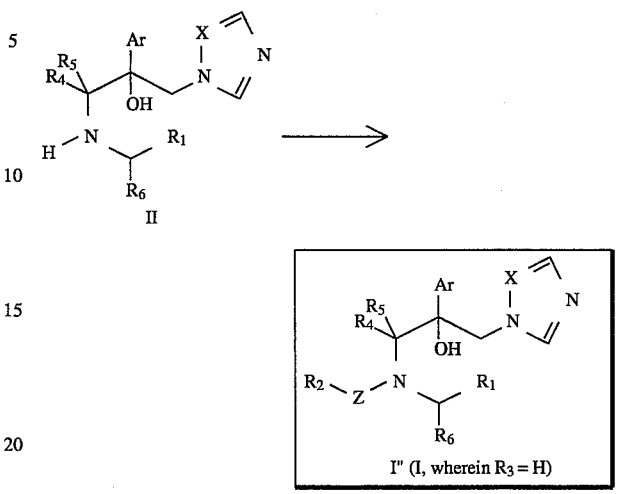

Scheme 1

Wherein X, Ar, Z, $R_1$, $R_4$, $R_5$ and $R_6$ have the previously defined meaning.

As shown in Scheme 1, compounds of formula I" (i.e. compounds of formula I, wherein $R_3$ represents hydrogen) are prepared from amines of formula II by reaction with an acid chloride of formula $R_2COCl$ or another reactive derivative of $R_2COOH$ or a sulfonyl chloride of formula $R_2SO_2Cl$ in the presence of a proton scavenger, such as triethylamine or pyridine, in a suitable solvent, such as chloroform or dichloromethane, or using the base as solvent. The reaction is carried out at a temperature between $-10°$ C. and that of the boiling point of the solvent, preferably between $0°$ and $25°$ C. The time required for the reaction may vary widely, depending on many factors, notably the reaction temperature and the nature of the reagents, but in general a period of time from 30 min to 24 h will usually suffice. If required, the compounds thus obtained can be purified by conventional methods such as flash chromatography or recrystallization. As an alternative to the acid chloride, the anhydride can be employed. Alternatively, compounds of formula I" wherein $Z=-C(=O)-$ may be prepared by a coupling reaction between amines of formula II and an acid of formula $R_2COOH$. This process can be carried out using any conventional reaction of amide bond formation, such as reacting an amine with an acid in the presence of an appropriate condensing agent such as dicyclohexylcarbodiimide (DCC) alone or in combination with 1-hydroxybenzotriazole.

Acids of formula $R_2COOH$ and the reactive derivatives thereof (i.e. acid chloride or anhydride) as well as sulfonyl chlorides of formula $R_2SO_2Cl$ are either commercially available, or widely described in the literature or can be prepared by methods similar to those described, starting from commercially available products.

Furthermore, the group $R_1$ in a compound of formula I thus obtained may be transformed into other groups $R_1$ by standard chemical reactions, which are well known to those skilled in the art.

For example, if $R_1$ is a benzyl ether, this product can be converted to the alcohol ($R_1=CH_2OH$) by hydrogenation in the presence of a catalyst, such as palladium or platinum, in a suitable solvent such as an alcohol, for example ethanol, at a hydrogen pressure between 1 and 5 atm. The reaction can take place over a wide range of temperatures and the precise temperature is not critical to the invention. In general, we find it convenient to carry out the reaction at about room temperature.

The resulting alcohol can be transformed into other functionalities well known in organic chemistry, such as an ester, using standard reactions.

Furthermore, a group $R_1$ of formula $CH_2NHC(=O)OR_7$ may be transformed into an amine group following standard conditions; when it is a $CH_2NHBOC$ group, this process can be carried out for example by treatment with trifluoroacetic acid in dioxane or with hydrochloric acid in methanol.

When $R_1=CO_2R_7$, this product can be hydrolized to the acid ($R_1=CO_2H$) following conventional procedures. If $R_1$ is a benzyl ester, this process can be carried out by hydrogenation under the same experimental conditions mentioned above for benzyl ethers.

Compounds as seen in formula I wherein $R^1$ together with $R^3$ form a ring of formula I', wherein B is hydrogen and the dotted line is absent, can be obtained directly from the corresponding alcohol derivatives of formula I (i.e. compounds of formula I wherein $R_1=CH_2OH$) under standard Mitsunobu conditions (i.e. diethylazadicarboxylate, triphenylphosphine).

Compounds of formula I wherein $R^1$ together with $R^3$ form a ring of formula I', wherein B is hydroxy, are prepared from the corresponding alcohol derivatives of formula I (i.e. compounds of formula I wherein $R_1=CH_2OH$), as shown in Scheme 2:

Scheme 2

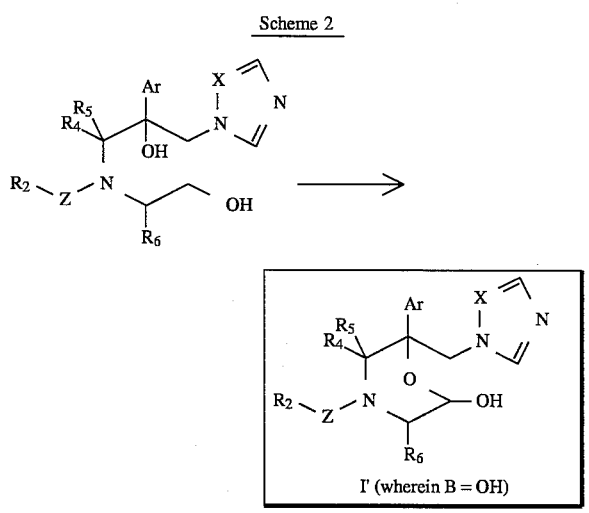

I' (wherein B = OH)

This transformation (Scheme 2) involves the oxidation of a primary alcohol to an aldehyde, which spontaneously forms a cyclic acetal (lactol) with the tertiary hydroxyl group. This can be achieved by any known oxidation conditions currently used for the transformation of alcohols into aldehydes. One set of such conditions are the so-called Moffat oxidations which involve the use of activated DMSO and a base. Thus, we have found that treatment of DMSO with an activating agent, such as oxalyl chloride or trifluoroacetic anhydride, in the presence of a suitable solvent, such as dichloromethane or chloroform, followed by addition of the alcohol at low temperatures, and finally treatment with a base, such as triethylamine, affords the lactol in good yields. Alternatively, the oxidation of the primary alcohol to the aldehyde stage can be achieved by other known methods, such as the Sharpless' ruthenium oxidation which involves the use of N-methylmorpholine N-oxide and a catalytic amount of tris-triphenylphosphine ruthenium (II) dichloride in a polar solvent, such as acetone.

The hydroxy group in a compound of formula I' thus obtained may be transformed into other groups following standard procedures. For example, it may be transformed into a fluorine atom (e.g. with diethylaminosulfur trifluoride in dichloromethane, at $-10°$ C.) or into a 1-H-1,2,4-triazol-1-yl group (e.g. with diethylazadicarboxylate/1,2,4-triazole/triphenylphosphine in tetrahydrofuran, at $0°$ C.-room temperature).

Compounds of formula I wherein $R^1$ together with $R^3$ and the remainder of said compound of Formula I form a ring of formula I', wherein B is O and the dotted line represents a covalent bond, are prepared from the corresponding acids of formula I (i.e. compounds of formula I wherein $R_1=CO_2H$) using an appropriate dehydrating agent, as formula I wherein $R_1=CO_2H$) using an appropriate dehydrating agent, as shown in Scheme 3:

Scheme 3

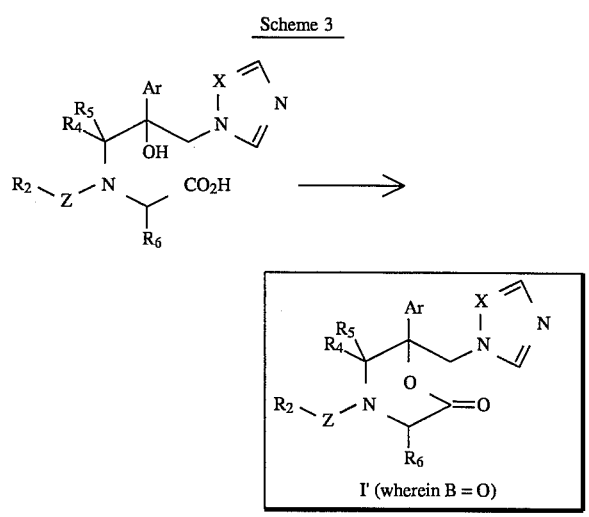

I' (wherein B = O)

The transformation can be achieved by using DCC in the presence of a suitable solvent, such as dimethylformamide, at a wide range of temperatures and reaction conditions. Filtration of the precipitated urea formed during the reaction affords the lactone in very high yields. Alternatively, the transformation can be performed under other dehydrating conditions, all of them involving the in situ formation of an active acid derivative. Suitable reagents for this transformation are trifluoroacetic anhydride, oxalyl chloride or thionyl chloride, among others. The reaction can be done at a wide range of conditions but we have found that heating a pyridine solution containing the hydroxyacid and trifluoroacetic anhydride gives excellent yields of the desired lactone.

In some cases, these compounds may also be obtained from compounds of formula I wherein $R_1=CH_2OH$ by oxidation of the primary alcohol to the acid to give a lactone of formula I'. This process can be carried out by treatment of the alcohol, for example, with Fetizon's reagent ($Ag_2CO_3$) suspended in celite in a suitable solvent, such as benzene, at the temperature of the boiling point of the solvent.

Compounds of formula I wherein $R_1$ represents $CONR_8R_9$ can be obtained by treatment of the corresponding lactone with ammonium hydroxide or an amine. Selective reduction of the amides thus obtained using for example $LiBH_4$ in diglyme affords the compounds of formula I wherein $Y=NR_8R_9$.

Starting compounds of formula II are prepared from amines of formula III as shown in Scheme 4 below:

Scheme 4

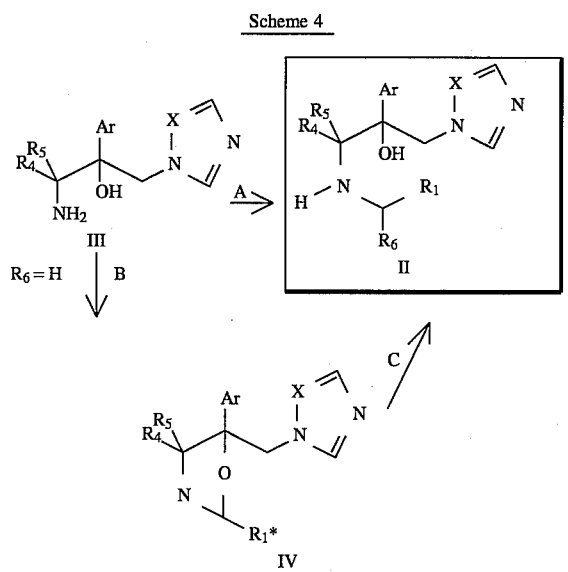

Wherein $R_1^*$ represents $R_1$ or a group convertible thereto.

Amines of formula II may be obtained by treatment of an amine of formula III with an alkylating agent of formula $WCHR_1R_6$ (wherein W is a leaving group such as chloro, bromo, mesyloxy or p-toluenesulfonyloxy, and $R_1$ and $R_6$ have the previously defined meaning) (step A) in the presence of an amine, such as triethylamine or pyridine, and in a solvent. Suitable solvents are preferentially those with high polarity such as tetrahydrofuran, acetonitrile or dioxane. The reaction is carried out at a temperature between room temperature and that of the boiling point of the solvent; the reaction time will depend mainly on the nature of the alkylating agent and the temperature, but a period of time between 1 h and 72 h will usually suffice.

Alternatively, amines of formula II wherein $R_6$=H may also be obtained by the following sequence: reaction of an amine of formula III (step B) with a compound of formula $R_1^*CHO$, wherein $R_1^*$ has the previously defined meaning, in a suitable solvent such as an aromatic hydrocarbon, for example benzene or toluene, at a temperature between 50° C. and that of the boiling point of the solvent, to give the corresponding oxazolidine of formula IV (generally as a mixture of stereoisomers); if necessary, transformation of $R_1^*$ to a group $R_1$ following conventional procedures; and finally, reduction of IV (step C) with an excess of lithium aluminium hydride ($LiAlH_4$) in an inert solvent. Examples of suitable solvents include: ethers, such as diethyl ether, tetrahydrofuran or dioxane. The reaction is carried out at a temperature between −20° C. and that of the boiling point of the solvent.

Furthermore, it is also possible to transform the group $R_1$ of a compound of formula II into other groups $R_1$ by standard chemical reactions, as it will become apparent to a person skilled in the art.

Compounds of formulae $WCHR_1 R_6$ and $R_1^*CHO$ are either commercially available, or widely described in the literature or can be prepared by methods similar to those described, starting from commercially available products.

Amines of formula III can be prepared according to the procedure described in patent application EP 332387.

The present invention also provides a method for preparing the optically pure isomers of the compounds of formula I. They may be obtained following the same general procedure explained above for the preparation of compounds of formula I, but starting from the optically pure amines of formula III.

Optically pure amines of formula III wherein $R_5$=H having the (R,R)absolute stereochemistry may be prepared according to the procedure described in EP 332387. However, the synthesis thereby reported is long and tedious, it requires the use of expensive reactants and in some steps racemization is somewhat unpredictable. We therefore undertook a study aimed at obtaining the homochiral products of formula III (i.e. the precursors of the homochiral compounds of formula I of the present invention) in a more practical manner. Thus, the present invention further provides a new, highly convergent synthesis of amines of formula III consisting in an enantioselective process using the Evans' chiral oxazolidinones. The process summarized in Scheme 5.

Scheme 5

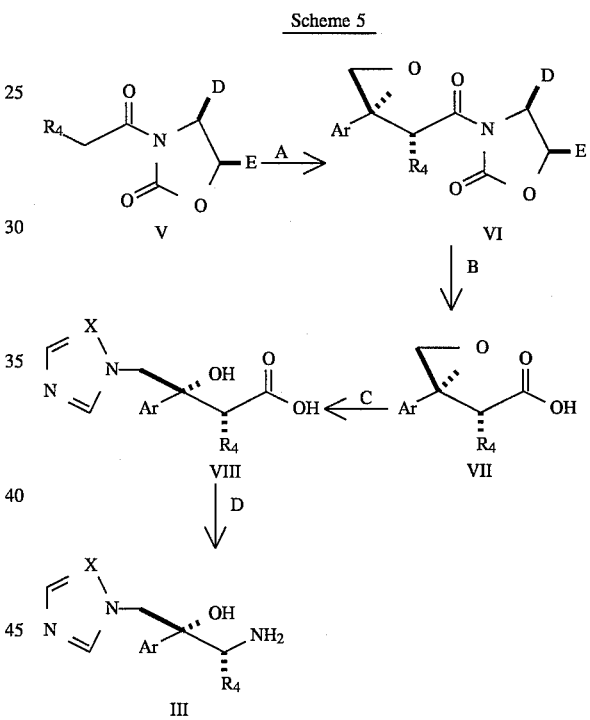

Wherein:

D represents phenyl, benzyl, isopropyl or tert-butyl;

E represents hydrogen, or when D is phenyl, E can also be methyl; and

X, Ar and $R_4$ have the previously defined meaning. According to Scheme 5, the two chiral centers are introduced stereoselectively in one single step (Step A) in an aldol condensation using an (S)-type Evans' oxazolidinone of formula V, i.e. (4S)-4-benzyl-3-propionyl-2-oxazolidinone, (4S)-4-isopropyl-3-propionyl-2-oxazolidinone, (4S)-4-phenyl-3-propionyl-2-oxazolidinone, (4S,5R)-3-propionyl-4-methyl-5-phenyl-2-oxazolidinone or the like, and a haloacetophenone of formula $ArCOCH_2W$, where W is a leaving group such as chloro, bromo, mesyloxy or p-toluenesulfonyloxy, but preferably is a bromine atom, and Ar is as defined above. The enolizing agent can be any commonly used enolizing agent such as lithium diisopropylamide, lithium bis(trimethylsilyl)amide, sodium hydride, sodium bis(trimethylsilyl)amide, or potassium bis(trimethylsilyl)amide, but preferably is sodium bis(trimethylsilyl)amide. The reaction can be performed under a great variety of conditions and reagent proportions. For example, we have found that enolization with sodium bis(trimethylsilyl)amide and condensation with 1.2 equivalents of the acetophenone at −78° C., using tetrahydrofuran as the solvent, gives an acceptable yield of the (2R,3R)-epoxide VI with good stereoselection. The only other epoxide formed during the reaction has an anti relative stereochemistry and, therefore, can be removed by recrystallization at a later stage. The desired compound can be purified by standard methods such as column chromatography, however we have found that the crude reaction mixture can be used in the next step as obtained. In a second step (Step B) the chiral auxiliary is removed under the reported standard conditions for this kind of auxiliaries (LiOH, $H_2O_2$, THF, $H_2O$) (Tetrahedron Lett., 1987, 49, 6141–6144) to give the (2R,3R)-epoxyacid VII and the chiral auxiliary that can be recovered for further use. In a third step (Step C) the (2R,3R)-epoxyacid VII is converted to the (2R,3R)-azoloacid VIII. This reaction is performed using the azole (triazole or imidazole) and a base such as potassium carbonate, sodium hydride or potassium t-butoxide, preferably sodium hydride, in a polar solvent, such as tetrahydrofuran or dimethylformamide, preferably dimethylformamide, at a temperature that can range from room temperature to the boiling point of tetrahydrofuran or to 120° C. if dimethylformamide is used. The (2R,3R)-azoloacid VIII can be purified by recrystallization at this step and, in this way, remove the traces of the anti isomers still present in the mixture. The final step (step D) implies the conversion of the carboxyl group of a compound of formula VIII into an amine, with retention of configuration. We have found that this transformation is succesfully attained under the Curtius conditions, where an acylazide intermediate is rearranged to an isocyanate which is, in turn, internally captured by the hydroxyl of the 3-position to afford an intermediate 2-oxazolidinone, which is directly hydrolized to the amine of formula III. We have found that treating the compound of formula VIII with diphenylphosphorylazide or alternatively, forming first the acid chloride of VIII in a manner being known per se and then treating this with sodium azide, to give an acylazide intermediate, and then heating this acylazide in the presence of a base such as triethylamine in a solvent such as benzene or tert-butanol, preferably the latter, at a temperature between room temperature and that of the boiling point of the solvent, followed by alkaline hydrolysis of the resulting intermediate oxazolidinone under a variety of alkaline conditions (as for example KOH in MeOH:$H_2O$, reflux) affords amine III with an optical yield identical to that reported in the literature (Chem. Pharm. Bull., 1991, 39, 2581–2589). Having the homochiral compound of formula III in hand, the homochiral compounds of formula I are prepared following the general procedure described above.

Optically active compounds of formulae VI, VII and VIII, which are useful as intermediates for the preparation of a compound of formula I, are novel and are also included in the present invention.

According to the activity of the compounds disclosed, the present invention further provides compositions that contain a compound of the present invention, together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, one or more of the active component(s) is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are possible wherein the active ingredient is mixed with water or an oil medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, sodium alginate, polyvinylpirrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods and which comprise one or more active compound(s). The spray compositions will contain a suitable propellent.

Preparations for injection according to the present invention for parenteral administration include sterile aqueous or non-aqueous solutions, suspensions or emulsions, in a nontoxic parentally-acceptable diluent or solvent. Solubility of the compounds can be enhanced by the addition of cyclodextrins, such as hydroxypropyl-β-cyclodextrin. Examples of aqueous solvents or suspending media are distilled water for injection, the Ringer's solution, and isotonic sodium chloride solution. Examples of non-aqueous solvents or suspending media are propylene glycol, polyethylene glycol, dimethylacetamide, polyethylene glycol PEG 400, methyliden, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

Preparations for vaginal administration according to the present invention include tablets, capsules, softgels, moulded pessaries, creams, foams and vaginal douches. Vaginal tablets provide the active component in admixture with lactose, microcrystalline cellulose, pregelatinized starch, polividone and magnesium stearate as typical excipients.

Soft gelatin capsules (softgels) can be made dispersing the active ingredient in an oily medium, for example liquid paraffin, dimethylpolysiloxane 1000 or hydrogenated soybean oil. Moulded pessaries provide the active ingredient in admixture with a suitable synthetic or semisynthetic base (such as Suppocire® or Novata® types). Low viscosity saturated $C_8$ to $C_{12}$ fatty acid glycerides and colloidal silica are also added to improve incorporation and to prevent sedimentation of the active ingredient. Vaginal creams can be prepared as emulsions, with sufficient viscosity to retain their integrity and adhere to the vaginal cavity. Neutral fats, fatty acids, waxes, mineral oils and fatty acid esters can be used as the oily phase. Water, glycerine, sorbitol solution and polyethylene glycol are suitable excipients for the aqueous phase. Non-ionic emulsifying agents like polyethylene glycol ethers may also be used, and such compositions may also contain preserving, buffering and stiffening agents. Foaming systems can be made using a foamer (dispenser) that is able to transform a solution into a foam. Such systems may include cosolvents, buffers, preservatives, foam stabilizers and perfumes in an aqueous vehicle. Vaginal douches may contain cosolvents, preservatives, buffers and perfuming agents in a surfactant rich aqueous solution.

A compound of the invention may also administered in the form of suppositories for rectal administration of the drug, or as creams, ointments, pastes, lotions, gels, sprays, foams, aerosols, solutions, suspensions or powders for topical use. Such compositions are prepared following conventional procedures well known to those skilled in the art.

A compound of the invention may also be administered as a hair or body shampoo. These formulations may be prepared using suitable ionic and/or amphoteric surface-active agents such as sodium laureth sulfate, triethanolamine laureth sulfate, cocoamidopropyl betaine; thickening agents for example cocamide DEA, carbomer, sodium chloride and polyethylene glycol 6000 distearate; and optionally, emolient and superfatting agents, buffers, and preserving and perfuming agents.

The dosage and frequency of dose may vary depending upon the nature of the fungal disease, symptoms, age and body weight of the patient, as well as upon the route of administration. Thus, for oral and parenteral administration to human patients the daily dose will be from 1 to 1000 mg for an adult, preferably a dosage of from 5 to 500 mg, which may be administered either as a single dose or as divided doses. For topical administration, a cream or ointment containing 1–10% of a compound of formula I will be applied to the skin from one to three times daily.

Following are some representative preparations for tablets, capsules, aerosols and injectables. They can be prepared following standard procedures and they are useful in the treatment of fungal diseases.

| Tablets | | |
|---|---|---|
| Compound of formula I | 100 | mg |
| Dibasic calcium phosphate | 125 | mg |
| Sodium starch glycolate | 10 | mg |
| Talc | 12.5 | mg |
| Magnesium | 2.5 | mg |
| | 250.0 | mg |
| Hard gelatin capsules | | |
| Compound of formula I | 100 | mg |
| Lactose | 197 | mg |

| -continued | | |
|---|---|---|
| Magnesium stearate | 3 | mg |
| | 300 | mg |
| Aerosol | | |
| Compound of formula I | 4 | g |
| Flavouring agent | 0.2 | g |
| Propylene glycol to | 100 | ml |
| Suitable propellent to | 1 | unit |
| Injectable preparation | | |
| Compound of formula I | 100 | mg |
| Benzylic alcohol | 0.05 | ml |
| Propylene glycol | 1 | ml |
| Water to | 5 | ml |

The following examples illustrate, but do not limit, the scope of the present invention:

REFERENCE EXAMPLE 1

(4R *,5R *)-2-Benzyloxymethyl-4-methyl-5-[(1-H-1,2,4-triazol-1-1-yl)methyl]-5-(2,4-difluorophenyl) oxazolidine

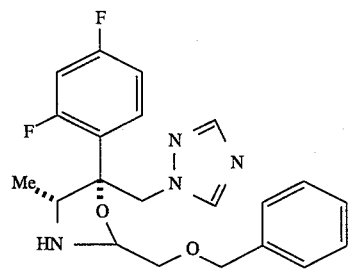

A solution containing (2R*,3R*)-3-amino-1-(1H-1,2,4-triazol-1-yl)-2-(2,4-difluorophenyl)-2-butanol (3.87 g, 14.42 mmol) (obtained according to patent EP 332387) and benzyloxyacetaldehyde (2.17 g, 14.42 mmol) (obtained by $NaIO_4$ cleavage of DL-3-benzyloxy-1,2-propanediol) in benzene (40 mL) was heated at reflux for 4 h. The mixture was concentrated to afford the desired product (6.01 g) as an oil. This product was directly used in the next step without further purification.

REFERENCE EXAMPLE 2

(2R*,3R*)-3-[(2-Benzyloxyethyl)amino]-2-[2,4-difluorophenyl]-1-(1H-1,2,4-triazol-1-yl)-2-butanol

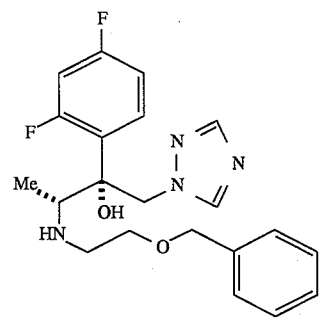

To a cooled solution (0° C.) of the oxazolidine obtained in reference example 1 (6 g) in THF (40 mL) was added lithium aluminum hydride (LAH, 547 mg, 14 mmol) and the mixture was stirred at 0° C. for 3 h and then at room temperature for 1 h. The resulting mixture was cooled to 0° C. and 0.5 mL of water, 0.5 mL of a 15% NaOH solution, and 1.5 mL of water was successively added. The suspension was stirred for 0.5 h and filtered through celite. The filtrate was concentrated to afford a residue that was purified by flash chromatography (EtOAc), to yield the pure product as a colourless oil (4.45 g, yield:80% from the amine).

$^1$H NMR (80 MHz, CDCl$_3$) δ (TMS): 7.90 (s, 1H, triazole), 7.73 (s, 1H, triazole), 7.5-7.1 (m, 1H, arom), 7.33 (s, 5H, benzyl), 6.9-6.5 (m, 2H, arom), 4.77 (AB quartet, Δv=0.074, 2H, Tr-CH$_2$), 4.53 (s, 2H, CH$_2$Ph), 3.7-3.4 (m, 2H), 3.3-2.5 (m 3H), 0.90 (dd, J=1.2 Hz, J=7 Hz, 3H, CHMe).

REFERENCE EXAMPLE 3

(4R *,5 R *)-2-Benzyloxymethyl-4-methyl-5-[(1H-1,2,4-triazol-1-yl )methyl]-5-)2,4-dichlorophenyl) oxazolidine

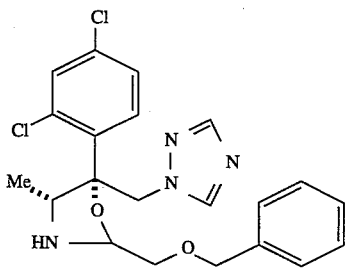

Following the procedure described in reference example 1, but using (2R*,3 R*)-3-amino-1-(1H-1,2,4-triazol-1-yl)-2-(2,4-dichlorophenyl)-2-butanol (prepared as described in patent EP 332387) instead of its difluoro analogue, the title compound was obtained in a similar yield and it was used in the next step without further purification.

REFERENCE EXAMPLE 4

(2R*,3R*)-3-[(2-Benzyloxyethyl)amino]-2-[2,4-dichlorophenyl] -1-(1H-1,2,4 -triazol-1-yl)-2-butanol

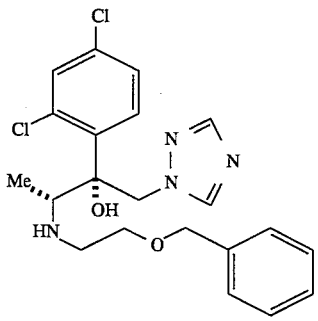

Following the procedure described in reference example 2, but reducing the compound obtained in reference example 3, the title compound was obtained as a white solid in 79% yield.

mp: 105°–107° C.;

$^1$H NMR (80 MHz, CDCl$_3$) δ (TMS): 7.82 (s, 1H, triazole), 7.68 (s, 1H, triazole), 7.49 (d, J=8.6 Hz, 1H, arom), 7.33 (s, 5H, benzyl), 7.10 (dt, Jd=2 Hz, Jt=12.8 Hz, 2H, arom), 5.22 (d, J=14.2 Hz, 1H, CH(H)), 4.71 (d, J=14.2 Hz, 1H, CH(H)), 4.55 (s, 2H, CH$_2$Ph), 3.9-3.5 (m, 3H), 3.4-2.6 (m, 2H), 0.80 (d, J=7 Hz, 3H, CHMe).

Analysis Calcd. for C$_{21}$H$_{24}$C$_{12}$N$_3$O$_2$: C 57.94; H 5.56; N 12.87. Found: C 58.29; H 5.74; N 12.53.

REFERENCE EXAMPLE 5

(2R*,3R*)-3-[N-(Cyanomethyl)amino]-2-[2,4-difluorophenyl]-1-(1H-1,2,4 -triazo 1-1-yl)-2-butanol

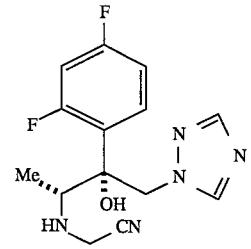

To a mixture of methanol (130 mL), water (65 mL) and pH 7 phosphate buffer (65 mL) it was added (2R*,3R*)-3-amino-1-(1H-1,2,4-triazol-1-yl)-2-(2,4 -difluorophenyl)-2-butanol (400 mg, 14.9 mmol) (prepared as described in patent EP 332387, p-formaldehyde (490 mg, 16.4 mmol) and potassium cyanide (1.94 g, 29.82 mmol). The resulting mixture was stirred at room temperature for 48 h. The mixture was concentrated to afford the desired product as an oil that was purified by flash chromatography, to give a white solid in 78% yield.

mp: 138°–139° C.;

$^1$H NMR (80 MHz, CDCl$_3$) δ (TMS): 7.79 (s, 2H, triazole), 7.5-7.2 (m, 1H, arom), 6.9-6.6 (m, 2H, arom), 4.88 (s, 2H, Tr-CH$_2$), 3.71 (s, 2H, CH$_2$CN), 3.5-3.1 (m, 1Hm, CHMe), 0.96 (d, J=7 Hz, 3H, CHMe).

Analysis Calcd. for C$_{14}$H$_{15}$F$_2$N$_5$O: C 54.72; H 4.92; N 22.79. Found: C 54.70; H 4.86; N 22.79.

REFERENCE EXAMPLE 6

(2R *,3R *)-3-[N-(2-Aminoethyl)amino]-2-[2,4-difluorophenyl]-1-(1H-1,2,4-triazol-1-yl)-2-butanol

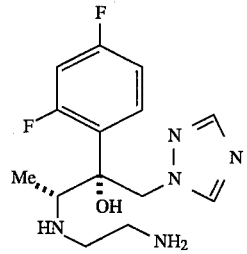

To a cooled (0° C.) solution of the product obtained in reference example (4.12 g, 13.4 mmol) in anhydrous THF (50 mL) was added lithium aluminum hydride (509 mg, 13.4 mmol). The mixture was stirred for 2 h at 0° C. and then water was slowly added, followed by 15% NaOH solution. The resulting suspension was stirred for some minutes and then filtered through celite. The filtrate was dried over anhydrous $Na_2SO_4$, filtered and concentrated to afford the title compound as an oil in 69% yield.

$^1$H NMR (80 MHz, $CDCl_3$) δ (TMS): 7.94 (s, 1H, triazole), 7.74 (s, 1H, triazole), 7.5-7.2 (m, 1H, arom), 6.9-6.6 (m, 2H, arom), 4.82 (dq AB, 2H, Tr-$CH_2$), 3.2- 2.5 (m, 5H), 0.92 (dd, J=1.2 Hz, J=7 Hz, 3H, CHMe).

REFERENCE EXAMPLE 7

(2R*,3R*)-3-[N-(2-Tert-butoxycarbonylaminoethyl)amino]-2-[2,4-difluoro-phenyl]-1-(1H-1,2,4-triazol-1-yl)-2-butanol

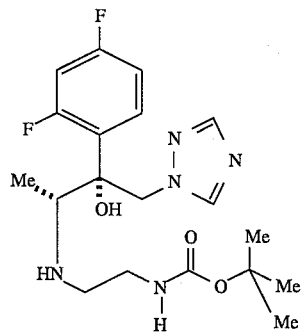

To a solution of the product obtained in reference example 6 (2.5 g, 8.03 mmol) in water (16 mL), dioxane (32 mL) and 1N NaOH (8 mL) was added $BOC_2O$ (1.75 g, 8.03 mmol). The mixture was stirred for 2 days at room temperature and finally evaporated to dryness. The residue was partitioned between water and EtOAc. The organic phase was dried over $Na_2SO_4$, filtered and the solvent was removed to afford an oil that was purified by flash chromatography (1.25 g, 37%).

$^1$H NMR (80 MHz, $CDCl_3$) δ (TMS): 7.93 (s, 1H, triazole), 7.75 (s, 1H, triazole), 7.5-7.2 (m, 1H, arom), 6.9-6.6 (m, 2H, arom), 4.83 (AB quartet, Δv=0.148, J= 14.4 Hz, 2H, Tr-$CH_2$), 3.4-2.5 (m, 5H), 1.45 (s, 9H, $CMe_3$), 0.89 (d, J=7 Hz, 3H,Me).

REFERENCE EXAMPLE 8

(2R*,3R*)-N-[3-(2,4-diflurophenyl)-3-hydroxy-4-(1H-1,2,4-triazol- 1-yl)-2-butyl]glycine, benzyl ester

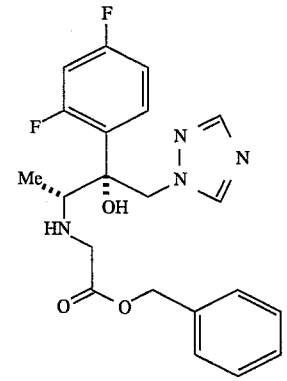

A solution containing (2R*,3R*)-3-amino-2-(2,4-difluorophenyl)-1-(1 H-1,2,4-triazol-1-yl)-2-butanol (14.9 g, 55.8 mmol) (prepared as described in patent EP 332387) in dry THF (225 mL) was-treated at room temperature with benzylbromoacetate (19.2 g, 13.2 mL, 83.7 mmol, 1.5 eq) and triethylamine (15.5 mL, 111 mmol, 2 eq) for 20 h which resulted in the appearance of a white precipitate. The mixture was concentrated and partitioned between $CHCl_3$ and 5% aqueous $NaHCO_3$. The aqueous phase was discarded and the organic phase was sequentially washed with more 5% aqueous $NaHCO_3$ and brine, dried over anhydrous $Na_2SO_4$, filtrated and the filtrate was concentrated to an oil (29 g) which was purified by flash-chromatography to afford the title product as a colorless oil (22.2 g, 95%).

$^1$H NMR (80 MHz, $CDCl_3$) δ (TMS): 7.85 (s, 1H, triazole), 7.74 (s, 1H, triazole), 7.6-7.2 (m, 1H, arom), 7.37 (s, 5H, benzyl), 6.9-6.6 (m, 2H, arom), 5.19 (s, 2H, $CH_2Ph$), 4.83 (AB q, Δv=0.023, J=14.2 Hz, 2H, Tr-$CH_2$), 3.56 (s, 2H, $CH_2CO$), 3.3-3.0 (m, 1H, CHMe), 0.90 (d, J=6.2 Hz, 3H, CHMe).

REFERENCE EXAMPLE 9

(2R *,3R*)-N-[3-(2,4-Dichlorophenyl)-3-hydroxy-4-(1H-1,2,4-triazol-1-yl)-2 -butyl]glycine, ethyl ester

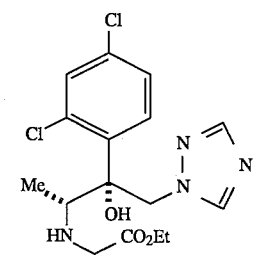

Following the procedure described in reference example 8, but starting from (2R*,3R*)-3-amino-1-( 1H-1,2,4-triazol-1-yl)-2-(2,4-dichlorophenyl)-2 -butanol (obtained according to patent EP 332387) and using ethyl bromoacetate instead of benzyl bromoacetate, the title compound was obtained in a similar yield.

¹H NMR (80 MHz, CDCl₃) δ (TMS): 7.88 (s, 1H, triazole), 7.73 (s, 1H, triazole), 7.52 (d, J= 8.6Hz, 1H, arom), 7.30 (d, J= 2.1Hz, 1H, arom), 7.08 (dd, J= 8.6Hz, J= 2.1 Hz, 1H, arom), 5.13 (AB quartet, Δv=0.470, J=14.4 Hz, 2H, Tr—CH₂), 4.23 (q, J= 7.1Hz, 2H, OCH? CH3), 3.74 (m, 1H, CHMe), 3.55 (s, 2H, CH₂CO), 1.31 (t, J= 7.1Hz, 3H, OCH₂CH3), 0. 84 (d, J=6.6 Hz, 3H, CHMe).

REFERENCE EXAMPLE 10

(2R*,3R*)-N-[3-(2,4-Dichlorophenyl)-3-hydroxy-4-(1H-1,2,4-triazol-1-yl)-2-butyl]glycine, benzyl ester

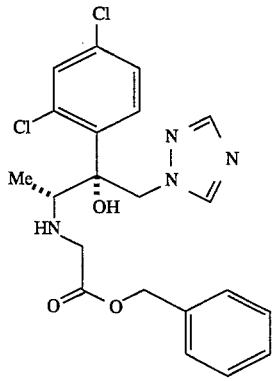

Following the procedure described in reference example 8, but using (2R*,3 R*)-3-amino-1-(1H-1,2,4-triazol-1-yl)-2-(2,4-dichlorophenyl)-2-butanol (prepared as described in patent EP 332387) instead of its difluoro analogue, the title compound was obtained in a similar yield.

¹H NMR (80 MHz, CDCl₃) δ (TMS): 7.79 (s, 1H, triazole), 7.71 (s, 1H, triazole), 7.49 (d, J=8.6Hz, 1H, arom), 7.37 (s, 5H, phenyl), 7.27 (d, J= 2.1Hz, 1H, arom), 7.06 (dd, J=8.6Hz, J=2.1 Hz, 1H, arom), 5.20 (s, 2H, CH₂Ph), 5.07 (AB quartet, Δv=0.410, J=14.4 Hz, 2H, Tr—CH₂), 3.70 (q, J=6.5Hz, 1H, CHMe), 3.60 (s, 2H, CH₂CO), 0.80 (d, J=6.5 Hz, 3H, CHMe).

REFERENCE EXAMPLE 11

1-[4-(Trifluoromethyl)phenyl]-1-propanol

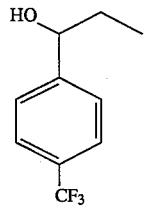

Dry tetrahydrofuran (700 mL), magnesium turnings (16.75 g, 0.69 mol, 1.2 eq), and a iodine crystal were placed in a flask and the mixture was stirred intensively at 0° C. Bromoethane (68 g, 46.7 mL, 0.69 mol, 1.1 eq) was added dropwise and the resulting mixture was allowed to stir for 30 min. Then the reaction mixture was treated with 4-trifluoromethylbenzaldehyde (100 g, 0.57 mol, 1 eq). After stirring at room temperature for 2 h, the reaction mixture was cooled to 0° C. and poured carefully to a mixture of 1N HCl (750 mL) and ice cooled to 0° C. and poured carefully to a mixture of 1N HCl (750 mL) and ice with CH₂Cl₂. The organic layer was washed with 5% aqueous NaHCO₃ and with CH₂Cl₂. The organic layer was washed with 5% aqueous NaHCO₃ and brine, then dried over anhydrous Na₂SO₄, the drying agent was filtered and ¹H NMR (80 MHz, CDCl₃) δ (TMS): 7.52 (q, J=5.7 Hz, 4H, arom), 4.8-4.5 (m, 1H, CHOH), 1.73 (q, J=6.8 Hz, 2H, CH₂), 0.92 (t, J=6.8 Hz, 3H, Me).

REFERENCE EXAMPLE 12

4-Trifluoromethylpropiophenone

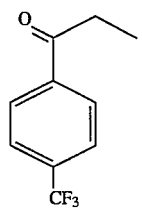

A solution of the compound obtained in reference example 11 (23 g, 0.11 mol) in CH₂Cl₂ (60 mL) was added dropwise to a suspension of PCC (36.6 g, 0.17 mol, 1.5 eq) and celite (35 g) in CH₂Cl₂ (260 mL) at room temperature. The mixture was stirred for 1 h and then diethyl ether (500 mL) was added. The resulting mixture was filtered through celite, washed with aqueous NaOH solution, dried and concentrated to a dark brown oil (20.7 g, 95% mass balance) that was used in the next step without further purification.

¹H NMR (80 MHz, CDCl₃) δ (TMS): 8.05 (d, J=8.2 Hz, 2H, arom), 7.71 (d, J=8.2 Hz, 2H, arom), 3.04 (q, J=7.1 Hz, 2H, CH₂), 1.24 (t, J=7.1 Hz, 3H, Me).

REFERENCE EXAMPLE 13

α-Bromo-4-trifluoromethylpropiophenone

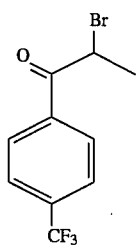

To a solution of the compound obtained in reference example 12 (37 g, 0.18 mol) in acetic acid (600 mL) was added dropwise a solution of 5% bromine in acetic acid (190 mL) at room temperature. When the addition was complete, the reaction mixture was stirred at 40° C. for 2.5 h. Then, acetic acid was distilled off and the residue was diluted with EtOAc (300 mL) and washed with a 10% aqueous NaHCO₃ solution. The organic phase was dried over MgSO₄ and the solvent was removed to afford the title compound as an oil (46.9 g, 93% mass balance).

¹H NMR (80 MHz, CDCl₃) δ (TMS): 8.13 (d, J=8.2Hz, 2H, arom), 7.74 (d, J=8.2 Hz, 2H, arom), 5.26 (q, J=6.6 Hz, 1H, CHBr), 1.92 (d, J=6.6 Hz, 3H, Me).

REFERENCE EXAMPLE 14

α-Hydroxy-4-trifluoromethylpropiophenone

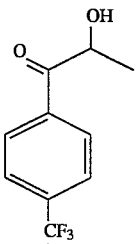

To a solution of the compound obtained in reference example 13 (45.9 g, 0.16 mol) in a 4:1 mixture of DMF and H$_2$O (460 mL) was added LiOH.H$_2$O (6.9 g, 0.16 mol, 1 eq) at 0° C. and the resulting mixture was stirred for 2 h. After diluting with EtOAc, the mixture was washed with saturated aqueous NaCl solution, dried over anhydrous Na$_2$SO$_4$, the drying agent filtered and the filtrate concentrated in vacuo to afford 39.81 g of a yellowish oil. Purification by chromatography on silica gel (EtOAc:Hex mixtures of increasing polarity) yielded 23.46 g of the title compound.

$^1$H NMR (80 MHz, CDCl$_3$) δ (TMS): 8.05 (d, J=8.2Hz, 2H, arom), 7.74 (d, J=8.2 Hz, 2H, arom), 5.2 (Br q, 1H, CH), 1.45 (d, J=7Hz, 3H, Me).

REFERENCE EXAMPLE 15

α-(Tetrahydropyran-2-yloxy)-4-trifluoromethylpropiophenone

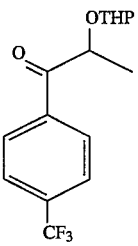

A mixture containing the compound obtained in reference example 14 (23.46 g, 0.11 mol), 3,4-dihydro-2H-pyran (12.6 mL, 0.14 mol, 1.27 eq), pyridinium p-toluenesulfonate (0.006 mol) and CH$_2$Cl$_2$ (260 mL) was stirred at room temperature for 24 h. The reaction was quenched by the addition of 10% aqueous NaHCO$_3$ solution and the layers were separated. The organic layer was washed with saturated NaCl solution, dried over anhydrous Na$_2$SO$_4$, the drying agent was filtered and the filtrate was concentrated to afford a crude oil (28.6 g) that was used in the next step without further purification.

$^1$H NMR (80 MHz, CDCl$_3$) δ (TMS): 8.2-7.9 (m, 2H, arom), 7.71 (d, J=8.2 Hz, 2H, arom), 5.3-4.5 (m, 2H), 4.2-3.3 (m, 2H), 2.0-1.3 (m, 9H).

REFERENCE EXAMPLE 16

2-[2-(Tetrahydropyran-2-yloxy)ethyl]-2-[4-(trifluoromethyl)phenyl]oxirane

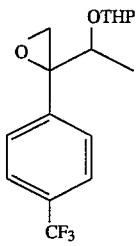

A suspension of 55% NaH (2.7 g, 0.11 mol, 1.2 eq) was added to anhydrous DMSO (300 mL) and the mixture was heated at 60° C. for 1.5 h. The reaction mixture was allowed to cool to room temperature and trimethylsulfoxonium iodide (41.6 g, 0.19 mol, 2 eq) was added. The reaction mixture was stirred at this temperature for 1 h. Next, the compound obtained in reference example 15 (28.6 g, 0.09 mol) in DMSO (200 mL) was added dropwise. After stirring for 2 h, the mixture was partitioned between benzene and water. The organic layer was separated, dried over anydrous Na$_2$SO$_4$, the drying agent was filtered, and the filtrate was concentrated in vacuo to afford a brown oil (29.7 g) that was directely used in the next step as such.

$^1$H NMR (80 MHz, CDCl$_3$) δ (TMS): 8.60 (s, 4H, arom), 5.4-4.6 (m, 1H, OCHO), 4.4-3.2 (m, 3H), 3.1 (m, 1H, epoxide), 2.7 (m, 1H, epoxide), 1.8-1.4 (m, 6H), 1.4-1.0 (m, 3H, Me).

REFERENCE EXAMPLE 17

(2R*,3R*)-1-(1H-1,2,4-Triazol-1-yl)-2-[4-(trifluoromethyl)phenyl]-2,3-butane-diol

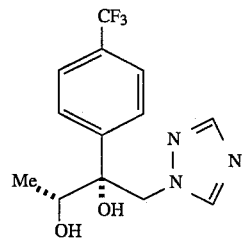

The crude product obtained in reference example 16 (29.7 g) was dissolved in DMF (300 mL) and then treated with 1,2,4-triazole (26.0 g, 0.37 mol) and potassium tert-butoxide (21.12 g, 0.19 mol) at 100° C. for 1 h. DMF was distilled off and the residue was partitioned between benzene and water. The organic phase was separated, washed with saturated NaCl solution, dried over anhydrous Na$_2$SO$_4$, filtered and the filtrate concentrated to afford a brown oil (36.28 g). This product was then dissolved in methanol (300 mL) and treated with p-toluenesulfonic acid (17.9 g, 0.094 mol) at room temperature for 2 h. 10% NaHCO$_3$ solution was added and methanol was evaporated. The aqueous residue was extracted with EtOAc, dried and concentrated to afford a brown solid. Recrystallization from EtOAc yielded the pure (2R*,3R*) stereoisomer as a white solid (8.41 g, 25% from ref. example 14).

mp: 177°–178° C.;

$^1$H NMR (80 MHz, MeOH-d$_4$+CDCl$_3$) δ (TMS): 7.98 (s, 1H, CH triazole), 7.73 (s, 1H, CH triazole), 7.6-7.3 (m, 4H, arom), 4.72 (s, 2H, CH$_2$), 4.16 (q, J=7.0Hz, 1H CHMe), 0.96 (d, J=7Hz, 3H, CHMe).

Analysis Calcd. for C$_{13}$H$_{14}$F$_3$N$_3$O$_2$: C 51.83 H 4.68; N 13.95. Found: C 51.96; H 4.63; N 13.61.

REFERENCE EXAMPLE 18

(2R*,3R*)-3-Methanesulfonyloxy-2-[4-(trifluoromethyl)phenyl]-1-(1-H-1,2,4-triazol-1-yl)-2-butanol

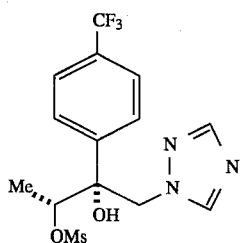

To a cooled solution (0° C.) of the compound obtained in reference example 17 (32 g, 106 mmol) in pyridine (500 mL) was added methanesulfonyl chloride (19.5 g, 13.2 mL, 170 mmol, 1.6 eq) and the reaction mixture was stirred at room temperature for 2 h. Next, pyridine was distilled off and the residue was partitioned between CH$_2$Cl$_2$ and 10% aqueous NaHCO$_3$ solution. The organic phase was separated, dried over anhydrous Na$_2$SO$_4$, the drying agent was filtered and the filtrate was concentrated to afford the desired product (38.39 g, 95% mass balance), pure by TLC analysis, which was used in the next step as obtained.

$^1$H NMR (80 MHz, MeOH-d$_4$+CDCl$_3$) δ (TMS): 8.00 (s, 1H, CH triazole), 7.72 (s, 1H, CH triazole), 7.54 (s, 4H, arom), 5.16 (q, J=7Hz, 1H, CHMe), 4.77 (s, 2H, CH$_2$), 3.16 (s, 3H, MeSO$_2$), 1.24 (d, J=7Hz, 3H, CHMe).

REFERENCE EXAMPLE 19

(2R*,3R*)-3-Azido-1-(1-H-1,2,4-triazol-1-yl)-2-[4-(trifluoromethyl)phenyl]-2-butanol

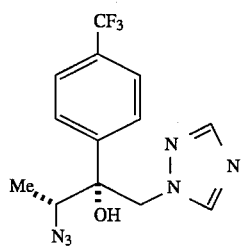

A solution of the compound obtained in reference example 18 (38.39 g, 101 mmol), sodium azide (34.24 g, 527mmol, 5.2 eq) and ammonium chloride (5.4 g, 101 mol, 1 eq) in DMF (500 mL) was heated at 115° C. for 15 h. DMF was distilled off, and the residue was partitioned between water (0.5 L) and benzene (0.5 L). The organic layer was washed with saturated aqueous NaCl solution, dried over anhydrous Na$_2$SO$_4$, the drying agent was filtered and the filtrate was concentrated to afford the title compound of the example as a yellowish oil (37.44 g, 113% mass balance), pure by TLC analysis. An analytical sample was obtained by recrystallization from EtOAc: Hex as a white solid.

mp: 91°–94° C.;

$^1$H RMN (80 MHz, MeOH-d$_4$+CDCl$_3$) δ (TMS): 7.82 (s, 1H, CH triazole), 7.71 (s, 1H, CH triazole), 7.47 (AB q, Δv=0.16, J=8.4Hz, 4H, arom), 5.16 (AB quartet, Δv=0.20, J=14.2Hz, 2H, TrCH$_2$), 3.70 (q, J=6.7Hz, 1H, CHMe), 1.15 (d, J=6.7Hz, CHMe).

Analysis Calcd. for C$_{13}$H$_{13}$F$_3$N$_6$O: C 47.86; H 4.02; N 25.76. Found: C 47.12; H 3.76; N 22.68.

REFERENCE EXAMPLE 20

(2R*,3 R*)-3-Amino-1-(1-H-1,2,4-triazol-1-yl)-2-[4-(trifluoromethyl)phenyl]-2-butanol

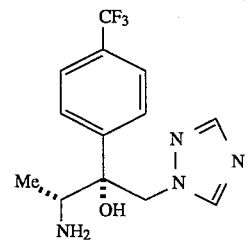

A suspension of the compound obtained in reference example 19 (37.44 g) and 10% Pd/C (7 g) in ethanol (1 L) was hydrogenated (H$_2$, 1 atm) at room temperature for 1 h with intensive stirring. The resulting mixture was filtered through celite and concentrated to afford the corresponding amine as a pale solid (26.97 g, 85% from the diol). An analytical sample was obtained as a white powder by flash-chromatography (CHCl$_3$: MeOH 9:1) and recrystallization from EtOAc: hexane.

mp: 114°–117° C.;

$^1$H NMR (80 MHz, MeOH-d$_4$+CDCl$_3$) δ (TMS): 7.88 (s, 1H, CH triazole), 7.86 (s, 1H, CH triazole), 7.47 (AB quartet, Δv=0,175, J=8.5 Hz, 4H, arom), 4.53 (s, 2H, CH$_2$), 3.38 (q, J=7Hz, 1H, CHMe), 0.85 (d, J=7Hz, 3H, CHMe).

Analysis Calcd. for C$_{13}$H$_{15}$F$_3$N$_4$O: C 51.98; H 5.04; N 18.66. Found: C 51.92; H 5.06; N 18.62.

REFERENCE EXAMPLE 21

(2R*,3R*)-N-[3-(4-Trifluoromethylphenyl)-3-hydroxy-4-(1H-1,2,4-triazol-1-yl)- 2-butyl]glycine, benzyl ester

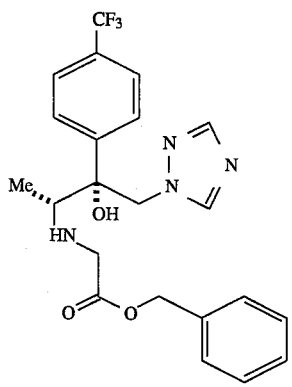

Following the procedure described in reference example 8, but starting from the compound obtained in reference example 20, the title compound was obtained in 90% yield.

$^1$H NMR (80 MHz, CDCl$_3$) δ (TMS): 7.91 (s, 1H, triazole), 7.80 (s, 1H, triazole), 7.6-7.2 (m, 4H, arom), 7.37 (s, 5H, benzyl), 5.29 (s, 2H, CH$_2$Ph), 4.73 (AB quartet, Δv=0.308, J=14.3 Hz, 2H, Tr—CH$_2$), 3.51 (AB quartet, Δv=0.090, J=17.8Hz, 2H, CH$_2$CO), 2.82 (q, J=6.6Hz, 1H, CHMe), 0.96 (d, J=6.6 Hz, 3H, CHMe).

REFERENCE EXAMPLE 22

(2R,3R)-N-[3-(2,4-Difluorophenyl)-3-hydroxy-4-(1H-1,2,4-triazol-1-yl)-2-butyl]glycine, benzyl ester

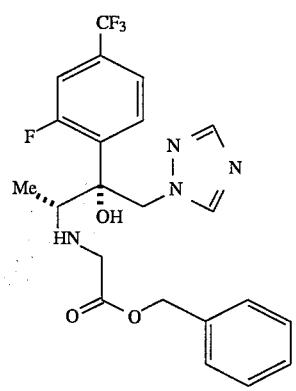

Following the procedure described in reference example 8, but using (2R,3R)-3-amino-2-(2,4-difluorophenyl)-1-(1H-1,2,4-triazol-1-yl)-2-butanol (prepared as described in EP 332387) the title compound was prepared as an oil. The NMR spectrum of the compound thus prepared was identical to that of the compound obtained in reference example 8.

REFERENCE EXAMPLE 23

(2R,3R)-N-[3-(2,4-Dichlorophenyl)-3-hydroxy-4-(1H-1,2,4-triazol-1-yl)-2 -butyl]glycine, benzyl ester

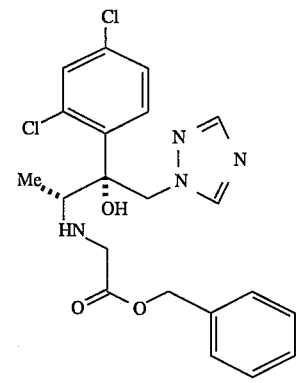

Following the procedure described in reference example 10 but using (2R,3R)-3-amino-2-(2,4-dichlorophenyl)-1-(1H-1,2,4-triazol-1-yl)-2-butanol (pre-pared as described in EP 332387) the title compound was obtained as an oil. The NMR spectrum of the compound thus prepared was identical to that of the compound obtained in reference example 10.

[α]$_D$-94.4° (c=1, MeOH)

REFERENCE EXAMPLE 24

(2R*,3R*)-N-[3-(2,4-Difluorophenyl)-3-hydroxy-4-(1H-1,2,4-triazol-1-yl)-2 -butyl]-DL-alanine, benzyl ester

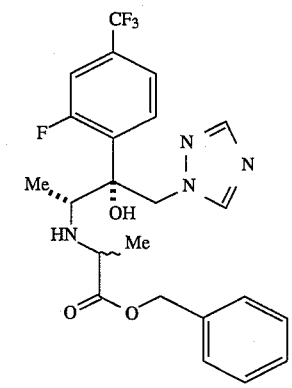

Following the procedure described in reference example 10 but using benzyl 2-bromopropionate instead of benzylbromoacetate and increasing the reaction time to 7 days of stirring at room temperature, the title compound was obtained in 54% yield as an oil as a 1:1 mixture of diastereomers.

$^1$H NMR (80 MHz, CDCl$_3$) δ (TMS): 7.81 (s, 1H, triazole), 7.74 (s, 1H, triazole), 7.5-7.2 (m, 1H, arom), 7.36 (s, 5H, benzyl), 6.9-6.6 (m, 2H, arom), 5.18 (s, 2H, CH$_2$Ph), 5.1-4.5 (m, 4H,) 3.7-3.3 (m, 1H, CHMe), 1.35 (dd, JC-F= 2Hz, J= 7Hz, 3/2H, CHMe), 0.85 (dd, JC-F=2Hz, J=7Hz, 3/2H, CHMe).

REFERENCE EXAMPLE 25

(4R*,5R*)-2-Chloromethyl-4-methyl-5-[(1-H-1,2,4-triazol-1-yl)methyl]-5-(2,4-dichlorophenyl) oxazolidine

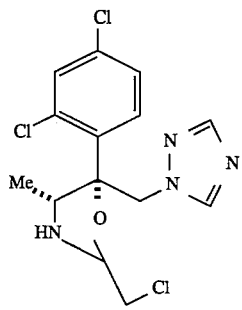

Following the procedure described in reference example 1, but using a 45% aqueous solution of chloroacetaldehyde and (2R*,3R*)-3-amino-1-(1 H-1,2,4-triazol-1-yl)-2-(2,4-dichlorophenyl)-2-butanol, the title compound was obtained as a solid in 63% yield after flash-chromatography purification (EtOAc).

mp: 119°–125° C.;

$^1$H NMR (80 MHz, CDCl$_3$) δ (TMS): 8.32(s, 1H, triazole), 7.68 (s, 1H, triazole), 7.4-7.0 (m, 3H, arom), 5.60 (d, J=14Hz, 1H, CH(H)), 5.12 (t, J=2Hz, 1H, CHO), 4.6 (d, J=14Hz, 1H, CH(H)), 4.39 (q, J=7Hz, 1H, CHMe), 3.96 (d, J=2Hz, 1H, CH(H)Cl), 3,92 (d, J=2Hz, 1H, CH(H)Cl), 1.00 (d, J=7Hz, 3H, Me).

Anal. Calcd. for $C_{14}H_{15}Cl_3N_4O$: C 46.50; H 4.18; N 15.49. Found: C 46.32; H 3.88; N 15.81.

REFERENCE EXAMPLE 26

(4R*,5R*)-2,5-bis-[(1-H-1,2,4-Triazol-1-yl)methyl]-4-methyl-5-(2,4-dichlorophenyl) oxazolidine

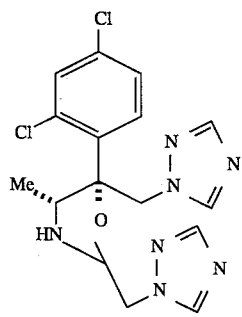

A solution containing the product obtained in reference example 25 (750 mg, 2 mmol), 1,2,4-triazole (0,286 g, 4.1 mmol, 2 eq), and K$_2$CO$_3$ (0.572 g, 4.1 mmol, 2 eq) in DMF (40 mL) was stirred at 90° C. during 5 h. The solvent was removed under reduced pressure and the residue was partitioned between CHCl$_3$ and a 5% NaHCO$_3$ aqueous solution. The organic phase was separated, dried over MgSO$_4$, concentrated and purified by flash-chromatography to afford the title product as a mixture of diastereomers at the acetal carbon (0.69 g, 87%).

$^1$H NMR (80 MHz, CDCl$_3$) δ (TMS): 8.33 (s, 1H, triazole), 8.19 (s, 1H, triazole), 8.01 (s, 1H, triazole), 7.95 (s, 1H, triazole), 7.81 (s, 1H, triazole), 7.74 (s, 1H, triazole), 7.71 (s, 1H, triazole), 7.5-7.0 (m, 3H, arom), 5.13 (complex t, 1H, CHO), 5.0-4.7 (m, 2H), 4.5-4.1 (m, 4H), 0.95 and 0.84 (d, J=7Hz, 3H, Me).

REFERENCE EXAMPLE 27

(2R*,3R*)-3-[(2-(1H-1,2,4-Triazol-1-yl)ethyl)amino]-2-(2,4-dichloro(1H-1,2,4-triazol-1-yl)-2-butanol

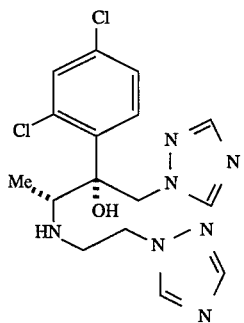

Following the procedure described in reference example 2 but reducing the product obtained in reference example 26, the title product was obtained as a yellowish oil that was used in the next step without further purification.

REFERENCE EXAMPLE 28

(3(2R,3R),4S)-3-[3-(2,4-Difluorophenyl)-3,4-epoxy-2-methyl-1-oxobutyl]-4-benzyl-2-oxazolidinone

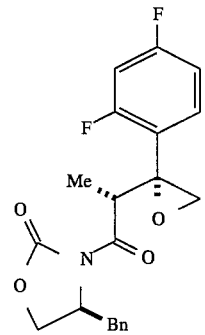

To a cooled (–78° C.) solution containing sodium bis(trimethylsilyl)amide (394 mg, 2.15 mmol, 1 eq) in dry THF (8 mL) was added a solution of (4S)-3-propionyl-4-benzyl-2-oxazolidinone (500 mg, 2.15 mmol) (prepared from propionyl chloride and (4S)-4-benzyl-2-oxazolidinone, which, in turn, was purchased in Kg quantities to Urquima S. A., Sant Fost de Capcentelles, Barcelona, Spain) in dry THF (2 mL) and the mixture was stirred at this temperature for 1.5 h. Then, a solution of α-bromo-2,4-difluoroacetophenone (606 mg, 2.6 mmol, 1.2 eq) in THF (2 mL) was slowly added and the mixture was stirred at –78° C. during 2 h. The reaction was quenched by the addition of a saturated NH$_4$Cl aqueous solution and the volatiles were removed in vacuo.

The aqueous residue was then partitioned between $CH_2Cl_2$ and water. The aqueous phase was discarded and the organic phase was washed with 5% aqueous $NaHCO_3$ and brine, then dried over anhydrous $Na_2SO_4$, the drying agent was filtered and the filtrate was concentrated to a cream-colored oil (1.2 g). RMN analysis of the crude product indicated formation of a main epoxide (i.e. the title compound) and a minor isomer which was proved to have an anti relative stereochemistry. An analytical sample of the diastereomerically pure title product was obtained by silica gel chromatography (EtOAc:Hex 1:5) of an aliquot of 120 mg of crude reaction mixture as a colorless, thick oil (47 mg, 57%).

$^1$H RMN (80 MHz, $CDCl_3$) 15 (TMS) 7.6-6.6 (complex signal, 8H, arom), 4.8-4.4 (m, 1H, NCH), 4.62 (q, J=7Hz, 1H, CHMe), 4.3-3.9 (m, 2H, $NCHCH_2O$), 3.24 (dd, J=3.5Hz, J=13.3Hz, 1H, CH(H)Ph), 3.24 (d, l=4.7Hz, 1H, epox CH(H)), 2.95 (d, J=4.7Hz, 1H, epox. CH(HH)), 2.57 (dd, J=9.5Hz, J=13.3Hz, 1H, CH(HH)Ph), 1,19 (d, J=7Hz, 3H, Me)

REFERENCE EXAMPLE 29

(2R,3R)-3-(2,4-Difluorophenyl)-3,4-epoxy-2-methylbutanoic acid

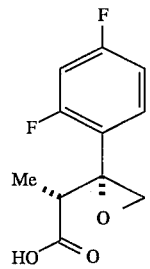

To a cooled (−5° C.) solution containing the unpurified aldol product obtained in reference example 28 (2 g) in a 4:1 mixture of $THF:H_2O$ (40 mL) it was added a solution containing LiOH (0.325 g, 7.8 mmol) and 35% aqueous solution of $H_2O_2$ (2 mL, 21 mmol) in water (8 mL). The reaction was stirred at 0° C. for 2 h. Then, a solution containing $Na_2SO_3$ (2.6 g, 21 mmol) in $H_2O$ (10 mL) was added and the volatiles were removed in vacuo. The alkaline aqueous residue was taken up with $CH_2Cl_2$ (3x) and the aqueous phase was then brought to pH 1 by addition of aqueous 2N HCl and extracted (3x) with $CH_2Cl_2$. The combined organic phases were dried over anhydrous $Na_2SO_4$, filtered and the filtrate was concentrated under reduced pressure to a white semisolid containing the title product (0.50 g).

$^1$H RMN (80 MHz, $CDCl_3$) δ (TMS) 10-8.5 (br, 1H, CO2H), 7.6-7.2 (complex signal, 1H, arom), 7.1-6.6 (complex signal, 2H, arom), 3.15 (d, J=4.7Hz, 1H, epox. CH(H)), 3.02 (q, J=7.3Hz, 1H, CHMe), 2.82 (d, J=4.7Hz, 1H, CH(H)), 1.20 (dd, $J_cF$=0.8Hz, $J_d$=7.3Hz, 3H, Me).

REFERENCE EXAMPLE 30

(2R ,3 R)-3-(2,4-Difluorophenyl)-3-hydroxy-2-methyl-4-(1H-1,2,4-triazol-1-yl)butanoic acid.

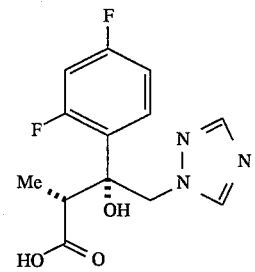

To a cooled (0° C.) suspension of Nail (55% mineral oil dispersion, 288 mg, 6.6 mmol, washed with hexane) in DMF (25 mL) was added 1,2,4-triazole (0.5 g, 7.2 mmol) and the mixture was stirred at 0° C. until hydrogen gas ceased to evolve. Then, a solution of unpurified (2R,3R)-3-(2,4-difluorophenyl)-3,4 -epoxy-2-methylbutanoic acid (0.5 g) (obtained in reference example 29) in DMF (3 mL) was slowly added and the mixture was heated to 60° C. during 2 h. A saturated $NH_4Cl$ aqueous solution was then added and the solvents were removed in vacuo. The mixture was then partitioned between brine containing AcOH and EtOAc. The organic layer was separated and the aqueous phase was extracted with more EtOAc (3x). The collected organic fractions were then dried over anhydrous $Na_2SO_4$, the drying agent was filtered and the filtrate was concentrated under reduced pressure to a white solid. Recrystallization from EtOAc afforded the title product as a white solid.

mp: 162°–164° C.;

$^1$H RMN (80 MHz, DMSO-$d_6$) δ (TMS) 8.25 (s, 1H, triazole), 7.57 (s, 1H, triazole), 7.4-6.7 (complex signal, 3H, arom), 4.67 (AB quartet, Δv=0.12, J=14.3Hz, 2H, $CH_2Tr$), 2.96 (br q, J=7.1Hz, 1H, CHMe), 0.80 (d, J=7.1Hz, 3H, Me)

REFERENCE EXAMPLE 31

(2R,3R)-3-Amino-2-(2,4-difluorophenyl)-1-(1H-1,2,4-triazol-1-yl)-2-butanol

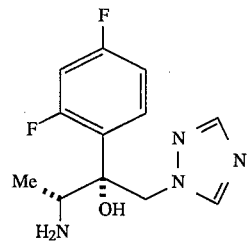

A solution of (2R,3R)-3-(2,4-difluorophenyl)-3-hydroxy-2-methyl-4-(1 H-1,2,4-triazol-1-yl)butanoic acid (50 mg, 0.17 mmol) (obtained in reference example 30) and triethylamine (0.35 mL, 0.25 mmol) in tert-butanol (3 mL) was treated with diphenylphosphoryl azide (0.44 mL, 0.20 mmol) and the reaction mixture was heated at reflux for 25 h. Removal of the volatiles under reduced pressure afforded a crude product that was partitioned between chloroform and saturated NaHCO₃ aqueous solution. The organic phase was dried over anhydrous Na₂SO₄, filtered and the filtrate was concentrated in vacuo to a brown oil that was dissolved in methanol (2 mL) and 1N aqueous KOH (1 mL) and then heated at 70° C. during 15 h. The volatiles were removed in vacuo and the aqueous residue was acidified to pH 1 by addition of 1N aqueous HCl and washed with CHCl₃. The aqueous phase was basified with saturated Na₂CO₃, saturated with NaCl and extracted (3x) with CHCl₃. The collected organic phases were dried over anhydrous Na₂SO₄, the drying agent was filtered and the filtrate was concentrated to afford the title product (18.8 mg) pure by TLC analysis. An analytical sample was obtained by chromatography on silica gel (CHCl₃: MeOH 5:1) as a white solid.

mp: 156°–157° C.;

¹H RMN (80 MHz, CDCl₃) δ (TMS) 7.96 (s, 1H, triazole), 7.78 (s, 1H, triazole), 7.7-7.3 (m, 1H, arom), 7.0-6.6 (m, 2H, arom), 4.67 (s, 2H, CH₂Tr), 3.61 (dq, $J_{CF}$=2.8Hz, $J_q$=6.5Hz, 1H, CHMe), 0.85 (d, J=6.5Hz, 3H, Me);

[α]$_D$–72.6° (c=1, CHCl₃); [lit [α]$_D$ –73° (c=1.06, CHCl₃)] (Chem. Pharm. Bull., 1991, 39, 2581-2589)

Analysis Calcd. for C₁₂H₁₄F₂N₄O: C 53.72, H 5.26, N 20.88. Found: C 53.38; H 5.32, N 21.24.

EXAMPLE 1

(2R*,3R*)-2-[2,4-Difluorophenyl]-3-[N-[4-(trifluoromethyl)benzoyl]-N-(2-benzyloxyethyl)amino]-1-(1H-1,2,4-triazol-1-yl)-2-butanol

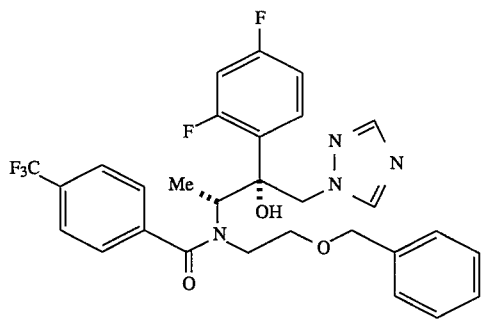

To a solution of (2R*,3R*)-3-[(2-benzyloxyethyl)amino]-2-[2,4-difluorophenyl]-1-(1H-1,2,4-triazol-1-yl)-2-butanol (4.40 g, 11.4 mmol) (obtained as described in reference example 2) in CH₂Cl₂ (40 mL) was added triethylamine (1.74 mL, 12.5 mmol). The resulting mixture was cooled in an ice bath and a solution of 4-(trifluoromethyl)benzoyl chloride (2.61 g, 12.5 mmol) in CH₂Cl₂ (5 mL) was carefully added and the mixture was stirred for 1 h at 0° C. and then for 18 h at room temperature. The resulting solution was diluted with CH₂Cl₂ and washed with 5% aqueous NaHCO₃ solution. The organic phase was separated, dried over Na₂SO₄ and the solvent was removed, to afford a thick oil (9.17 g) that was purified by chromatography on silica gel (EtOAc: hexane 1:1). The title compound of the example was obtained as a white foam.

¹H NMR (80 MHz, CDCl₃) δ (TMS): 7.9-7.1 (m, 12H, arom), 6.9-6.5 (m, 2H, arom), 5.06 (d, J-14 Hz, 1H, CH(H)), 4.54 (s, 2H, CH₂Ph), 4.6-3.5 (m, 6H), 1.5-1.0 (m, 3H, CHMe).

Analysis Calcd. for C₂₉H₂₇F₅N₄O₃: C 60.62; H 4.74; N 9.75. Found: C 60.43; H 4.69; N 9.32.

EXAMPLE 2

(2R*,3R*)-2-[2,4-Difluorophenyl]-3-[N-(2-benzyloxyethyl)-N-[4-(trifluoromethyl)benzoyl]amino]-1-(1H-1,2,4-triazol-1-yl)-2-butanol, oxalate

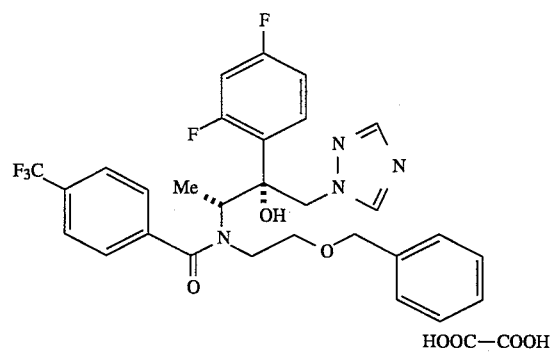

To a solution of the product obtained in example 1 in EtOAc was added a solution of oxalic acid in EtOAc. A little ether was added and the resulting solution was then allowed to precipitate at –20° C. overnight. The solid thus obtained was filtered and dried to afford the oxalate as a white solid.

mp: 56°–63° C.;

Analysis Calcd. for C₂₉H₂₇F₅N₄O₃·C₂O₄H₂·2H₂O: C 53.15; H 4.75; N 7.00.

Found: C 53.23; H 4.21; N 7.67.

EXAMPLE 3

(2R*,3R*)-2-[2,4-Difluorophenyl]-3-[N-(2-hydroxyethyl)-N-[4-(trifluoromethyl)-benzoyl]amino]-1-(1H-1,2,4-triazol-1-yl)-2-butanol

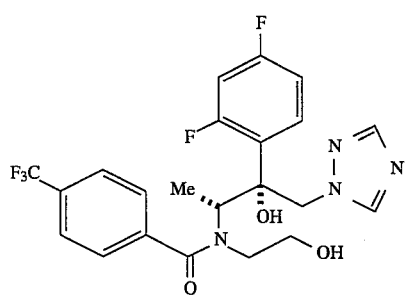

A mixture of the product obtained in example 1 (1.68 g, 2.9 mmol), 10% palladium on charcoal (420 mg) and ethanol (20 mL) was hydrogenated at 1 atm under vigorous stirring for 18 h. The mixture was filtered through celite and washed with ethanol. The filtrate was concentrated and the residue was purified by flash chromatography (EtOAc: Hex 4:1, then 1:0) to give the pure product as a white solid (718 mg, yield: 51%)

mp: 167°–168° C.;

¹H NMR (80 MHz, DMSO-d₆) δ (TMS): 8.30 and 8.17 (s, 1H, triazole), 8.0-6.7 (m, 8H, arom), 5.02 (br d, J=14 Hz, 1H, CH(H)), 4.8-4.1 (m), 3.9-3.3 (m), 1.3-1.0 (d J=7Hz, CHMe, 3H).

MS (DIP, CI, CH$_4$): M$^+$+1=485

Analysis Calcd. for C$_{22}$H$_{21}$F$_5$N$_4$O$_3$: C 54.55; H 4.37; N 11.57. Found: C 54.91; H 4.42; N 11.23.

EXAMPLE 4

(2R*,3R*)-2-[2,4-Difluorophenyl]-3-[N-(2-hydroxyethyl)-N-[4-(trifluoromethyl)-benzoyl]amino]-1-(1H-1,2,4-triazol-1-yl)-2-butanol, oxalate

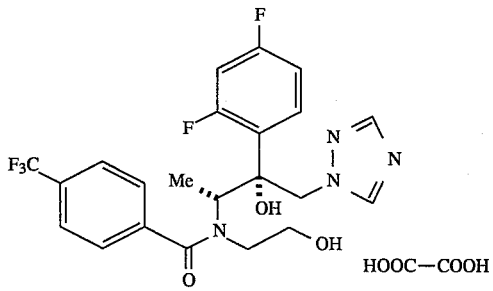

To a solution of the product obtained in example 3 in EtOAc was added a solution of oxalic acid in EtOAc, and the resulting solution was then allowed to precipitate at −20° C. overnight. The precipitate was filtered and dried to afford the oxalate as a white solid.

mp: 120°–122° C.;

Analysis Calcd. for C$_{22}$H$_{21}$F$_5$N$_4$O$_3$.C$_2$O$_4$H$_2$: C 50.18; H 4.04; N 9.75. Found: C 49.99; H 3.95; N 9.64.

EXAMPLE 5

(2R*,3R*)-2-[2,4-Dichlorophenyl]-3-[N-[4-(2,2,3,3-tetrafluoropropoxy)benzoyl]-N-(2-benzyloxyethyl)amino]-1-(1H-1,2,4-triazol-1-yl)-2-butanol

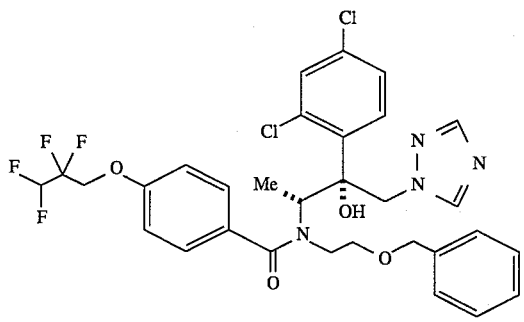

Following the procedure described in example 1, but starting from the compound obtained in reference example 4 and using 4-(2,2,3,3 -tetrafluoropropoxy)benzoyl chloride (obtained according to patent EP 472392), the title compound of the example was isolated as a white solid.

mp: 51°–62° C.;

$^1$H NMR (80 MHz, CDCl$_3$) δ (TMS): 8.30 (s, 1H, triazole), 7.9-6.8 (m, triazole, arom), 6.05 (tt, J=4.8Hz, J=53Hz, 1H, CF$_2$H), 5.6-5.3 (m), 4.7-3.8 (m), 3.72 (s), 1.26 and 1.05 (d, J=6.8Hz, 3H, CHMe).

Analysis Calcd. for C$_{31}$H$_{30}$Cl$_2$F$_4$N$_4$O$_4$: C 55.61; H 4.52; N 8.37. Found: C 55.69; H 4.66; N 8.31.

EXAMPLE 6

(2R*,3R*)-2-[2,4-Dichlorophenyl]-3-[[N-[4-(2,2,3,3-tetrafluoropropoxy) benzoyl]-N-(2-hydroxyethyl)]amino]-1-(1H-1,2,4-triazol-1-yl)-2-butanol

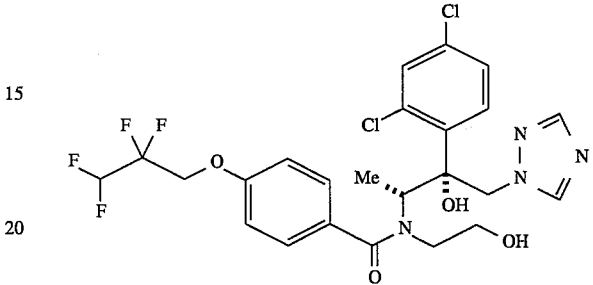

Following the procedure described in example 3, but hydrogenating the compound obtained in example 5, the title compound was obtained as a white wax.

$^1$H NMR (80 MHz, CDCl$_3$) δ (TMS): 8.29 (s), 8.1-6.9 (m, triazole, arom), 6.06 (tt, J=4.6 Hz, J=53 Hz, 1H, CF$_2$H), 5.5-5.0 (m), 5.0-3.5 (m), 1.27 and 1.06 (d, J=7 Hz, 3H, CHMe).

Analysis Calcd. for C$_{24}$H$_{24}$Cl$_2$F$_4$N$_4$O$_4$: C 49.75; H 4.18; N 9.67. Found: C 50.02; H 4.41; N 9.99.

EXAMPLE 7

(2R*,3R*)-2-[2,4-Difluorophenyl]-3-[[N-[4-(trifluoromethyl)benzoyl]-N-(2-acetoxyethyl)]amino]-1-(1H-1,2,4-triazol-1-yl)-2-butanol

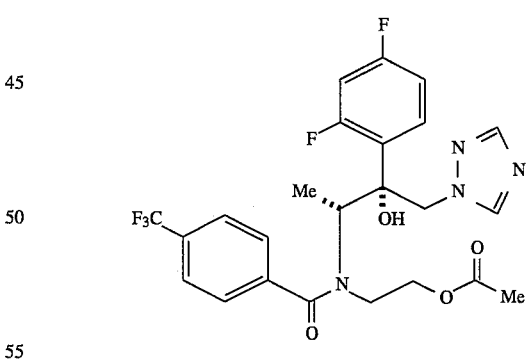

To a solution of (2R*,3R*)-2-[2,4-difluorophenyl]-3[ [N-[4-(trifluoromethyl)benzoyl]-N-(2-benzyloxyethyl)] amino]-1-(1 H-1,2,4-triazol-1 -yl)-2-butanol (0.26 g, 0.53 mmol) (obtained as described in example 1) in 5 mL of CH$_2$Cl$_2$, was added triethylamine (0.09 mL, 0.67 mmol). The resulting mixture was cooled in an ice bath, acetyl chloride was added (0.042 mL, 0.59 mmol) and the mixture was stirred for 2 h at 0° C. The mixture was diluted with CH$_2$Cl$_2$ and washed with 5% NaHCO$_3$ aqueous solution. The organic phase was separated, dried over Na$_2$SO$_4$ and the solvent was removed, to afford a thick oil that was purified by chromatography on silica gel (EtOAc: Hex 3:1). The title compound was obtained as a white solid (180 mg).

mp: 152°–153° C.;

$^1$H NMR (80 MHz, CDCl$_3$) δ (TMS): 7.9-7.5 (m, 7H, triazole, arom), 7.0-6.6 (m, 2H, arom), 5.3-3.5 (m, 7H), 2.06 (s, 3H, Ac), 1.4-1.1 (m, 3H, CHMe).

Analysis Calcd. for C$_{24}$H$_{23}$F$_5$N$_4$O$_4$: C 54.76; H 4.40; N 10.64. Found: C 54.89; H 4.41; N 10.21.

EXAMPLE 8

(2R*,3R*)-2-[2,4-Difluorophenyl]-3-[[N-[4-(trifluoromethyl)benzoyl]-N-(2-(4-trifluoromethylbenzoyloxy)ethyl)]amino]-1-(1H-1,2,4-triazol-1-yl)-2-butanol

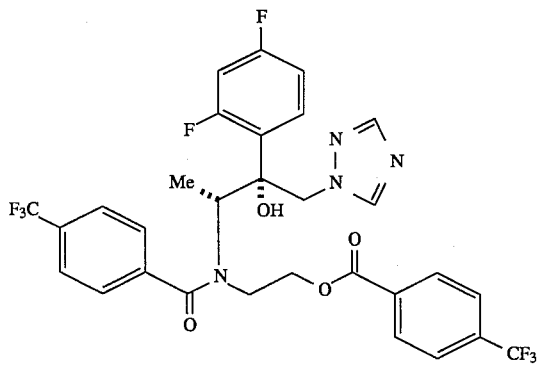

Following the procedure described in example 7, but using 4-(trifluoromethyl)benzoyl chloride instead of acetyl chloride, the title compound of the example was obtained in a similar yield.

mp: 55°–60° C.;

$^1$H NMR (80 MHz, CDCl$_3$) δ (TMS): 8.4-7.5 (m, 11H, triazole, arom), 6.9-6.6 (m, 2H, arom), 5.4-3.7 (m, 7H), 1.4-1.1 (m, 3H, CHMe).

Analysis Calcd. for C$_{30}$H$_{24}$F$_8$N$_4$O$_4$: C 54.88; H 3.68; N 8.53. Found: C 55.04; H 3.96; N 8.45.

EXAMPLE 9

(2R*,3R*)-2-[2,4-Dichlorophenyl]-3-[[N-[4-(trifluoromethyl)benzoyl]-N-(2-benzyloxyethyl)]amino]-1-(1H-1,2,4-triazol-1-yl)-2-butanol

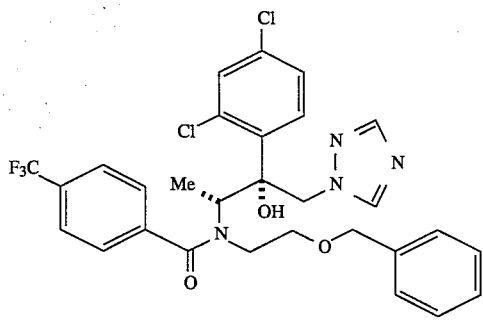

Following the procedure described in example 1, but using the compound obtained in reference example 4, the title compound of the example was obtained as a white solid.

mp: 96°–97° C.;

$^1$H NMR (80 MHz, CDCl$_3$) δ (TMS): 7.9-7.0 (m, 14H, triazole, arom), 5.52 (d, J=14 Hz, CH(H)), 4.8-4.4 (m), 4.1-3.8 (m, 1H), 3.67 (s, 2H, CH$_2$Ph), 1.28 and 1.03 (d, J=6.8 Hz, CHMe).

Analysis Calcd. for C$_{29}$H$_{27}$Cl$_2$F$_3$N$_4$O$_3$: C 57.34; H 4.48; N 9.22. Found: C 57.47; H 4.45; N 9.15.

EXAMPLE 10

(2R*,3R*)-2-[2,4-Dichlorophenyl]-3-[N-(2-hydroxyethyl)-N-[4-(trifluoromethyl)-benzoyl]amino]-1-(1H-1,2,4-triazol-1-yl)-2-butanol

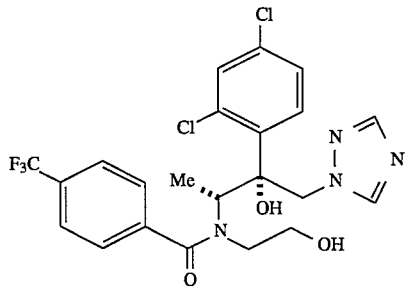

Following the procedure described in example 3, the product of example 9 was hydrogenated to afford the title compound as a white solid in a similar yield.

mp: 185°–189° C.;

$^1$H NMR (80 MHz, CDCl$_3$) δ (TMS): 8.0-7.0 (m, 9H, triazole, arom), 5.5-4.5 (m), 4.4-3.5 (m), 1.29 and 1.06 (d, J=7 Hz, CHMe).

Analysis Calcd. for C$_{22}$H$_{21}$Cl$_2$F$_3$N$_4$O$_3$: C 51.08; H 4.09; N 10.83. Found: C 51.47; H 4.05; N 10.70.

EXAMPLE 11

(2R*,3R*)-3-[N-(2-tert-Butoxycarbonylaminoethyl)-N-[4-(trifluoromethyl)-benzoyl]amino]-2-[2,4-difluorophenyl]-1-(1H-1,2,4-triazol-1-yl)-2-butanol

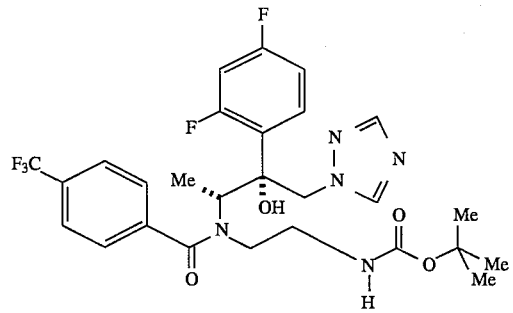

Following the procedure described in example 1, but using the compound obtained in reference example 7, the title compound of the example was obtained as a white solid.

mp: 135°–143° C.;

¹H NMR (80 MHz, CDCl₃) δ (TMS): 7.8-7.4 (m, 7H, triazole, arom), 7.0-6.7 (m, 2H, arom), 5.5-5.0 (m, 3H), 4.6-4.3 (m, 2H), 3.6-3.3 (m, 1H), 3.14 (s, 3H), 1.56 and 1.41 (s, 9H, CMe₃), 1.3-1.1 (m, 3H, CHMe).

Analysis Calcd. for $C_{27}H_{30}F_5N_5O_4$: C 55.57; H 5.18; N 12.00. Found: C 55.44; H 4.52; N 11.42.

EXAMPLE 12

(2R*,3R*)-3-[N-(2-Aminoethyl)-N-[4-(trifluoromethyl)benzoyl]amino]-2-[2,4-difluorophenyl]-1-(1H-1,2A-triazol-1-yl)-2-butanol

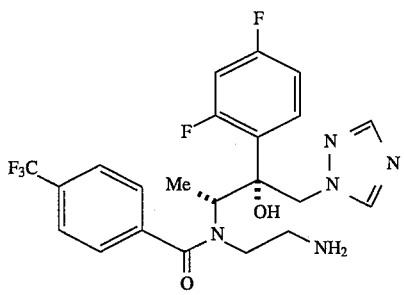

A solution containing the compound obtained in example 11 (0.5 g) was treated with a saturated solution of HCl in methanol (12 mL) at reflux for 3 h. The mixture was concentrated and the residue partitioned between EtOAc and 10% NaHCO₃ solution. The organic phase was dried, the solvent was removed and the residue was purified by flash chromatography (EtOAc:Hex 4:1), to give 97 mg of pure product.

mp: 230°–235° C.;

¹H NMR (80 MHz, CDCl₃) δ (TMS): 7.8-7.4 (m, 7H, triazole, arom), 7.0-6.7 (m, 2H, arom), 5.5-4.5 (m), 4.4-3.7 (m), 3.7-3.3 (m), 3.4-2.5 (m), 1.5-0.9 (m, 3H, CHMe).

HPLC-MS (CI, CH₄): M⁺+1=484

Analysis Calcd. for $C_{22}H_{22}F_5N_5O_2$: C 54.66; H 4.59; N 14.49. Found: C 54.80; H 4.43; N 13.74.

EXAMPLE 12A (2R*, 3R*) -3-[N-(2-Aminoethyl)-N-[4 -(trifluoromethyl)benzoyl]amino]-2-[2,4-dichlorophenyl]-1 -1,2,4-triazol-1-yl)-2-butanol, and the homochiral (2R,3R) compound, are prepared in a manner analogous to the described preparation of the 2,4-difluorophenyl compound of Example 12.

EXAMPLE 13

(5R*,6R*)-6-[2,4-Difluorophenyl]-5-methyl-2-hydroxy-4-[4-(trifluoromethyl)-benzoyl]-6-[(1H-1,2,4-triazol-1-yl)methyl]morpholine

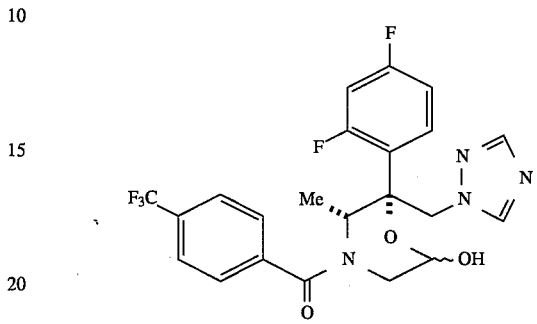

Method A: To a cooled (–78° C.) solution containing oxalyl chloride (0.093 mL, 1.08 mmol) in CH₂Cl₂ (5 mL) was added dropwise anhydrous DMSO (0.15 mL, 2.17 mmol). Ten minutes after, it was added a solution of (2R*, 3R*)-2-[2,4 -difluorophenyl]-3-[N-(2-hydroxyethyl)-N-[4-(trifluoromethyl) benzoyl]amino] -1-(1H-1,2,4-triazol-1-yl)-2-butanol (obtained in example 3) (420 mg, 0.87 mmol) in DMSO—CHCl₃. The mixture was stirred during 30 min, after which period freshly distilled triethylamine (0.6 mL, 4.33 mmol) was added. The reaction flask was then let warm to –40° C. and the mixture was stirred at this temperature for 1 h and at –10° C. during 30 min. A 0.5M NaHSO₄ solution was then added and the organic phase was washed with water and brine. Drying over anhydrous Na₂SO₄, filtration and concentration gave a crude product that was chromatographed on silica gel (EtOAc: Hex 4:1) to afford the title product as a white solid (145 mg, 34% yield).

Method B: Alternatively, this compound may also be obtained by the following method: a solution of (2R*,3R*)-2-[2,4-difluorophenyl]-3-[[N-[4 -(trifluoromethyl)benzoyl]-N-(2-hydroxyethyl)]amino]-1-(1H-1,2,4-triazol-1 -yl)-2-butanol (250 mg, 0.51 mmol) (obtained according to example 3) in acetone (5 mL) was treated with tris(triphenylphosphine)ruthenium (II) chloride (10 mg) and N-methylmorpholine N-oxide (250 mg, 2.1 mmol) at room temperature for 20 h. The mixture was concentrated and the residue purified by flash chromatography (EtOAc: Hex 4:1) to give the title compound as a white solid (75 mg).

mp: 193°–195 ° C.;

¹H NMR (80 MHz, MeOH-d₄) δ (TMS): 8.0-7.2 (m, 7H, triazole, arom), 7.0-6.6 (m, 2H, arom), 5.9-5.3 (m, 2H, Tr—CH(H), OCHOH), 5.2-4.2 (m, 2H, Tr—CH(H), CHMe), 3.7 (br s, 2H, OCHCH₂), 1.13 (d, J=6.8Hz, 3H, CHMe.).

Analysis Calcd. for $C_{22}H_{19}F_5N_4O_3$: C 54.78; H 3.97; N 11.61. Found: C 54.48; H 3.98; N 11.87.

EXAMPLE 14

(2R*,3R*)-3-[N—Cyanomethyl-N-(4-trifluoromethylbenzoyl)amino]-2-[2,4-difluorophenyl]-1-(1H-1,2,4-triazol-1-yl)-2-butanol, oxalate

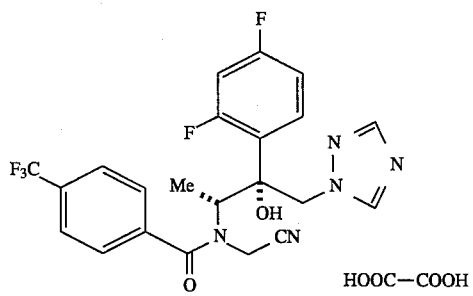

Following the procedure described in example 1, but using the compound obtained in reference example 5 and subsequently preparing the oxalate, the title compound of the example was obtained as a white solid.

mp: 131°–133° C.;

$^1$H NMR (80 MHz, MeOH-d4) δ (TMS): 8.25 (s, 1H, triazole), 8.0-7.5 (m, 5H, triazole, arom), 7.5-7.1 (m, 1H, arom), 7.0-6.6 (m, 2H, arom), 4.76 (s, 4H, Tr—CH$_2$, CH$_2$CN), 4.9-4.5 (m, 1H, CHMe), 1.23 (d, J=7 Hz, 3H, CHMe).

Analysis Calcd. for $C_{22}H_{18}F_5N_5O_2 \cdot C_2O_4H_2 \cdot H_2O$: C 49.07; H 3.77; N 11.92.

Found: C 48.52; H 3.57; N 11.81.

EXAMPLE 15

(2R*,3R*)-2-[2,4-Difluorophenyl]-3-[[N-[4-(2,2,3,3-tetrafluoropropoxy)benzoyl]-N-(2-benzyloxyethyl)]amino]-1-(1H-1,2,4-triazol-1-yl)-2-butanol

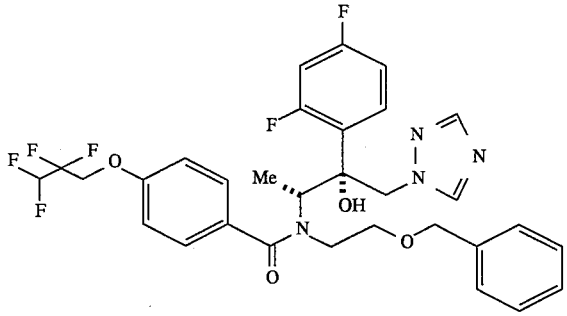

Following the procedure described in example 1, but using 4-(2,2,3,3-tetrafluoropropoxy)benzoyl chloride (obtained according to patent EP 472392) instead of 4-(trifluoromethyl)benzoyl chloride, the title compound was obtained.

$^1$H NMR (80 MHz, CDCl$_3$) δ (TMS): 8.20 (s, 1H, triazole), 7.7-7.2 (m, triazole, arom), 7.1-6.1 (m, arom), 6.06 (tt, J=4.7Hz, J=53Hz, 1H, CF$_2$H), 5.03 (d, J=14.4Hz, 1H, CH(H)-Tr) 4.7-4.1 (m), 3.9-3.5 (m), 1.4-1.0 (m, 3H, CHMe).

EXAMPLE 16

(2R*,3R*)-2-[2,4-Difluorophenyl]-3-[[N-[4-(2,2,3,3-tetrafluoropropoxy)benzoyl]-N-(2-hydroxyethyl)]amino]-1-(1H-1,2,4-triazol-1-yl)-2-butanol

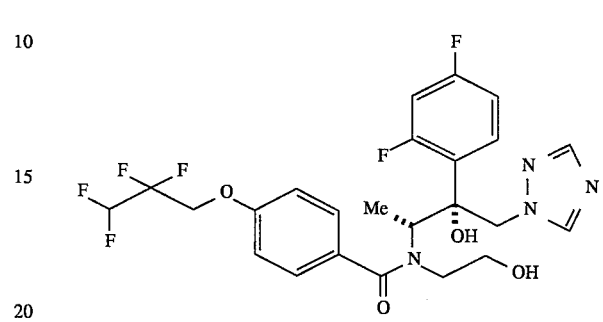

Following the procedure described in example 3, but using the compound obtained in example 15, the title compound was obtained.

mp: 156°–157° C.;

$^1$H NMR (80 MHz, CDCl$_3$)δ (TMS): 8.26 (s, 1H, triazole), 8.0-6.6 (m, 8H, triazole, arom), 6.06 (tt, J=4.7Hz, J=53Hz, 1H, CF$_2$H), 5.1-3.6 (m), 1.4-1.0 (m, 3H, CHMe);

Analysis Calcd. for $C_{24}H_{24}F_6N_4O_4$: C 52.75; H 4.43; N 10.25. Found: C 53.16; H 4.61; N 9.88.

EXAMPLE 17

(5R*,6R*)-6-[2,4-Difluorophenyl]-5-methyl-2-hydroxy-4-[4-(2,2,3,3-tetrafluoropropoxy)benzoyl]-6-[(1H-1,2,4-triazol-1-yl)methyl]morpholine

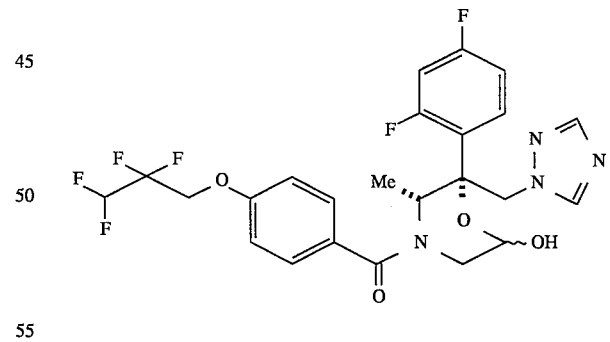

Following the Method A described in example 13, but using the compound obtained in example 16, the title compound of the example was obtained.

mp: 209°–210° C.;

$^1$H NMR (80 MHz, CDCl$_3$) δ (TMS): 7.85 (s, 1H, triazole), 7.70 (s, 1H, triazole), 7.6-6.8 (m, 7H, arom), 6.06 (tt, J=4.8Hz, J=53Hz, 1H, CF$_2$H), 5.9-5.4 (m, 2H), 5.2-4.5 (m, 2H), 4.41 (dt, J=11.9Hz, J=1.4Hz, 2H, CH$_2$CF$_2$), 4.0-3.1 (m, 2H), 1.10 (d, J= 6.8Hz, 3H, CMe);

Analysis Calcd. for $C_{24}H_{22}F_6N_4O_4$: C 52.95; H 4.07; N 10.29. Found: C 53.20; H 4.22; N 10.17.

EXAMPLE 18

(2R*,3R*)-2-[2,4-Difluorophenyl]-3-[[N-[4-(trifluoromethoxy)benzoyl]-N-(2-benzyloxyethyl)]amino]-1-(1H-1,2,4-triazol-1-yl)-2-butanol

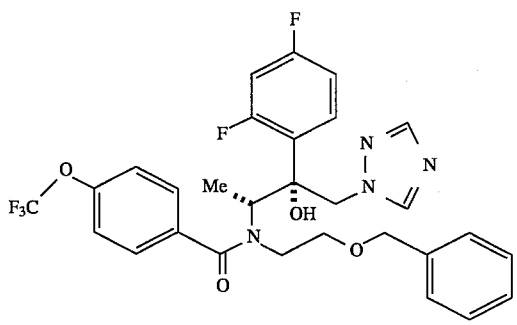

Following the procedure described in example 1, but using 4-(trifluoromethoxy)benzoyl chloride instead of 4-(trifluoromethyl)benzoyl chloride, the title compound was obtained.

$^1$H NMR (80 MHz, CDCl$_3$) δ (TMS): 8.22 (s, 1H, triazole), 7.7-7.1 (m, 11H, triazole, arom), 6.9-6.5 (m, 2H, arom), 5.04 (br d, J=14.4Hz, 1H, CH(H)Tr), 4.56 (s, 2H, CH$_2$Ph), 4.7-3.4 (m, 6H), 1.4-1.0 (m, 3H, CHMe).

EXAMPLE 19

(2R*,3R*)-2-[2,4-Difluorophenyl]-3-[[N-[4-(trifluoromethoxy)benzoyl]-N-(2-hydroxyethyl)]amino]-1-(1H-1,2,4-triazol-1-yl)-2-butanol

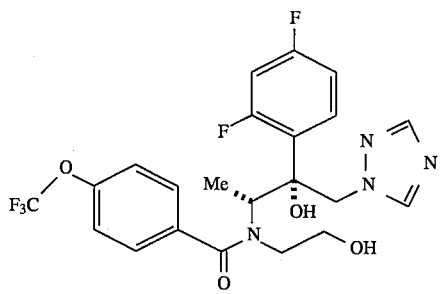

Following the procedure described in example 3, but using the compound obtained in example 18, the title compound was obtained.

mp: 145°–146° C.;

$^1$H NMR (80 MHz, CDCl$_3$) δ (TMS): 8.27 (s, 1H, triazole), 8.0-7.1 (m, 6H, triazole, arom), 7.0-6.5 (m, 2H, arom), 5.1-4.4 (m), 4.3-3.6 (m), 1.4-1.0 (m, 3H, CHMe).

Analysis Calcd. for C$_{22}$H$_{21}$F$_5$N$_4$O$_4$: C 52.80; H 4.23; N 11.20. Found: C 52.55; H 4.17; N 10.80.

EXAMPLE 20

(2R*,3R*)-2-[2,4-Difluorophenyl]-3-[[N-[4-(2,2,2-trifluoroethoxy)benzoyl]-N-(2-benzyloxyethyl)]amino]-1-(1H-1,2,4-triazol-1-yl)-2-butanol

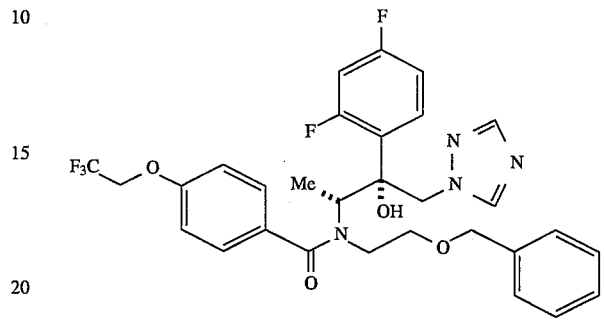

Following the procedure described in example 1, but using 4-(2,2,2-trifluoroethoxy)benzoyl chloride instead of 4-(trifluoromethyl)benzoyl chloride, the title compound was obtained.

$^1$H NMR (80 MHz, CDCl$_3$) δ (TMS): 8.19 (s, 1H, triazole), 7.7-7.2 (m, triazole, arom), 7.31 (s, 5H, benzyl), 6.95 (d, J=8.7Hz, 2H, arom), 6.8-6.5 (m, 2H, arom), 5.03 (br d, J=14.4Hz, 1H, CH(H)Tr), 4.8-4.0 (m, 2H), 4.57 (s, 2H, CH$_2$Ph), 4.39 (q, J=8.1Hz, 2H, CH$_2$CF$_3$), 4.0-3.5 (m, 4H), 1.4-1.0 (m, 3H, CHMe).

EXAMPLE 21

(2R*,3R*)-2-[2,4-Difluorophenyl]-3-[[N-[4-(2,2,2-trifluoroethoxy)benzoyl]-N-(2-hydroxyethyl)]amino]-1-(1H-1,2,4-triazol-1-yl)-2-butanol

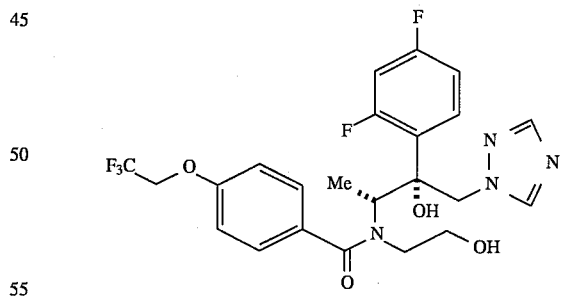

Following the procedure described in example 3, but using the compound obtained in example 20, the title compound was prepared in a similar yield.

mp: 110°–112° C.;

$^1$H NMR (80 MHz, CDCl$_3$) δ (TMS): 8.28 (s, 1H, triazole), 8.0-7.3 (m, 4H, triazole, arom), 7.02 (d, J=8.5Hz, 2H, arom), 6.9-6.5 (m, 2H, arom), 5.1-3.5 (m), 4.41 (q, J=8.1Hz, 2H, CH$_2$CF$_3$), 1.4-1.0 (m, 3H, CHMe);

Analysis Calcd. for C$_{23}$H$_{23}$F$_5$N$_4$O$_4$: C 53.70; H 4.51; N 10.89. Found: C 53.70; H 4.47; N 10.69.

EXAMPLE 22

(5R*,6R*)-6-[2,4-Dichlorophenyl]-5-methyl-2-hydroxy-4-[4-(2,2,3,3-tetrafluoropropoxy)benzoyl]-6-[(1H-1,2,4-triazol-1-yl)methyl]morpholine

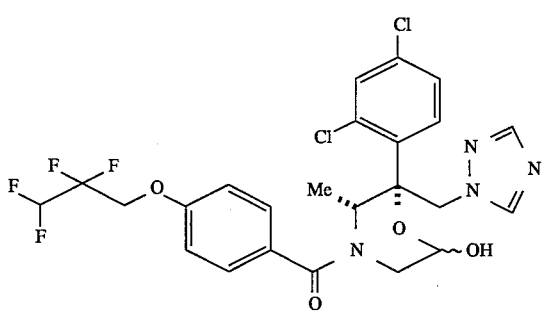

Following the Method A described in example 13, but using the compound obtained in example 6, the title compound was obtained.

¹H NMR (80 MHz, CDCl₃) δ (TMS): 7.85 (s, 1H, triazole), 7.8-7.0 (m, 8H, arom), 6.09 (tt, J=4.8Hz, J=53Hz, 1H, CF₂H), 5.9-5.2 (m, 2H), 5.2-4.5 (m, 2H), 4.41 (dt, J=12Hz, J=1.4Hz, 2H, CH₂CF₂), 4.0-3.0 (m, 2H), 1.10 (d, J=7Hz, 3H, CHMe);

Analysis Calcd. for C₂₄H₂₂Cl₂F₃N₄O₄: C 51.63; H 3.97; N 10.03 Found: C 51.55; H 4.24; N 10.21.

EXAMPLE 23

(5R*,6R*)-6-[2,4-Dichlorophenyl]-5-methyl-2-hydroxy-4-[4-(trifluoromethyl)-benzoyl]-6-[(1H-1,2,4-triazol-1-yl)methyl]morpholine

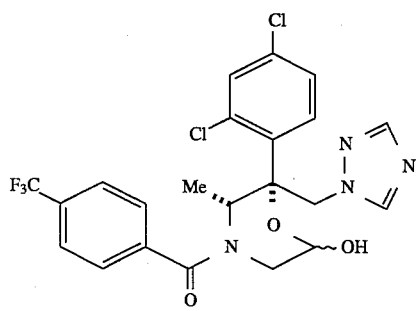

Following the Method A described in example 13, but using the compound obtained in example 10, the title compound was prepared.

mp: 199°-200° C.;

¹H NMR (80 MHz, CDCl₃) δ (TMS): 7.83 (s, 1H, triazole), 7.8-7.0 (m, 8H, triazole, arom), 6.3-5.6 (m), 5.6-5.2 (m), 5.1-4.6 (m), 3.9-3.3 (m, 2H, OCHCH₂), 1.11 (d, J=7.2Hz, 3H, CHMe);

Analysis Calcd. for C₂₂H₁₉Cl₂F₃N₄O₃.1/2 AcOEt: C 51.53; H 4.14; N 10.02.
Found: C 52.33; H 4.19; N 10.02.

EXAMPLE 24

(SR*,6R*)-6-[2,4-Dichlorophenyl]-5-methyl-2-(1H-1,2,4-triazol-1-yl)-4-[4-(trifluoromethyl)benzoyl]-6-[(1H-1,2,4-triazol-1-yl)methyl]morpholine

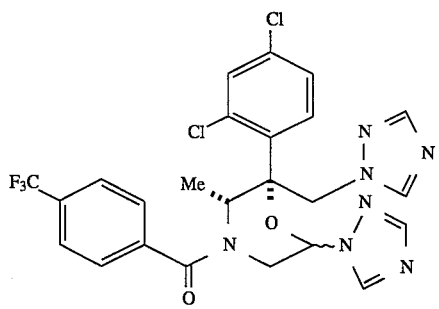

To a cooled (0° C.) solution containing the compound of example 23 (300 mg, 0.58 mmol), triphenylphosphine (305 mg, 1.16 mmol, 2 eq), and 1,2,4 -triazole (80.4 mg, 1.16 mmol, 2 eq) in dry THF (10 mL) it was added diethylazadicarboxylate (203 mg, 0.183 mL, 1.16 mmol, 2 eq). The mixture was stirred at 0° C. during 30 min and at room temperature during 1 h. The volatiles were then removed in vacuo and the residue was chromatographed on silica gel (EtOAc) to afford the title compound as white solid.

mp: 191°-201° C.;

¹H NMR (80 MHz, MeOH-d4) δ (TMS): 8.74 (s, 1H, triazole), 8.05 (s, 1H, triazole), 7.83 (br s, 5H, triazole, arom), 7.6-7.3 (m, 3H, triazole, arom), 7.18 (br d, J=8.9Hz, 1H, arom), 6.5-6.1 (m, 1H, OCHTr), 5.29 (s, 2H), 5.3-5.0 (m, 1H, CHMe), 4.18 (br s, 2H), 1.26 (d, J=6.6Hz, 3H, CHMe);

Analysis Calcd. for C₂₄H₂₀Cl₂F₃N₇O₂: C 50.90; H 3.56; N 17.31. Found: C 50.66; H 3.43; N 16.98.

EXAMPLE 25

(5R*,6R*)-6-[2,4-Dichlorophenyl]-5-methyl-2-fluoro-4-[4-(trifluoromethyl)-benzoyl]-6-[(1H-1,2,4-triazol-1-yl)methyl]morpholine

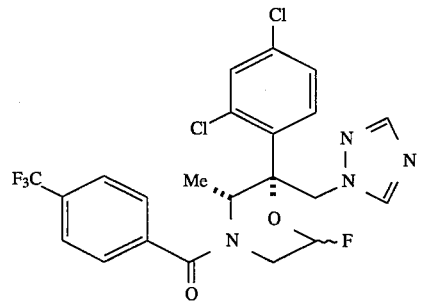

To a cooled (−10° C.) solution containing the compound of example 23 (360 mg, 0.70 mmol) in CH₂Cl₂ (4 mL) it was added a solution containing diethylaminosulfur trifluoride (DAST) (124 mg, 0.102 mL, 0.77 mmol, 1.1 eq) in CH₂Cl₂ (1 mL) and the reaction mixture was stirred for 1 h. The reaction was quenched by the addition of water (10 mL) and more CH₂Cl₂ was added. The organic phase was separated and washed with 5% NahCO₃ aqueous solution and brine, dried over anhydrous Na₂SO₄, the drying agent was then filtered and the resulting filtrate was concentrated to an oil that was purified by silica gel chromatography (EtOAc:Hex 2:1) to afford the title product as a white solid in poor yield.

mp: 151°–156° C.;

¹H NMR (80 MHz, MeOH-d4) δ (TMS): 8.34 (s, 1H, triazole), 8.0-7.7 (m, triazole, arom), 7.6-7.1 (m, arom), 6.9-6.5 (m), 6.4-5.8 (m), 5.7-4.8 (m), 4.2-3.3 (m), 1.4-0.8 (m, 3H, CHMe);

Analysis Calcd. for $C_{22}H_{18}Cl_2F_4N_4O_2$: C 51.08; H 3.51; N 10.83. Found: C 51.46; H 3.63; N 10.70.

EXAMPLE 26

(2R*,3R*)-N-[3-(2,4-Difluorophenyl)-3-hydroxy-4-(1H-1,2,4-triazol-1-yl)-2-butyl]-N-[4-(trifluoromethyl)benzoyl]glycine, benzyl ester

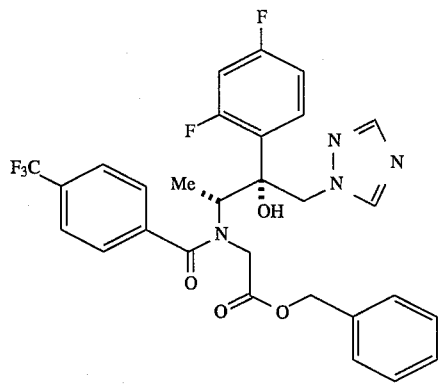

Following the procedure described in example 1, but starting from the compound obtained in reference example 8, the title compound was obtained as a white solid.

mp: 175°–181° C.;

¹H NMR (80 MHz, CDCl₃) δ (TMS): 8.0-7.0 (complex signal, 15H, triazole, arom), 6.9-6.5 (m, 2H, arom), 5.7-5.0 (m), 4.85 (br s), 4.7-4.2 (m), 1.2-0.9 (m, 3H, CHMe);

Analysis Calcd. for $C_{29}H_{25}F_5N_4O_4$: C 59.18; H 4.28; N 9.52. Found: C 59.93; H 4.59; N 9.20.

EXAMPLE 27

(2R*,3R*)-N-[3-(2,4-Dichlorophenyl)-3-hydroxy-4-(1H-1,2,4-triazol-1-yl)-2-butyl]-N-[4-(trifluoromethyl)benzoyl]glycine, ethyl ester

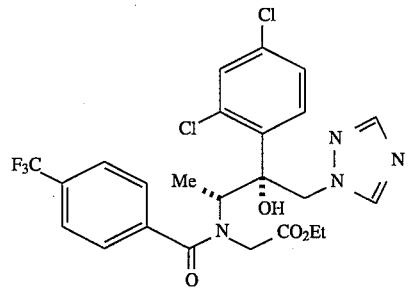

Following the procedure described in example 1, but starting from the compound obtained in reference example 9, the title compound was obtained.

mp: 170°–178° C.;

¹H NMR (80 MHz, CDCl₃) δ (TMS): 8.04 (s, 1H, triazole), 7.9-7.3 (m, 8H, triazole, arom), 7.2-6.9 (m, 1H, arom), 6.3-5.7 (m), 5.4-5.2 (m), 5.03 (s), 5.1-4.8 (m), 4.57 (s), 4.4-4.1 (m), 4.08 (q, J=7.1Hz, OCH? CH3), 1.35 (t, J=7.1Hz, OCH₂CH₃), 1.2-0.9 (m, 3H, CHMe).

Analysis Calcd. for $C_{24}H_{23}Cl_2F_3N_4O_4$: C 51.53; H 4.14; N 10.02. Found: C 51.83; H 4.22; N 9.93.

EXAMPLE 28

(2R*,3R*)-N-[3-(2,4-Difluorophenyl)-3-hydroxy-4-(1H-1,2,4-triazol-1-yl)-2-butyl]-N-[4-(trifluoromethyl)benzoyl]glycine

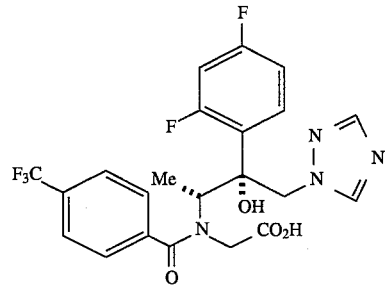

To a solution of (2R*,3R*)-2-(2,4-difluorophenyl)-3-(N-benzyloxy carbonylmethylamino-N-4-trifluoromethylbenzoylamino)-1-(1H-1,2,4-triazol-1-yl)-2-butanol (3.4 g, 5.7 mmol) (obtained in example 26) in ethanol (90 mL) was added 10% palladium on charcoal (0.8 g) and the mixture was hydrogenated (1 atm) during 2 h. The mixture was filtered and the solvent removed in vacuo to afford the title product as a white solid (2.81 g, 99%).

mp: 182°–183° C.;

¹H NMR (80 MHz, MeOH-d4) δ (TMS): 8.24 and 8.18 (s, 1H, triazole), 8.0-7.6 (m, triazole, arom), 7.5-7.1 (m, 1H, arom), 7.0-6.6 (m, 2H, arom), 5.9-5.6 (m), 5.10 (br s), 4.97 (s), 4.76 (s), 4.60 (s), 4.50 (s), 4.32 (s), 1.11 (d, J=6.8Hz, 3H, CHMe);

Analysis Calcd. for $C_{22}H_{19}F_5N_4O_4$: C 53.02; H 3.84; N 11.24. Found: C 53.71; H 3.91; N 11.38.

EXAMPLE 29

(5R*,6R*)-6-[2,4-Difluorophenyl]-5-methyl-4-[4-(trifluoromethyl)benzoyl]-6-[(1H-1,2,4-triazol-1-yl)methyl]-2-morpholinone

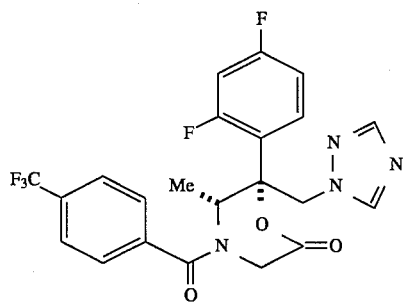

Method A: A cooled (−10° C.) solution containing (2R*,3R*)-N-[3-(2,4-difluorophenyl)-3-hydroxy-4-(1H-1,2,4-triazol-1-yl)-2-butyl]-N-[4-(trifluoromethyl)benzoyl]glycine (12.24 g, 24.55 mmol) (obtained in example 28) in pyridine was treated with trifluoroacetic anhydride (5.2 mL, 36.83 mmol, 1.5 eq). The mixture was stirred during 15 min at −10° C. and during 2 h at 0° C. The resulting red solution was then quenched by the addition of pH 7 phosphate buffer, concentrated in vacuo and partitioned between water and CHCl₃. The aqueous phase was discarded and the organic layer was washed with 5% aqueous NaHCO₃ and brine, then it was dried over anhydrous Na₂SO₄, the drying agent was filtered and the filtrate was concentrated to a reddish solid which was flash-chromatographed (EtOAc:Hex 2:1) to a white solid (10.0 g, 85%).

mp: 184°–186° C.;

¹H NMR (80 MHz, CDCl₃) δ (TMS): 8.0-7.3 (m, 7H, triazole, arom), 7.0-6.7 (m, 2H, arom), 4.79 (s), 4.4-4.0 (m), 1.20 and 1.11 (d, J=7Hz, 3H, CHMe).

MS (EI): M⁺+1=480

Analysis Calcd. for $C_{22}H_{17}F_5N_4O_3$: C 55.01; H 3.57; N 11.66. Found: C 55.10; H 3.49; N 11.51.

Method B: A solution containing (2R*,3R*)-N-[3-(2,4-difluorophenyl)-3-hydroxy-4-(1H-1,2,4-triazol-1-yl)-2-butyl]-N-[4-(trifluoromethyl)benzoyl]glycine (122 mg, 0.24 mmol) (obtained in example 28) in DMF (5 mL) was treated with DCC (60 mg, 0.29 mmol) and the mixture stirred during 20 h. The precipitated urea was filtered and the filtrate was partitioned between water and EtOAc. The aqueous phase was separated and the organic phase was washed with 5% NaHCO₃ aqueous solution and brine, then dried over anhydrous Na₂SO₄, the drying agent was filtered and the filtrate was concentrated to afford the title compound in quantitative yield. This procedure, however, yielded trace amounts of dicyclohexylurea difficult to remove from the desired product.

Method C: a suspension of (2R*,3R*)-2-[2,4-difluorophenyl]-3-[[N-[4-(trifluoromethyl)benzoyl]-N-(2-hydroxyethyl)]amino]-1-(1H-1,2,4-triazol-1-yl)-2-butanol (100 mg, 0.2 mmol) (obtained as described in example 3), and 1 g of silver carbonate suspended in celite in benzene (10 mL) was heated under reflux for 4 h. The mixture was concentrated and the product was isolated by flash chromatography (EtOAc: Hex 3:1) to give the title compound of the example as a white solid (23 mg, yield: 24%).

EXAMPLE 30

(2R*,3R*)-N-[3-(2,4-Difluorophenyl)-3-hydroxy-4-(1H-1,2,4-triazol-1-yl)-2-butyl]-N-[4-(trifluoromethoxy)benzoyl]glycine, benzyl ester

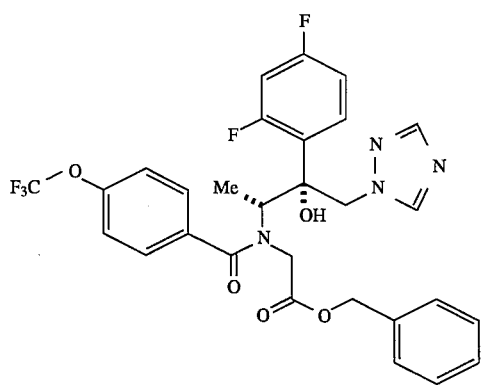

Following the procedure described in example 1, but starting from the compound obtained in reference example 8 and using 4-(trifluoromethoxy)benzoyl chloride instead of 4-(trifluoromethyl)benzoyl chloride, the title compound was obtained as a white solid.

mp: 153°–155° C.;

¹H NMR (80 MHz, CDCl₃) δ (TMS): 7.76 (s, 1H, triazole), 7.6-7.0 (m, triazole, arom), 6.9-6.5 (m, 2H, arom), 5.3-4.2 (m, 7H), 1.05 (d, J=6.2Hz, 3H, CHMe).

Analysis Calcd. for $C_{29}H_{25}F_5N_4O_5$: C 57.62; H 4.17; N 9.27. Found: C 57.74; H 3.97; N 9.06.

EXAMPLE 31 (UR-9727)

(2R*,3R*)-N-[3-(2,4-Difluorophenyl)-3-hydroxy-4-(1H-1,2,4-triazol-1-yl)-2-butyl]-N-[4-(trifluoromethoxy)benzoyl]glycine

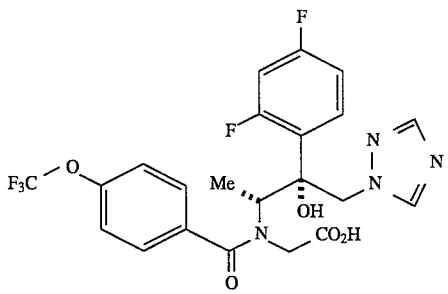

Following the procedure described in example 28, but starting from the compound obtained in example 30, the title compound was obtained as a white solid.

mp: 99°–105° C.;

¹H NMR (80 MHz, MeOH-d₄) δ (TMS): 8.19 (s, 1H, triazole), 7.8-7.0 (m, 6H, triazole, arom), 7.0-6.6 (m, 2H, arom), 5.2-4.2 (m, 5H), 1.10 (d, J=6.8Hz, 3H, CHMe).

Analysis Calcd. for $C_{22}H_{19}F_5N_4O_5$: C 51.37; H 3.72; N 10.89. Found: C 51.57; H 3.53; N 10.36.

EXAMPLE 32

(5R*,6R*)-6-[2,4-Difluorophenyl]-5-methyl-4-[4-(trifluoromethoxy)benzoyl]-6-(1H-1,2,4-triazol-1-yl)methyl]-2-morpholinone

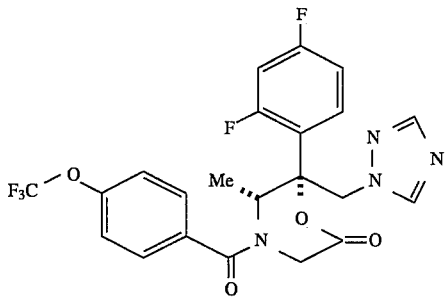

Following the procedure described in method A of example 29, but starting from the compound obtained in example 31, the title compound was obtained as a white solid.

mp: 180°–181° C.;

$^1$H NMR (80 MHz, CDCl$_3$) δ (TMS): 7.90 (s, 1H, triazole), 7.72 (s, 1H, triazole), 7.7-7.3 (m, 5H, arom), 7.1-6.7 (m, 2H, arom), 5.0-4.6 (m, 1H, CHMe), 4.81 (AB quartet, Δv=0.133, J=14.9Hz, 2H, CH$_2$Tr), 4.33 (s), 4.09 (s), 1.11 (d, J=6.9Hz, 3H, CHMe).

Analysis Calcd. for C$_{22}$H$_{17}$F$_5$N$_4$O$_4$: C 53.23; H 3.45; N 11.29. Found: C 53.10; H 3.33; N 11.02.

EXAMPLE 33

(2R*,3R*)-N-[3-(2,4-Difluorophenyl)-3-hydroxy-4-(1H-1,2,4-triazol-1-yl)-2-butyl]-N-[4-(2,2,2-trifluoroethoxy)benzoyl]glycine, benzyl ester

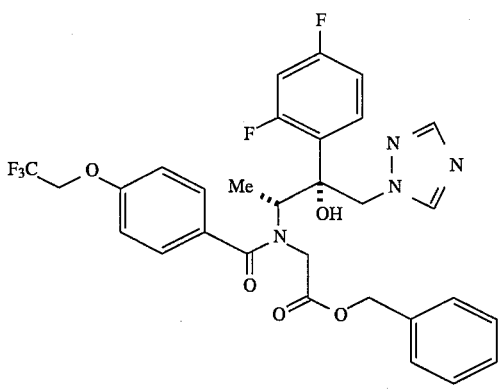

Following the procedure described in example 1, but starting from the compound obtained in reference example 8 and using 4-(2,2,2-trifluoroethoxy)benzoyl chloride instead of 4-(trifluoromethyl)benzoyl chloride, the title compound was obtained as a white solid.

mp: 135°–136° C.;

$^1$H NMR (80 MHz, CDCl$_3$) δ (TMS): 7.76 (s, 1H, triazole), 7.6-7.1 (m, triazole, arom), 7.0-6.6 (m, arom), 5.4-4.8 (m), 4.6-4.1 (m), 1.05 (d, J=6.8Hz, 3H, CHMe).

Analysis Calcd. for C30H27F$_5$N4O$_5$: C 58.25; H 4.40; N 9.06. Found: C 58.45; H 4.28; N 8.87.

EXAMPLE 34

(2R*,3R*)-N-[3-(2,4-Difluorophenyl)-3-hydroxy-4-(1H-1,2,4-triazol-1-yl)-2-butyl]-N-[4-(2,2,2-trifluoroethoxy)benzoyl]glycine

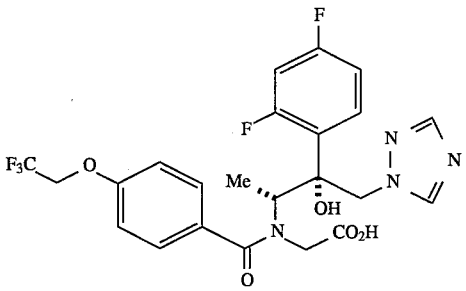

Following the procedure described in example 28, but starting from the compound obtained in example 33, the title compound was obtained as a white solid.

mp: 168°–177° C.;

$^1$H NMR (80 MHz, MeOH-d$_4$) δ (TMS): 8.19 (s, 1H, triazole), 7.7-7.4 (m, 3H, triazole, arom), 7.3-7.0 (m, 3H, arom), 7.0-6.6 (m, 2H, arom), 5.1-4.2 (m), 1.09 (d, J=6.8Hz, 3H, CHMe).

Analysis Calcd. for C$_{23}$H$_{21}$F$_5$N$_4$O$_5$: C 52.28; H 4.01; N 10.60. Found: C 52.09; H 3.98; N 10.53.

EXAMPLE 35

(SR*,6R*)-6-[2,4-Difluorophenyl]-5-methyl-4-[4-(2,2,2-trifluoroethoxy)benzoyl]-6-[(1H-1,2,4-triazol-1-yl)methyl]-2-morpholinone

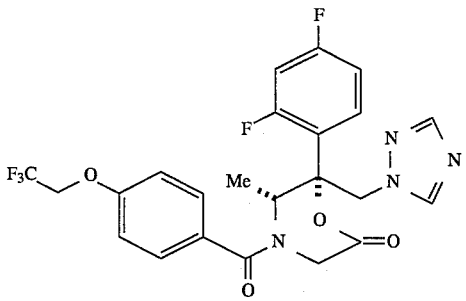

Following the procedure described in method A of example 29, but starting from the compound obtained in example 34, the title compound was obtained as a white solid.

mp: 162°–163° C.;

$^1$H NMR (80 MHz, CDCl$_3$) δ (TMS): 7.86 (s, 1H, triazole), 7.70 (s, 1H, triazole), 7.50 (d, J=8.7Hz, 2H, arom), 7.4-7.2 (m, 1H, arom), 7.06 (d, J=8.7Hz, 2H, arom), 6.9-6.7 (m, 2H, arom), 4.81 (AB quartet, Δv 0.171, J- 14.9Hz, 2H, CH$_2$Tr), 5.0- 4.6 (m, 1H, CHMe), 4.44 (q, J=8Hz, 2H, CH$_2$CF$_3$), 4.36 (s), 4.11 (s), 1.11 (d, J= 7Hz, 3H, CHMe);

Analysis Calcd. for C$_{23}$H$_{19}$F$_5$N$_4$O$_4$: C 54.12; H 3.75; N 10.98. Found: C 54.19; H 3.65; N 10.76.

EXAMPLE 36

(2R*,3R*)-N-[3-(2,4-Difluorophenyl)-3-hydroxy-4-(1H-1,2,4-triazol-1-yl)-2-butyl]-N-[4-(2,2,3,3-tetrafluoropropoxy)benzoyl]glycine, benzyl ester

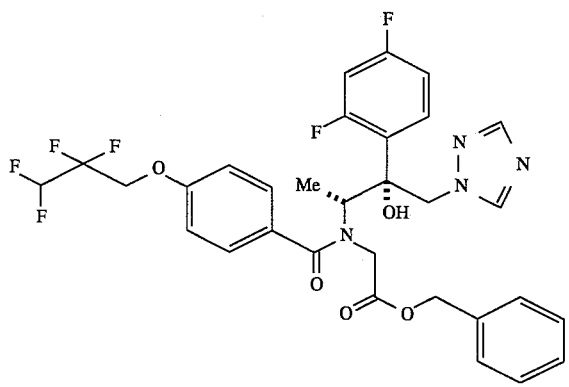

Following the procedure described in example 1, but starting from the compound obtained in reference example 8 and using 4-(2,2,3,3-tetrafluoropropoxy)benzoyl chloride (obtained according to patent EP 472392) instead of 4-(trifluoromethyl)benzoyl chloride, the title compound was obtained as a white solid.

mp: 133°–134° C.;

$^1$H NMR (80 MHz, CDCl$_3$) δ (TMS): 7.75 (s, 1H, triazole), 7.5-7.1 (m, triazole, arom), 7.34 (s, 5H, phenyl), 7.0-6.5 (m, arom), 6.06 (tt, J=4.7Hz, J=53Hz, 1H, CF$_2$H), 5.3-4.1 (m), 1.04 (d, J=6.8Hz, 3H, CHMe).

Analysis Calcd. for C$_{31}$H$_{28}$F$_6$N$_4$O$_5$: C 57.23; H 4.34; N 8.61. Found: C 57.29; H 4.35; N 8.50.

EXAMPLE 37

(2R*,3R*)-N-[3-(2,4-Difluorophenyl)-3-hydroxy-4-(1H-1,2,4-triazol-1-yl)-2-butyl]-N-[4-(2,2,3,3-tetrafluoropropoxy)benzoyl]glycine

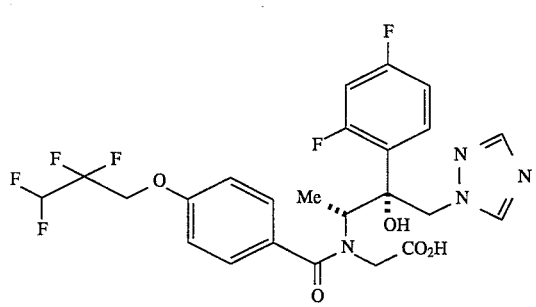

Following the procedure described in example 28, but starting from the compound obtained in example 36, the title compound was obtained as a white solid.

mp: 183°–184° C.;

$^1$H NMR (80 MHz, MeOH-d$_4$) δ (TMS): 8.18 (s, 1H, triazole), 7.66 (s, 1H, triazole), 7.6-7.4 (m, 2H, arom), 7.3-6.6 (m, 5H, arom), 6.34 (m, 1H, CF$_2$H), 5.2-4.2 (m), 1.09 (d, J=6.7Hz, 3H, CHMe).

Analysis Calcd. for C$_{24}$H$_{22}$F$_6$N$_4$O$_5$: C 51.43; H 3.96; N 9.00. Found: C 51.52; H 3.87; N 9.89.

EXAMPLE 38

(5R*,6R*)-6-[2,4-Difluorophenyl]-5-methyl-4-[4-(2,2,3,3-tetrafluoropropoxy)-benzoyl]-6-[(1H-1,2,4-triazol-1-yl)methyl]-2-morpholinone

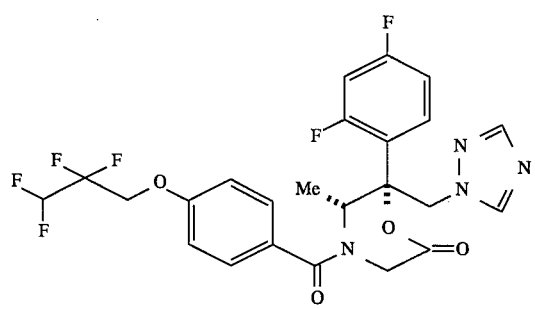

Following the procedure described in method A of example 29, but starting from the compound obtained in example 37, the title compound was obtained as a white solid.

mp: 78°–83° C.;

$^1$H NMR (80 MHz, CDCl$_3$) δ (TMS): 7.92 (s, 1H, triazole), 7.71 (s, 1H, triazole), 7.6-6.8 (m, 7H, arom), 6.07 (tt, J=4.6Hz, J=53Hz, 1H, CF$_2$H), 5.1-4.0 (m), 1.11 (d, J=7Hz, 3H, CHMe).

Analysis Calcd. for C$_{24}$H$_{20}$F$_6$N$_4$O$_4$: C 53.14; H 3.72; N 10.33. Found: C 53.10; H 3.79; N 9.75.

EXAMPLE 39

(2R*,3R*)-N-[3-(2,4-Dichlorophenyl)-3-hydroxy-4-(1H-1,2,4-triazol-1-yl)-2-butyl]-N-[4-(trifluoromethyl)benzoyl]glycine, benzyl ester

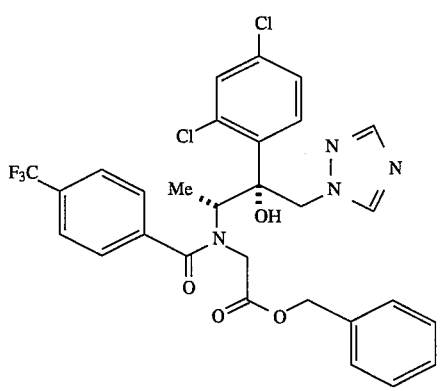

Following the procedure described in example 1, but using the compound obtained in reference example 10, the title compound was obtained as a white solid.

182°–183° C.;

¹H NMR (80 MHz, CDCl₃) δ (TMS): 7.86 (s, 1H, triazole), 7.75 (s, 1H, triazole), 7.38 (s, 5H, benzyl), 7.7-7.0 (m, 7H, arom), 6.2-5.7 (m), 5.27 (s, 2H, CH₂Ph), 5.3-4.7 (m), 4.64 (s, 1/2 CH₂CO), 4.30 (s, 1/2 CH₂CO), 1.03 and 1.00 (d, J= 7Hz, 3H, CHMe);

Analysis Calcd. for C₂₉H₂₅Cl₂F₃N₄O₄: C 56.05; H 4.05; N 9.02. Found: C 56.02; H 4.00; N 9.04.

EXAMPLE 40

(2R*,3R*)-N-[3-(2,4-Dichlorophenyl)-3-hydroxy-4-(1H-1,2,4-triazol-1-yl)-2-butyl]-N-[4-(trifluoromethyl)benzoyl]glycine

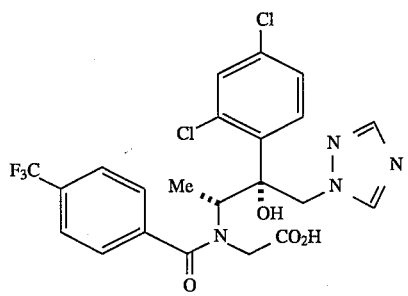

Following the procedure described in example 28, but starting from the compound obtained in example 39, the title compound was obtained as a white solid.

mp: 183°–189° C.;

¹H NMR (80 MHz, MeOH-d₄) δ (TMS): 8.26 and 8.17 (s, 1H, triazole), 8.0-7.6 (m, triazole, arom), 7.5-7.1 (m, arom), 6.4-6.1 (m), 5.9-5.5 (m), 5.05 (br s), 4.54 (s), 4.25 (s), 1.05 (d, J=6.9Hz, 3H, CHMe);

Analysis Calcd. for C₂₂H₁₉Cl₂F₃N₄O₄: C 49.73; H 3.60; N 10.54. Found: C 49.46; H 3.56; N 10.40.

EXAMPLE 41

(5R*,6R*)-6-[2,4-Dichlorophenyl]-5-methyl-4-[4-(trifluoromethyl)benzoyl]-6-(1H-1,2,4-triazol-1-yl)methyl]-2-morpholinone

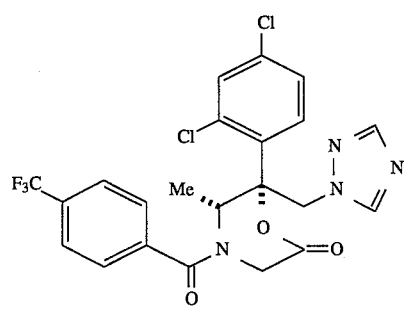

Following the procedure described in method A of example 29, but starting from the compound obtained in example 40, the title compound was obtained as a white solid.

mp: 184°–187° C.;

¹H NMR (80 MHz, CDCl₃) 15 (TMS): 7.9-7.3 (m, triazole, arom), 7.3-7.1 (m, 1H, arom), 5.5-4.9 (m, 1H, CHMe), 5.01 (AB quartet, Δv=0.444, J=14.8Hz, 2H, CH₂Tr), 4.29 (s), 4.05 (s), 1.08 (d, J=6.8Hz, 3H, CHMe);

Analysis Calcd. for C₂₂H₁₇Cl₂F₃N₄O₃: C 51.48; H 3.34; N 10.91. Found: C 51.76; H 3.40; N 10.75.

EXAMPLE 42

(2R*,3R*)-N-[3-(2,4-Dichlorophenyl)-3-hydroxy-4-(1H-1,2,4-triazol-1-yl)-2-butyl]-N-[4-(2,2,3,3-tetrafluoropropoxy)benzoyl]glycine, benzyl ester

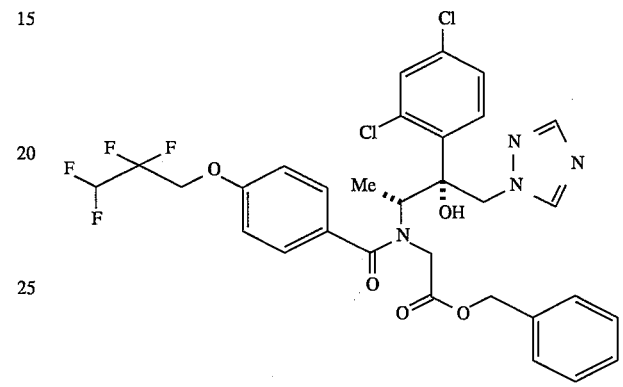

Following the procedure described in example 1, but starting from the compound obtained in reference example 10 and using 4-(2,2,3,3-tetrafluoropropoxy)benzoyl chloride (obtained according to patent EP 472392) instead of 4-(trifluoromethyl)benzoyl chloride, the title compound was obtained as a white solid.

mp: 69°–74° C.;

¹H NMR (80 MHz, CDCl₃) δ (TMS): 7.74 (s, 1H, triazole), 7.6-6.7 (m, triazole, arom), 6.06 (tt, J=4.6Hz, J=53Hz, 1H, CF₂H), 5.3-4.1 (m, 7H), 1.00 (d, J=6.9 Hz, 3H, CHMe).

Analysis Calcd. for C₃₁H₂₈Cl₂F₄N₄O₅: C 54.48; H 4.13; N 8.20. Found: C 54.21; H 4.17; N 8.11.

EXAMPLE 43

(2R*,3R*)-N-[3-(2,4-Dichlorophenyl)-3-hydroxy-4-(1H-1,2,4-triazol-1-yl)-2-butyl]-N-[4-(2,2,3,3-tetrafluoropropoxy)benzoyl]glycine

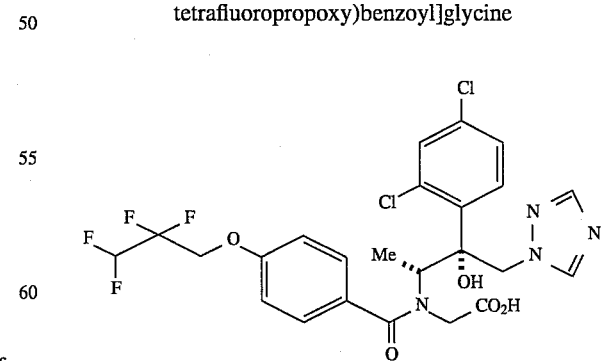

Following the procedure described in example 28, but starting from the compound obtained in example 42, the title compound was obtained as a white solid.

mp: 192°–193° C.;

$^1$H NMR (80 MHz, MeOH-d$_4$) δ (TMS): 8.15 (s, 1H, triazole), 7.67 (s, 1H, triazole), 7.6-7.0 (m, arom), 6.34 (tt, J=53Hz, J=4.8Hz, 1H, CF$_2$H), 6.4-6.0 (m), 5.8-5.5 (m), 5.31 (q, J=6.8Hz, 1H, CHMe), 4.98 (AB quartet, Δν=0.103, J=15Hz, 2H, CH$_2$Tr), 4.52 (s), 4.38 (s), 1.04 (d, J=6.8Hz, 3H, CHMe);

Analysis Calcd. for C$_{24}$H$_{22}$Cl$_2$F$_4$N$_4$O$_5$: C 48.58; H 3.74; N 9.44. Found: C 48.73; H 3.76; N 9.35.

EXAMPLE 44

(SR*,6R*)-6-[2,4-Dichlorophenyl]-5-methyl-4-[4-(2,2,3,3-tetrafluoropropoxy)-benzoyl]-6-[(1H-1,2,4-triazol-1-yl)methyl]-2-morpholinone

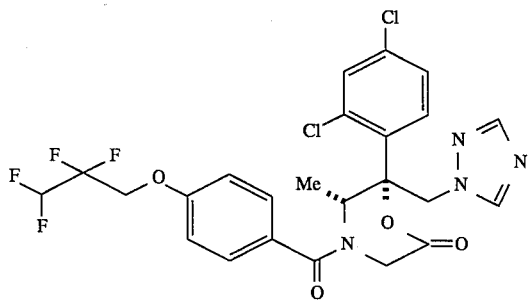

Following the procedure described in method A of example 29, but starting from the compound obtained in example 43, the title compound was obtained as a white solid.

mp: 88°–94° C.;

$^1$H NMR (80 MHz, CDCl$_3$) δ (TMS): 7.82 (s, 1H, triazole), 7.70 (s, 1H, triazole), 7.6-7.4 (m, arom), 7.3-6.9 (m, arom), 6.06 (tt, J=53Hz, J=4.5Hz, 1H, CF$_2$H), 5.23 (br s), 4.80 (s), 4.44 (br t, J=11.8Hz, 2H, CF$_2$CH$_2$), 4.33 (s), 4.10 (s), 1.08 (d, J=7Hz, 3H, CHMe);

Analysis Calcd. for C$_{24}$H$_{20}$Cl$_2$F$_4$N$_4$O$_4$: C 50.10; H 3.50; N 9.74. Found: C 50.14; H 3.56; N 9.50.

EXAMPLE 45

(2R*,3R*)-N-[3-[4-(Trifluoromethyl)phenyl]-3-hydroxy-4-(1H-1,2,4-triazol-1-yl)-2-butyl]-N-[4-(trifluoromethyl)benzoyl]glycine, benzyl ester

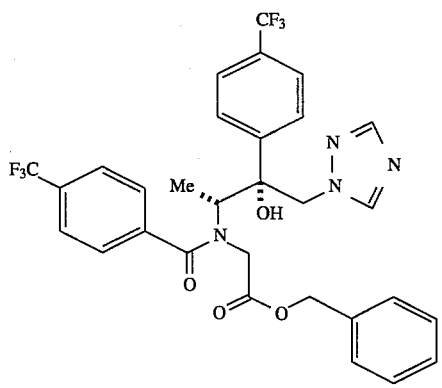

Following the procedure described in example 1, but starting from the compound obtained in reference example 21, the title compound was obtained as a white solid.

mp: 139°–140° C. (ether);

$^1$H NMR (80 MHz, CDCl$_3$) δ (TMS): 7.77 (s, 1H, triazole), 7.64 (s, 1H, triazole), 7.51 (br s, arom), 7.4-7.2 (m, arom), 5.5-5.1 (m, 1H, CHMe), 5.09 (s, 2H, CH$_2$Ph), 4.98 (br s, 2H, CH$_2$Tr), 4.31 (s, 2H, CH$_2$CO), 1.03 (d, J=7Hz, 3H, CHMe).

EXAMPLE 46

(2R*,3R*)-N-[3-[4-(Trifluoromethyl)phenyl]-3-hydroxy-4-(1H-1,2,4-triazol-1-yl)-2-butyl]-N-[4-(trifluoromethyl)benzoyl]glycine

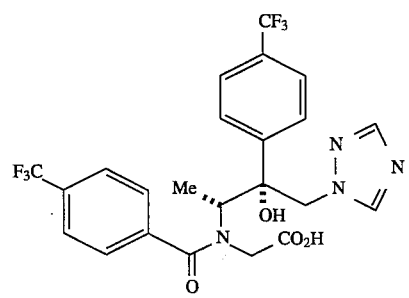

Following the procedure described in example 28, but starting from the compound obtained in example 45, the title compound was obtained as a white solid.

mp: 201°–204° C.;

$^1$H NMR (80 MHz, MeOH-d$_4$) δ (TMS): 8.16 (s, 1H, triazole), 7.9-7.5 (m, 9H, triazole, arom), 5.04 (s), 4.5-4.0 (m), 1.20 and 1.08 (d, J=7Hz, 3H, CHMe).

Analysis Calcd. for C$_{23}$H$_{20}$F$_6$N$_4$O$_4$: C 52.08; H 3.80; N 10.56. Found: C 52.78; H 3.78; N 10.65.

EXAMPLE 47

(5R*,6R*)-6-[4-(Trifluoromethyl)phenyl]-5-methyl-4-[4-(trifluoromethyl)-benzoyl]-6-[(1H-1,2,4-triazol-1-yl)methyl]-2-morpholinone

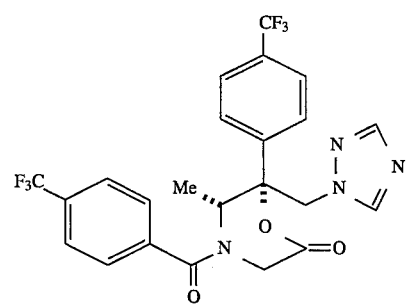

Following the procedure described in method A of example 29, but starting from the compound obtained in example 46, the title compound was obtained as a white solid.

mp: 189°–190° C.;

¹H NMR (80 MHz, CDCl₃) δ (TMS): 7.9-7.3 (m, 10H, triazole, arom), 4.73 (s), 4.5 -4.0 (m), 1.10 (d, J=6.9Hz, 3H, CHMe).

Analysis Calcd. for C₂₃H₁₈F₆N₄O₃: C 53.91; H 3.54; N 10.93. Found: C 54.23; H 3.71; N 10.76.

EXAMPLE 48

(2R*,3R*)-2-[2,4-Dichlorophenyl-3-[[N-[4-(trifluoromethyl)benzoyl]-N-(2-(1 H-1,2,4-triazol-1-yl)ethyl)]amino]-1-(1H-1,2,4-triazol-1-yl)-2-butanol

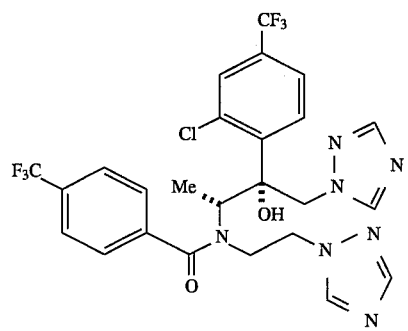

Following the acylation procedure described in example 1, but starting from the product obtained in reference example 27, the title product was obtained in a similar yield as a white solid.

mp: 91°–99° C.;

¹H NMR (80 MHz, CDCl₃) δ (TMS): 8.13 (s, 1H, triazole), 7.99 (s, 1H, triazole), 7.9-7.0 (m, triazole, arom), 5.5-5.0 (m), 4.9-4.1 (m), 0.9-0.6 (m, 3H, CHMe);

Analysis Calcd. for C₂₄H₂₂Cl₂F₃N₇O₂: C 50.72; H 3.90; N 17.25. Found: C 51.14; H 4.43; N 16.88.

EXAMPLE 49

(2R,3R)-N-[3-(2,4-Difluorophenyl)-3-hydroxy-4-(1H- 1,2,4-triazol-1-yl)-2-butyl]-N-[4-(trifluoromethyl)benzoyl]glycine, benzyl ester

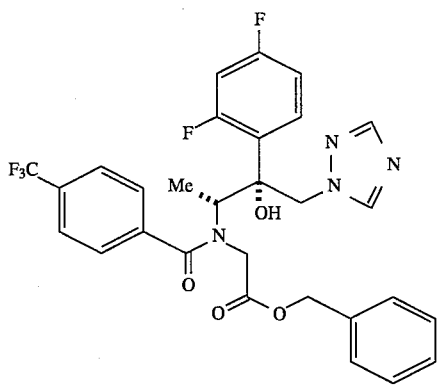

Following a procedure identical to that described in Example 26, but using the compound obtained in reference example 22, the title compound was prepared as a white solid. The NMR spectrum of the compound thus prepared matched with that of the compound obtained in example 26.

mp: 87°–89° C.;

[α]_D–63° (c=1, MeOH).

EXAMPLE 50

(2R,3R)-N-[3-(2,4-Dichlorophenyl)-3-hydroxy-4-(1H-1,2,4-triazol-1-yl)-2-butyl]-N-[4-(trifluoromethyl)benzoyl]glycine, benzyl ester

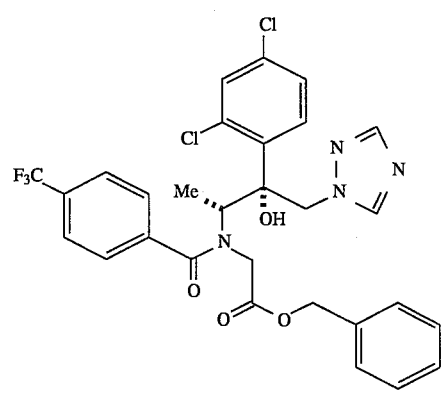

Following a procedure identical to that described in example 39, but using the compound obtained in reference example 23, the title compound was prepared as a white solid. The NMR spectrum of the compound thus prepared was identical to that of the compound obtained in example 39.

mp: 82°–86° C.;

[α]_D–76.3° (c=1, MeOH).

EXAMPLE 51

(2R,3R)-N-[3-(2,4-Difluorophenyl)-3-hydroxy-4-(1H-1,2,4-triazol-1-yl)-2-butyl]-N-[4-(trifluoromethyl)benzoyl]glycine

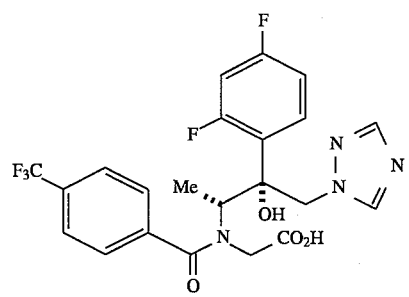

Following a procedure identical to that described in example 28, but using the compound obtained in example 49, the title compound was prepared as a white solid. The NMR spectrum of the compound thus prepared was identical to that of the compound obtained in example 28.

mp: 132°–135° C.;

[α]$_D$ –73.9° (c=1, MeOH).

EXAMPLE 52

(2R,3R)-N-[3-(2,4-Dichlorophenyl)-3-hydroxy-4-(1H-1,2,4-triazol-1-yl)-2-butyl]-N-[4-(trifluoromethyl)benzoyl]glycine

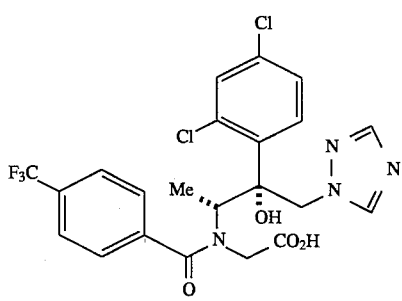

Following a procedure identical to that described in example 40, but using the compound obtained in example 50, the title compound was prepared as a white solid. The NMR spectrum of the compound thus obtained was identical to that of the compound prepared in example 40.

mp: 140°–142° C.;

[α]$_D$ –89.0° (c=1, MeOH).

EXAMPLE 53

(5R,6R)-6-[2,4-Difluorophenyl]-5-methyl-4-[4-(trifluoromethyl)1,2,4-triazol-1-yl)methyl]-2-morpholinone

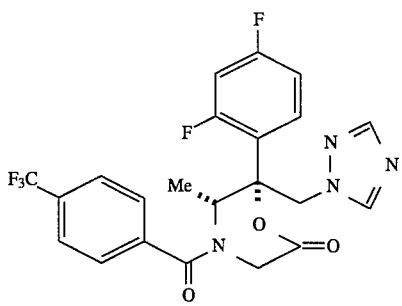

Following a procedure identical to that described in example 29, but using the compound obtained in example 51, the title compound was prepared as a white solid. The NMR spectrum of the compound thus prepared was identical to that of the compound obtained in example 29.

mp: 189°–190° C.;

[α]$_D$ –26.4° (c=1, MeOH).

EXAMPLE 54

(5R,6R)-6-[2,4-Dichlorophenyl]-5-methyl-4-[4-(trifluoromethyl)benzoyl]-12 4-triazol-1-yl)methyl]-2-morpholinone

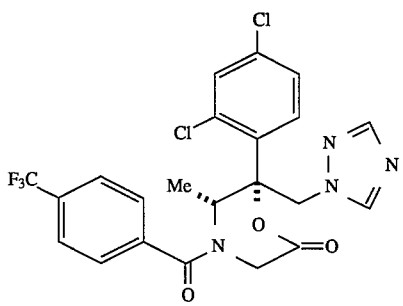

Following a procedure identical to that described in example 41, but using the compound obtained in example 52, the title compound was prepared as a white solid. The NMR spectrum of the compound thus prepared was identical to that of the compound obtained in example 41.

mp: 138°–139° C.;

[α]$_D$ –54.1° (c=1, MeOH)

EXAMPLE 55

(2R*,3R*)-N-[3-(2,4-Difluorophenyl)-3-hydroxy-4-(1H-1,2,4-triazol-1-yl)-2-butyl]-N-[4-(trifluoromethyl)benzoyl]-DL-alanine, benzyl ester

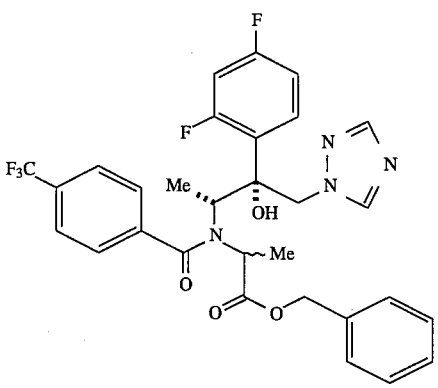

Following the procedure described in example 1, but starting from the compound obtained in reference example 24 and stirring the reaction at reflux for 20 h, the title compound was prepared as a yellowish solid in 32% yield.

mp: 70°–76° C.;

$^1$H NMR (80 MHz, CD$_3$OD) δ (TMS): 7.91 (s), 7.86 (s), 7.81 (s), 7.63 (s), 7.5-7.0 (complex signal), 6.71 (br tr, J=8.3Hz, arom), 5.31 (d, J=14 Hz, 1H, CH(H)), 5,27 (s, 2H, CH$_2$Ph), 5.06 (q, J=6.8Hz, 1H, CHMe), 4,58 (q, J=7.1Hz, 1H, CHMe), 4.15 (d, J=14Hz, 1H, CH(H)), 1.69 (d, J=7Hz, 3/2H, CHMe), 1.16 (d, J=7Hz, 3/2 H, CHMe).

Analysis Calcd. for C$_{30}$H$_{27}$F$_5$N$_4$O$_4$: C 59.80; H 4.52; N 9.30. Found: C 59.92; H 4.51; N 9.17.

EXAMPLE 56

(2R*,3R*)-N-[3-(2,4-Difluorophenyl)-3-hydroxy-4-(1H-1,2,4-triazol-1-yl)-2-butyl]-N-[4-(trifluoromethyl)benzoyl]-DL-alanine

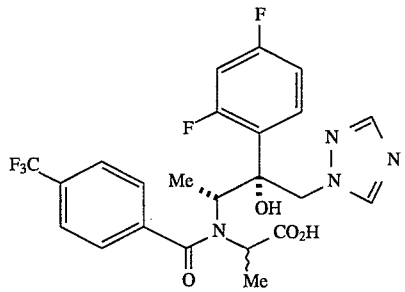

Following the hydrogenation procedure described in example 28, but starting from the compound obtained in example 55, the title compound was obtained in 80% yield.

mp: 219°–221° C.;

$^1$H NMR (80 MHz, CDCl$_3$+MeOH-d$_4$) δ (TMS): 8.09 (s, 1H, triazole), 7.9-7.5 (m, triazole, arom), 7.5-7.1 (m, 1H, arom), 7.0-6.5 (m, 2H, arom), 5.6 (d, J=14Hz, 1H, CH(H)), 5.93 (q, J=7Hz, 1H, CHMe), 4.65 (br q, J=7Hz, 1H, CHMe), 4.41 (d, J=14Hz, 1H, CH(H)), 1.69 (d, J=7Hz, 3/2H, CHMe), 1.18 (d, J=7Hz, 3/2H, CHMe).

Analysis Calcd. for C$_{23}$H$_{21}$F$_5$N$_4$O$_4$: C 53.91; H 4.13; N 10.93. Found: C 54.05; H 4.07; N 11.01.

EXAMPLE 57

(3RS,5R*,6R*)-6-[2,4-Difluorophenyl]-3,5-dimethyl-4-[4-(trifluoromethyl)-benzoyl]-6-[(1H-1,2,4-triazol-1-yl)methyl]-2-morpholinone

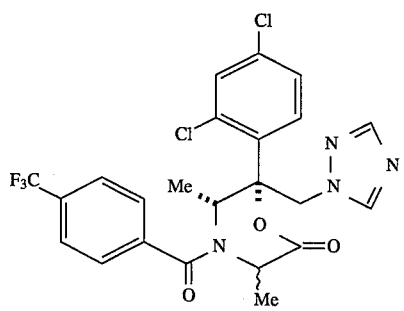

Following the procedure described in method A of example 29, but starting from the compound obtained in example 56, the title compound was obtained in 15% yield as a white solid.

mp: 176°–180° C.;

$^1$H NMR (80 MHz, CDCl$_3$) δ (TMS): 8.0-7.35 (m, 7H, triazole, arom), 7.5-7.0 (m, H, arom), 7.0-6.5 (m, 2H, arom), 5.6-4.4 (complex signal), 1.7-1.5 (m, CHMe.), 1.25 (d, J=7Hz, CHMe), 1.04 (d, J=7Hz, CHMe).

Analysis Calcd. for C$_{23}$H$_{19}$F$_5$N$_4$O$_3$: C 55.87; H 3.87; N 11.33 Found: C 55.44; H 4.04; N 11.44.

EXAMPLE 58

(2R*,3R*)-N-[3-(2,4-Difluorophenyl)-3-hydroxy-4-(1H-1,2,4-triazol-1-yl)-2-butyl]-N-[methanesulphonyl]glycine, benzyl ester

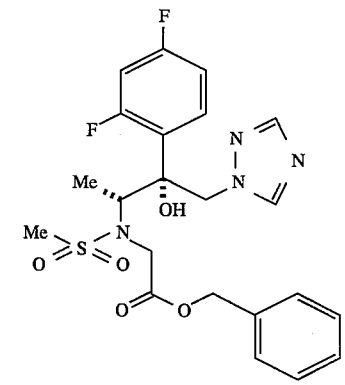

Following the procedure described in example 1, but starting from the compound obtained in reference example 8 and using methanesulphonyl chloride instead of 4-(trifluoromethyl)benzoyl chloride, the title compound was obtained as a white solid.

mp: 56°–59° C.;

$^1$H NMR (80 MHz, CDCl$_3$) δ (TMS): 7.46 (br s, 2H, triazole), 7.5-7.1 (m, 1H, arom), 7.36 (s, 5H, benzyl), 7.0-6.5 (m, 2H, arom), 5.30 (s), 5.15 (d, J=14.3Hz, 1H, CH(H)), 4.85 (d, J=14.3Hz, 1H, CH(H)), 4.52 (br s, 2H, CH$_2$), 4.6-4.3 (m, 1H, CHMe), 3.10 (s, 3H, SO$_2$Me), 1.03 (d, J=7Hz, 3H, CHMe).

EXAMPLE 59

(2R*,3R*)-N-[3-(2,4-Difluorophenyl)-3-hydroxy-4-(1H-1,2,4-triazol-1-yl)-2-butyl]-N-[methanesulphonyl]glycine

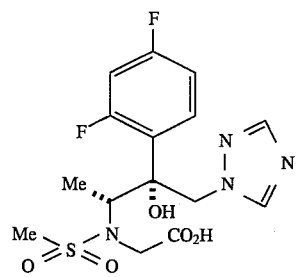

Following the procedure described in example 28, but starting from the compound obtained in example 58, the title compound was obtained as a white solid.

mp: 165°–173° C.;

$^1$H NMR (80 MHz, DMSO-d$_6$) δ (TMS): 8.21 (br s, 1H, triazole), 7.68 (br s, 1H, triazole), 7.4-6.8, complex signal, 3H, arom), 4.98 (AB q, Δv=0.34, J=14.3 Hz, 2H, TrCH2), 4.47 (q, J=7Hz, 1H, CHMe), 4.13 (s, 2H, CH$_2$CO$_2$H), 3.10 (s, 3H, SO$_2$Me), 0.91 (d, J=7Hz, 3H, Me).

Analysis Calcd. for C$_{15}$H$_{18}$F$_2$N$_4$O$_5$S: C 44.55, H 4.49, N 13.85, S 7.93. Found: C 43.01, H 4.61, N 12.41, S 7.50.

EXAMPLE 60

(5R *,6R * )-6-[2,4-Difluorophenyl]-5-methyl-4-(methanesulphonyl)-6-[ (1H-1,2,4-triazol-1-yl)methyl]-2-morpholinone

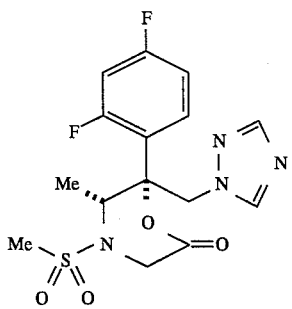

Following the procedure described in method A of example 29, but starting from the compound obtained in example 59, the title compound was obtained as a white solid.

mp: 180°–181° C.;

$^1$H NMR (80 MHz, CDCl$_3$) δ (TMS): 7.83 (s, 1H, triazole), 7.70 (s, 1H, triazole), 7.5-7.1 (m, 1H, arom), 7.1-6.7 (m, 2H, arom), 5.0-4.7 (m, 1H, CHMe), 4.92 (AB quartet, 2H, CH$_2$Tr), 4.68 (d, J=17Hz, 1H, CH(H)), 4.02 (d, J=17Hz, 1H, CH(H)) 3.05 (s, 3H, SO$_2$Me), 1.10 (d, J=7Hz, 3H, CHMe).

Analysis Calcd. for C$_{15}$H$_{16}$F$_2$N$_4$O$_4$S: C 46.63; H 4.17; N 14.50; S 8.30. Found: C 46.36; H 4.25; N 14.24; S 7.89.

EXAMPLE 61

(2R*,3R*)-N-[3-(2,4-Difluorophenyl)-3-hydroxy-4-(1H-1,2,4-triazol-1-yl)-2-butyl]-N-[2-fluoro-4-(trifluoromethyl)benzoyl]glycine, benzyl ester

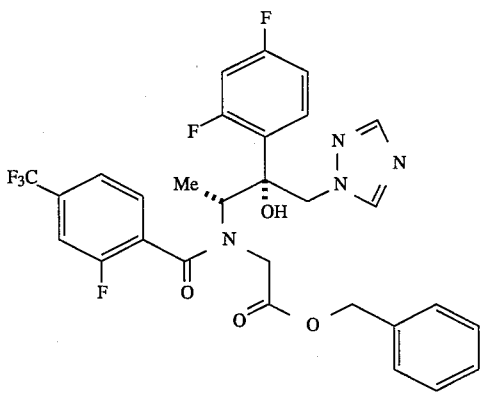

Following the procedure described in example 1, but starting from the compound obtained in reference example 8 and using 2-fluoro-4 -(trifluoromethyl)benzoyl chloride instead of 4-(trifluoromethyl)benzoyl chloride, the title compound was obtained as a white solid.

mp: 70°–73° C.;

$^1$H NMR (80 MHz, CD$_3$OD) δ (TMS): 7.80 (s), 7.76 (s), 7.7-7.0 (complex signal, arom H), 7.0-6.5 (complex signal, 2H, arom), 5.60 (q, J=7 Hz, 1H, CHMe), 5,27 (s), 5.15 (s), 5.03 (s), 4.93 (s), 4.7-4.5 (m), 4.3-4.2 (m), 1.07 and 1.02 (two d, J= 7Hz, 3H, Me).

Analysis Calcd. for C$_{29}$H$_{24}$F$_6$N$_4$O$_4$: C 57.43; H 3.99; N 9.24. Found: C 57.42; H 4.02; N 9.06.

EXAMPLE 62

(2R*,3R*)-N-[3-(2,4-Difluorophenyl)-3-hydroxy-4-(1H-1,2,4-triazol-1-yl)-2-butyl]-N-[2-fluoro-4-(trifluoromethyl)benzoyl]glycine

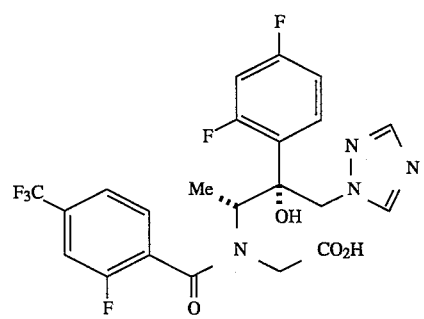

Following the hydrogenation procedure described in example 28, but starting from the compound obtained in example 61, the title compound was obtained in 100% yield.

mp: 191°–192° C.;

$^1$H NMR (80 MHz, MeOH-d$_4$) δ (TMS): 8.21 (d, J=3.7 Hz, 1H, arom), 7.9-7.7 (m, 4H, triazole, arom), 7.5-7.1 (m, 1H, arom), 7.1-6.5 (m, 2H, arom), 5.72 (q, J=7Hz, 1H, CHMe), 5.07 (AB q, 2H, CH$_2$Tr), 4.49 (s), 4.28 (s), 1.11 and 1.06 (d, J=7Hz, 3Me).

Analysis Calcd. for C$_{22}$H$_{18}$F$_6$N$_4$O$_4$: C 51.91; H 3.51; N 10.85. Found: C 51.80; H 3.69; N 10.13.

EXAMPLE 63

(5R*,6R*)-6-[2,4-Difluorophenyl]-5-methyl-4-[2-fluoro-4-(trifluoromethyl)-benzoyl]-6-[(1H-1,2,4-triazol-1-yl)methyl]-2-morpholinone

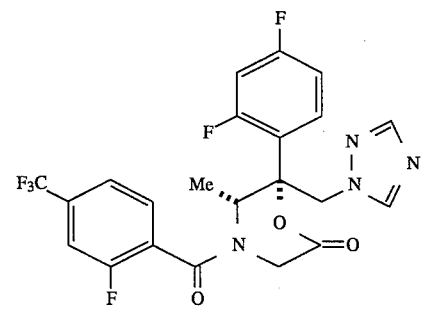

Following the cyclization procedure described in example 29, but starting from the compound obtained in example 62, the title compound was obtained in 82 % yield as a white solid.

mp: 191°–192° C.;

¹H NMR (80 MHz, CDCl₃) δ (TMS): 8.0-7.35 (m, 6H, triazole, arom), 7.2-6.6 (m, 2H, arom), 5.84 (br q, J=7 Hz, 1H, CHMe), 5.1-4.3 (complex signal, 3H), 4.20 (s), 1.13 and 1.05 (d, J=7Hz, 3H, Me).

Analysis Calcd. for C₂₂H₁₆F₆N₄O₃: C 53.02; H 3.24; N 11.24 Found: C 52.99; H 3.31; N 11.24.

EXAMPLE 64

(5R*,6R*)-6-[2,4-Difluorophenyl]-5-methyl-4-[4-(trifluoromethyl)benzoyl]-6 -[(1H-1,2,4-triazol-1-yl)methyl]morpholine

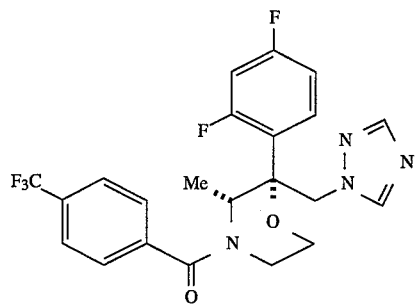

A solution containing (2R*,3R*)-2-[2,4-difluorophenyl]-3-[N-(2 -hydroxyethyl)-N-[4-(trifluoromethyl)benzoyl]amino]-1-(1H-1,2,4-triazol-1 -yl)-2-butanol (500 mg, 1.03 mmol, obtained in example 3) in THF was treated with diethylazadicarboxylate (262 mg, 1.5 eq) and triphenylphosphine (393 mg, 1.5 eq) at room temperature for 24 h. The volatiles were removed in vacuo and the orange oily residue was purified by flash chromatography to afford the title compound as a colorless wax (209 mg, 45 % yield).

¹H NMR (80 MHz, CDCl₃) δ (TMS): 8.0-7.1 (m, 6H, triazole, arom), 7.1-6.6 (m, 2H, arom), 5.50 (br q, J=7 Hz, 1H, CHMe), 5.32 (br s), 5.13 (br s), 4.9-3.3 (complex signal, 3H), 1.12 (br d, J=7Hz, 3H, Me). MS (CI, CH₄) 467 (M+1)

EXAMPLE 65

(2R*,3R*)-N-[3-(2,4-Difluorophenyl)-3-hydroxy-4-(1H-1,2,4-triazol-1-yl)-2 -butyl]-N-[4-(trifluoromethyl)benzoyl]glycinamide

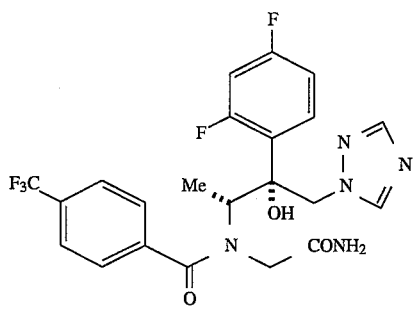

To a solution of (5R*,6R*)-6-[2,4-difluorophenyl]-5-methyl-4-[4 -(trifluoromethyl)benzoyl]-6-[(1H-1,2,4-triazol-1-yl)methyl]-2-morpholinone (0.5 g, 1 mmol) (obtained in example 29) in acetone (15 mL) was added dropwise 30% ammonium hydroxide (5 mL) and the mixture was stirred at room temperature during 1 h. The volatiles were removed under reduced pressure and the residue was partitioned between 1N NaHCO₃ and chloroform. The organic phase was separated, dried over anhydrous sodium sulfate, the drying agent was filtered and the solvent removed in vacuo to afford the title product as a white solid (0.38 g, 80%).

mp: 147°-148° C.;

¹H NMR (80 MHz, MeOH-d4) δ (TMS): 7.86 (s, triazole), 7.8-7.5 (m, triazole, arom), 7.5-7.0 (m, 1H, arom), 6.9-6.5 (m, 2H, arom), 6.21 (br s, 2H, NH2), 5.8- 4.7 (complex signal), 4.65 (br q, J=7Hz, CHMe), 4.49 (br s), 4.35 (s), 4.17 (s), 1.08 (br d, J=7Hz, 3H, CHMe);

Analysis Calcd. for C₂₂H₂₀F₅N₅O₃: C 53.12; H 4.05; N 14.08. Found: C 53.35; H 4.04; N 13.50.

EXAMPLE 66

In vivo activity

According to an in vivo systemic candidiasis model in mice described in EP 332,387 in which all the the animals of the control group died within 3 days after inoculation, 90% to 100% of the animals treated with 20 mg/kg p.o. at times 1, 4 and 24 h after inoculation with the products of examples 1, 2, 3, 4, 5, 6, 7, 8, 9, 10, 11, 12, 13, 14, 19, 21, 23, 25, 29, 32, 35, 38, 41, 44, 49, 50, 53, 54, 57 and 63 survived at the end of the study (day 10). Under these experimental conditions, the known compound fluconazole at 20 mg/kg showed a 80–90% protection.

We claim: a salt or solvate thereof.

1. A compound of the formula

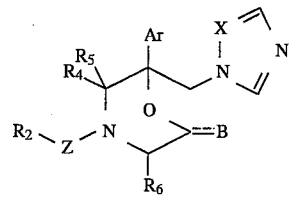

as a racemate, a diastereoisomer mixture or as a homochiral compound wherein:

X is CH or N;

Ar represents phenyl or a phenyl ring substituted with one or more halogen and/or trifluoromethyl groups;

Z is —C (=O)— or —SO₂—;

B is O, in which case the dotted line represents a covalent bond, or B is hydroxy, fluorine, hydrogen or 1-H-1,2,4 -triazol-1-yl, in which case the dotted line is absent;

R₄ is C₁₋₄ alkyl;

R₅, and R₆, are independently hydrogen or C₁₋₄ alkyl;

when Z is —C(=O)—, R₂ is phenyl, phenyl substituted with one or more groups R₁₀, or naphthyl;

when Z is —SO₂—, R₂ is C₁₋₄-alkyl, phenyl—C₁₋₄-alkyl, phenyl or phenyl substituted with one or more groups R₁₀;

R₁₀ represents C₁-C₄ alkyl, C₁-C₄ haloalkyl, C₁-C₄ alkoxy, C₁-C₄ haloalkoxy, halogen, nitro, cyano, hydroxy, benzyloxy, hydroxymethyl, a group of formula —CH₂—OCO—(C₁₋₄ alkyl), a group of formula —CO— (C₁₋₄ alkyl), a group of formula —COO—(C₁₋₄ alkyl), a group of formula —SO₂(C₁₋₄ Alkyl) wherein z is 0, 1 or 2, amino, mono- or dialkylamino wherein alkyl means C₁-C₄ alkyl; or a salt or solvate thereof.

2. A compound according to claim 1 wherein:
X is N;
$R_2$ is phenyl or phenyl substituted with one or more groups $R_{10}$; and
Ar, Z, $R_4$, $R_5$, $R_6$ and $R_{10}$ have the previously defined meaning.

3. A compound according to claim 1 wherein:
X is N;
Z is —C(=O)—;
$R_2$ is phenyl or phenyl substituted with one or more groups $R_{10}$; and
Ar, $R_4$, $R_5$, $R_6$ and $R_{10}$ have the previously defined meaning.

4. A compound according to claims 2 wherein:
X is N;
Z is —C(=O)—;
$R_2$ is phenyl or phenyl substituted with one or more groups $R_{10}$;
$R_4$ is methyl;
$R_5$ is hydrogen or methyl; and
Ar, $R_6$ and $R_{10}$ have the previously defined meaning.

5. A compound according to claim 1 wherein:
X is N;
Z is —C(=O)—;
$R_2$ is 4-chlorophenyl, 4-fluorophenyl, 4-(trifluoromethyl)phenyl, 2-fluoro-4-(trifluoromethyl)phenyl, 4-cyanophenyl, 4-nitrophenyl, 4-(trifluoromethoxy)phenyl, 4-(2,2,2-trifluoroethoxy)phenyl or 4-(2,2,3,3-tetrafluoropropoxy)phenyl;
$R_4$ is methyl;
$R_5$ is hydrogen;
Ar is 4-fluorophenyl, 2-chloro-4-fluorophenyl, 2,4-dichlorophenyl, 2,4-difluorophenyl, 4-(trifluoromethyl)phenyl or 4-chlorophenyl; and
$R_6$ is hydrogen.

6. A compound according to claim 1 wherein:
X is N;
Z is —C(-O)—;
$R_2$ is 4-chlorophenyl, 4-fluorophenyl, 4-(trifluoromethyl)phenyl, 2-fluoro-4-(trifluoromethyl)phenyl, 4-cyanophenyl, 4-nitrophenyl, 4-(trifluoromethoxy)phenyl, 4-(2,2,2-trifluoroethoxy)phenyl or 4-(2,2,3,3-tetrafluoropropoxy)phenyl;
$R_4$ is methyl;
$R_5$ is hydrogen;
B is O in which case the dotted line represents a covalent bond, or B is hydroxy, in which case the dotted line is absent;
Ar is 4-fluorophenyl, 2-cloro-4-fluorophenyl, 2,4-dichlorophenyl, 2,4-difluorophenyl, 4-(trifluoromethyl)phenyl or 4-chlorophenyl; and
$R_6$ is hydrogen.

7. A compound according to claim 5 wherein:
X is N;
Z is —C(=O)—;
$R_2$ is 4-chlorophenyl, 4-fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl or 4-(2,2,3,3-tetrafluoropropoxy)phenyl;
$R_4$ is methyl;
$R_5$ is hydrogen;
Ar is 2,4-dichlorophenyl, 2,4-difluorophenyl, 4-(trifluoromethyl)phenyl or 4-chlorophenyl; and
$R_6$ is hydrogen.

8. A compound according to claim 6 wherein
X is N;
Z is —C(=O)—;
$R_2$ is 4-chlorophenyl, 4-fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl or 4-(2,2,3,3-tetrafluoropropoxy)phenyl;
$R_4$ is methyl;
$R_5$ is hydrogen;
B is O in which case the dotted line represents a covalent bond;
Ar is 2,4-dichlorophenyl, 2,4-difluorophenyl, 4-(trifluoromethyl)phenyl or 4-chlorophenyl; and
$R_6$ is hydrogen.

9. A compound according to claim 6 wherein:
X is N;
Z is —C(=O)—;
$R_2$ is 4-chlorophenyl, 4-fluorophenyl, 4-(trifluoromethyl)phenyl, 2-fluoro-4-(trifluoromethyl)phenyl, 4-(trifluoromethoxy)phenyl, 4-(2,2,2-trifluoroethoxy)phenyl or 4-(2,2,3,3-tetrafluoropropoxy)phenyl;
$R_4$ is methyl;
$R_5$ is hydrogen;
B is hydroxy, in which case the dotted line is absent;
Ar is 2,4-dichlorophenyl, 2,4-difluorophenyl, 4-(trifluoromethyl)phenyl or 4-chlorophenyl; and
$R_6$ is hydrogen.

10. (SR*,6R*)-6-[2,4-Difluorophenyl]-5-methyl-4-[4-(trifluoromethyl)benzoyl]-6-[(1H-1,2,4-triazol-1-yl)methyl]-2-morpholinone or a salt or solvate thereof.

11. (SR,6R)-6-[2,4-Difluorophenyl]-5-methyl-4-[4-(trifluoromethyl)benzoyl]-6-(1H-1,2,4-triazol-1-yl)methyl]-2-morpholinone or a salt or solvate thereof.

12. (SR*,6R*)-6-[2,4-Dichlorophenyl]-5-methyl-4-[4-(trifluoromethyl)benzoyl]-6-[(1H-1,2,4-triazol-1-yl)methyl]-2-morpholinone or a salt or solvate thereof.

13. (5R,6R)-6-[2,4-Dichlorophenyl]-5-methyl-4-[4-(trifluoromethyl)benzoyl]-6-(1H-1,2,4-triazol-1-yl)methyl]-2-morpholinone or a salt or solvate thereof.

14. (5R*,6R*)-6-[2,4-Difluorophenyl]-5-methyl-2-hydroxy-4-[4-(trifluoromethyl)benzoyl]-6-[(1H-1,2,4-triazol-1-yl)methyl]morpholine or a salt or solvate thereof.

15. (SR,6R)-6-[2,4-Difluorophenyl]-5-methyl-2-hydroxy-4-[4-(trifluoromethyl)-benzoyl]-6-[(1H-1,2,4-triazol-1-yl)methyl]morpholine or a salt or solvate thereof.

16. (5R*,6R*)-6-[2,4-Dichlorophenyl]-5-methyl-2-hydroxy-4-[4-(trifluoromethyl)benzoyl]-6-[(1H-1,2,4-triazol-1-yl)methyl]morpholine or a salt or solvate thereof.

17. (SR,6R)-6-[2,4-Dichlorophenyl]-5-methyl-2-hydroxy-4-[4-(trifluoromethyl)-benzoyl]-6-[(1H-1,2,4-triazol-1-yl)methyl]morpholine or a salt or solvate thereof.

18. (5R*,6R*)-6-[2,4-Difluorophenyl]-5-methyl-4-[2-fluoro-4-(trifluoromethyl)-benzoyl]-6-[(1H-1,2,4-triazol-1-yl)methyl]-2-morpholinone or a salt or solvate thereof.

19. (5R,6R)-6-[2,4-Difluorophenyl]-5-methyl-4-[2-fluoro-4-(trifluoromethyl)-benzoyl]-6-[(1H-I,2,4-triazol-]-yl)methyl]-2-morpholinone or a salt or solvate thereof.

20. (5R*,6R*)-6-[2,4-Difluorophenyl]-5-methyl-4-[4-(trifluoromethyl)benzoyl]-6-[(1H-1,2,4-triazol-1-yl)methyl]morpholine, or a pharmaceutically acceptable salt or solvate thereof.

21. (5R,6R)-6-[2,4-Difluorophenyl]-5-methyl-4-[4 -(trifluoromethyl)benzoyl]6[(1H-1,2,4-triazol-1 -yl)methyl]morpholine, or a pharmaceutically acceptable salt or solvate thereof.

22. (5R*,6R*)-6-[2,4-Difluorophenyl]-5-methyl-4-[4 -(trifluoromethyl)benzoyl]-6-[(1H-1, 2,4-triazol-1 -yl) methyl]morpholine ethanolate.

23. (5R,6R)-6-[2,4-Difluorophenyl]-5-methyl-4-[4 -(trifluoromethyl)benzoyl]-6-[(1H-1,2,4-triazol-1 -yl) methyl] morpholine ethanolate.

24. (5R*,6R*)-6-[2,4-Difluorophenyl]-5-methyl-2 -hydroxy-4-[4-(trifluoromethyl)benzoyl]-6-[(1H-1, 2,4-triazol-1 -yl) methyl]morpholine ethanolate.

25. (5R,6R)-6-[2,4-Difluorophenyl]-5-methyl-2-hydroxy-4-[4 -(trifluoromethyl)benzoyl]-6-[(1H-1,2,4-triazol-1 -yl)methyl]morpholine ethanolate.

26. A pharmaceutical composition which comprises an effective amount of a compound as defined in claim 1 or a pharmaceutically acceptable salt or solvate thereof in admixture with a pharmaceutically acceptable excipient.

27. A method for treating or preventing fungal infections in an animal, which may be a human being, which comprises administering to an animal in need thereof an effective amount of a compound as defined in claim 1 or a pharmaceutically acceptable salt or solvate thereof.

28. An agrochemical composition comprising an effective amount of a compound as defined in claim 1 or a salt or solvate thereof in admixture with an agronomically acceptable excipient.

29. A method of combatting fungal diseases in a plant which comprises administering to the plant an effective amount of a compound as defined in claim 1 or a salt or solvate thereof.

* * * * *

UNITED STATES PATENT AND TRADEMARK OFFICE
CERTIFICATE OF CORRECTION

PATENT NO. : 5,478,826
DATED : December 26, 1995
INVENTOR(S) : Javier Bartroli et al.

It is certified that error appears in the above-indentified patent and that said Letters Patent is hereby corrected as shown below:

Col. 2, line 20, "or salt" should be -- of said --; Col. 2, lines 21-22, delete "forms a six-membered ring of formula I"; Col. 3, line 30, "R1" should be -- $R_1$ --; Col. 5, line 17, "salt compound or" should be -- said compound of --; Col. 9, line 14, "as seen in" should be -- of --; Col. 9, line 15, "of" should be -- as seen in --; Col. 10, lines 14-15, delete "as formula I wherein $R_1=CO_2H$) using an appropriate dehydrating agent,"; Col. 12, line 19, after "process" insert -- can be easily scaled up and allows the recycling of the chiral auxiliary. It is --; Col. 15, line 62, after "Magnesium" insert -- stearate --; Col. 16, line 24, "-1-1-yl)" should be -- -1-yl) --; Col. 17, line 23, "-)2,4-" should be -- -(2,4- --; Col. 18, line 15, "C21H24Cl2N3O2" should be -- $C_{21}H_{24}Cl_2N_3O_2$ --; Col. 18, line 59, "1Hm" should be -- 1H --; Col. 19, line 20, after "example" insert -- 5 --; Col. 19, line 67, "3H, Me" should be

UNITED STATES PATENT AND TRADEMARK OFFICE
CERTIFICATE OF CORRECTION

PATENT NO. : 5,478,826
DATED : December 26, 1995
INVENTOR(S) : Javier Bartroli et al.

It is certified that error appears in the above-indentified patent and that said Letters Patent is hereby corrected as shown below:

-- 3H, CHMe --; Col. 20, line 3, "[3-(2,4-diflurophenyl)" should be --[3-(2,4-Difluorophenyl)--; Col. 21, line 5, "OCH?CH3)" should be -- $OCH_2CH_3$) --; Col. 21, line 59, "a" should be -- an --; Col. 21, line 67, after "ice" delete "cooled to 0° C and poured carefully to a" and insert -- (150 mL). --; Col. 22, line 1, delete "mixture of 1N HCl (750 mL) and ice"; and insert -- The mixture was concentrated and the aqueous residue extracted --; same line, after "$CH_2Cl_2$.", delete "The"; Col. 22, lines 2-3, delete "organic layer was washed with 5% aqueous $NaHCO_3$ and with $CH_2Cl_2$"; Col. 22, line 5, after "and" insert -- the filtrate concentrated to a brown oil (117.78 g, 100% mass balance). --; Col. 24, line 3, "2-[2-(Tetrahydropyran" should be -- 2-[1-(Tetrahydropyran --; Col. 25, line 4, after "1H" insert a comma; Col. 25, line 6, after "C 51.83" insert a semicolon; Col. 26, line 20, before "CHMe" insert -- 3H, --; Col. 26, line 56, "0,175" should be -- 0.175 --; Col. 27, the chemical compound

UNITED STATES PATENT AND TRADEMARK OFFICE
CERTIFICATE OF CORRECTION

PATENT NO. : 5,478,826
DATED : December 26, 1995
INVENTOR(S) : Javier Bartroli et al.

It is certified that error appears in the above-indentified patent and that said Letters Patent is hereby corrected as shown below:

for "REFERENCE EXAMPLE 22" should be replaced with --

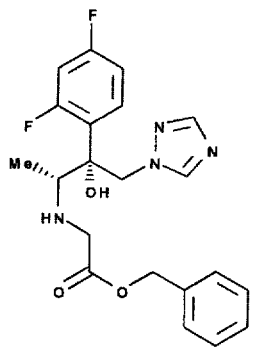

--; Col. 28, line 24, "pre-pared"

UNITED STATES PATENT AND TRADEMARK OFFICE
CERTIFICATE OF CORRECTION

PATENT NO. : 5,478,826
DATED : December 26, 1995
INVENTOR(S) : Javier Bartroli et al.

It is certified that error appears in the above-indentified patent and that said Letters Patent is hereby corrected as shown below:

should be -- prepared --; Col. 28, the chemical compound for "REFERENCE EXAMPLE 24" should be replaced with --

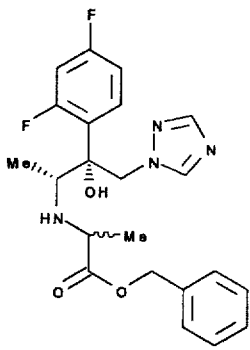

--; Col. 28, line 56, "10" should be -- 8 --; Col. 29, line 3, "(4R*,SR*)" should be -- (4R*,5R*) --; Col. 29, line 4, "(2,4-5" should be -- (2,4- --;

UNITED STATES PATENT AND TRADEMARK OFFICE
CERTIFICATE OF CORRECTION

PATENT NO. : 5,478,826

DATED : December 26, 1995

INVENTOR(S) : Javier Bartroli et al.

It is certified that error appears in the above-indentified patent and that said Letters Patent is hereby corrected as shown below:

Col. 29, line 33, "3,92" should be -- 3.92 --; Col. 29, line 41, "(4R*,SR*)" should be -- (4R*,5R*) --; Col. 29, line 59, "0,286 g" should be -- 0.286 g --; Col. 30, line 11, "(2,4-dichloro" should be -- (2,4-dichlorophenyl)-1- --; Col. 30, line 57, "(45)" should be -- (4S) --; Col. 30, line 59, "(45)" should be -- (4S) --; Col. 31, line 20, "CH(HH)Ph)" should be -- CH(H)Ph) --; Col. 31, line 21, "CH(HH))" should be -- CH(H)) --; Col. 31, line 21, "1,19" should be -- 1.19 --; Col. 31, line 63, "CO2H" should be -- $CO_2H$ --; Col. 31, line 66, "$J_cF=0.8$ Hz" should be -- $J_{CF}=0.8$ Hz --; Col. 32, line 20, "Nail" should be -- NaH --; Col. 38, line 40, "$C_{22}H_{21}C_{12}F_3N_4O_3$" should be -- $C_{22}H_{21}Cl_2F_3N_4O_3$ --; Col. 39, line 19, "(1H-1,2A-" should be -- (1H-1,2,4- --; Col. 39, line 60, "[2,4-dichlorophenyl]-1" should be -- [2,4-dichlorophenyl]-1-(1H --; Col. 42, line 65, "CMe" should be -- CHMe --; Col. 45, line 64, "$C_{22}H_{19}C_{12}F_3N_4O_3$" should be

UNITED STATES PATENT AND TRADEMARK OFFICE
CERTIFICATE OF CORRECTION

PATENT NO. : 5,478,826  Page 6 of 9
DATED : December 26, 1995
INVENTOR(S) : Javier Bartroli et al.

It is certified that error appears in the above-indentified patent and that said Letters Patent is hereby corrected as shown below:

-- $C_{22}H_{19}Cl_2F_3N_4O_3$ --; Col. 46, line 3, "(SR*,6R*)" should be -- (5R*,6R*) --; Col. 46, line 37, "$C_{24}H_{20}C_{12}F_3N_7O_2$" should be -- $C_{24}H_{20}Cl_2F_3N_7O_2$ --; Col. 46, line 61, "$CH_2C_{12}$" should be -- $CH_2Cl_2$ --; Col. 48, line 11, "OCH?CH3)" should be -- $OCH_2CH_3$) --; Col. 48, line 54, "MeOH-d4" should be -- MeOH-$d_4$ --; Col. 52, line 1, "C3OH27F5N4O5" should be --$C_{30}H_{27}F_5N_4O_5$ --; Col. 52, line 37, "(SR*,6R*)" should be --(5R*,6R*) --; Col. 57, line 13, "(SR*,6R*)" should be --(5R*,6R*) --; Col. 58, line 16, "(trifluorornethyl)" should be -- (trifluoromethyl) --; Col. 59, the chemical compound for "EXAMPLE 48" should be replaced with

UNITED STATES PATENT AND TRADEMARK OFFICE
CERTIFICATE OF CORRECTION

PATENT NO. : 5,478,826

DATED : December 26, 1995

INVENTOR(S) : Javier Bartroli et al.

It is certified that error appears in the above-indentified patent and that said Letters Patent is hereby corrected as shown below:

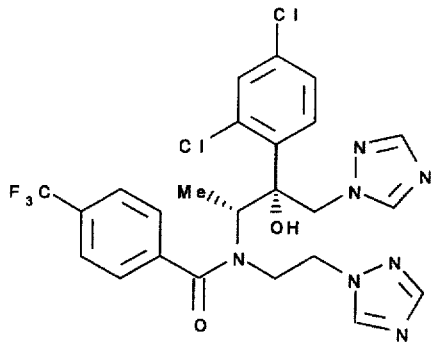

-- --; Col. 61, line 43, "(trifluoromethyl)" should be -- (trifluoromethyl)benzoyl]-6-[(1H- --; Col. 62, line 4, "(trifluoromethyl)benzoyl]-12" should be -- (trifluoromethyl)benzoyl]-6-[(1H-1,2,4- --; Col. 62, line 62, "5,27" should be -- 5.27 --; Col. 62, line 63, "4,58" should be -- 4.58 --; Col. 63, the chemical compound for "EXAMPLE 57"

UNITED STATES PATENT AND TRADEMARK OFFICE
CERTIFICATE OF CORRECTION

PATENT NO. : 5,478,826
DATED : December 26, 1995
INVENTOR(S) : Javier Bartroli et al.

It is certified that error appears in the above-indentified patent and that said Letters Patent is hereby corrected as shown below:

should be replaced with --

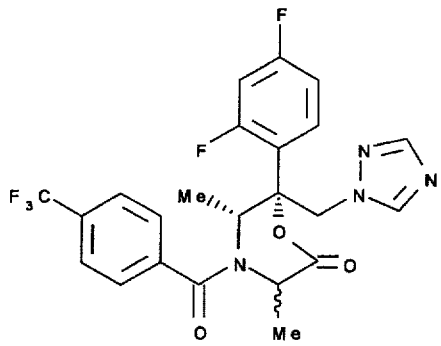

--; Col. 63, line 66, "$C_{23}H_{19}F_5N4O_3$" should be -- $C_{23}H_{19}F_5N_4O_3$ --; Col. 66, line 3, "5,27" should be -- 5.27 --; Col. 68, line 30, after "We claim:" delete "a salt or solvate thereof";

<u>In the Claims:</u> Col. 68, line 53 (claim 1), after "$R_5$", delete

UNITED STATES PATENT AND TRADEMARK OFFICE
CERTIFICATE OF CORRECTION

PATENT NO. : 5,478,826
DATED : December 26, 1995
INVENTOR(S) : Javier Bartroli et al.

It is certified that error appears in the above-indentified patent and that said Letters Patent is hereby corrected as shown below:

the comma; Col. 68, line 65 (claim 1), "-SO$_2$(C$_{1-4}$" should be -- -SO$_2$(C$_{1-4}$ --; Col. 69, line 16 (claim 4), "claims 2" should be -- claim 1 --; Col. 69, line 43 (claim 6), "-C(-O)-" should be -- -C(=O)- --; Col. 69, line 55 (claim 6), "2-cloro-4" should be -- 2-chloro-4 --; Col. 70, line 35 (claim 10), "(SR*,6R*)" should be -- (5R*,6R*) --; Col. 70, line 38 (claim 11), "(SR,6R)" should be -- (5R,6R) --; Col. 70, line 41 (claim 12), "(SR*,6R*)" should be -- (5R*,6R*) --; Col. 70, line 45 (claim 13), "6-(1H" should be -- 6-[(1H --; Col. 70, line 50 (claim 15), "(SR,6R)" should be -- (5R,6R) --; Col. 70, line 56 (claim 17), "(SR,6R)" should be -- (5R,6R) --; Col. 70, line 63 (claim 19), "triazol-]-" should be -- triazol-1- --.

Signed and Sealed this

Twentieth Day of May, 1997

*Attest:*

BRUCE LEHMAN

*Attesting Officer*    Commissioner of Patents and Trademarks